(12) United States Patent
Liu et al.

(10) Patent No.: US 7,501,408 B2
(45) Date of Patent: Mar. 10, 2009

(54) INHIBITORS OF CATHEPSIN S

(75) Inventors: Hong Liu, San Diego, CA (US); Arnab Chatterjee, Encinitas, CA (US); David C. Tully, San Diego, CA (US); Phillip Alper, San Diego, CA (US); Badry Bursulaya, San Diego, CA (US); Jianhua Guo, San Diego, CA (US); David H. Woodmansee, Basel (CH); Daniel Mutnick, San Diego, CA (US); Donald S. Karanewsky, Escondido, CA (US); Yun He, Shanghai (CN)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 11/932,679

(22) Filed: Oct. 31, 2007

(65) Prior Publication Data

US 2008/0108595 A1    May 8, 2008

Related U.S. Application Data

(62) Division of application No. 10/922,515, filed on Aug. 18, 2004, now Pat. No. 7,314,872.

(60) Provisional application No. 60/496,980, filed on Aug. 20, 2003.

(51) Int. Cl.
*C07D 417/12* (2006.01)
*C07D 295/10* (2006.01)
*A61K 31/541* (2006.01)

(52) U.S. Cl. .................. 514/227.5; 544/59; 544/60; 514/227.8

(58) Field of Classification Search ............ 544/59, 544/60; 514/227.5, 227.8
See application file for complete search history.

(56) References Cited

U.S. PATENT DOCUMENTS

| 5,932,737 | A  | 8/1999  | Itoh et al.    |
| 6,313,117 | B1 | 11/2001 | Bekkali et al. |
| 6,504,014 | B1 | 1/2003  | Isaacs et al.  |

FOREIGN PATENT DOCUMENTS

| JP | 2004-256525   |    | 9/2004  |
| WO | WO 01/09110   |    | 2/2001  |
| WO | WO 01/81613   | A2 | 11/2001 |

*Primary Examiner*—Kahsay T Habte
(74) *Attorney, Agent, or Firm*—Emily Tongoo Wu; Genomics Institute of the Novartis Research Foundation

(57) ABSTRACT

The present invention provides compounds, compositions and methods for the selective inhibition of cathepsin S. In a preferred aspect, cathepsin S is selectively inhibited in the presence of at least one other cathepsin isozyme. The present invention also provides methods for treating a disease state in a subject by selectively inhibiting cathepsin S. More particularly, the present invention provides compounds having Formula (I):

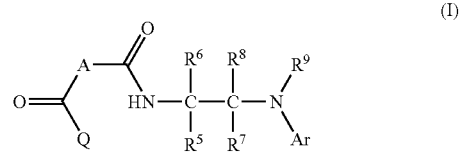

(I)

wherein Q is thiomorpholinyl; and
A, $R^5$, $R^6$, $R^7$, $R^8$, $R^9$ and Ar are substituents.

16 Claims, 1 Drawing Sheet

INHIBITORS OF CATHEPSIN S

CROSS-REFERENCE TO RELATED APPLICATIONS

This application is a divisional of U.S. patent application Ser. No. 10/922,515, filed on Aug. 18, 2004, which claims the benefit of U.S. provisional patent application No. 60/496,980, filed Aug. 20, 2003, each of which is incorporated herein by reference in its entirety for all purposes.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, *J Biol Chem* 1997, 272(13), 8109-12; Saftig, P., E. Hunziker, et al., *Adv Exp Med Biol* 2000+*ADs* 2000, 477, 293-303; Saftig, P., E. Hunziker, et al., *Proc Natl Acad Sci USA* 1998, 95(23), 13453-8), periodontal diseases, Paget's disease, atherosclerosis (Jormsjo, S., D. M. Wuttge, et al., *Am J Pathol* 2002 161(3), 939-45), multiple sclerosis (Beck, H., G. Schwarz, et al., *Eur J Immunol* 2001, 31(12), 3726-36), rheumatoid arthritis (Nakagawa, T. Y., W. H. Brissette, et al., *Immunity* 1999, 10(2), 207-17; Hou, W. S., Z. Li, et al., *Am J Pathol* 2001, 159(6), 2167-77), juvenile onset diabetes, lupus, asthma (Cimerman, N., P. M. Brguljan, et al., *Pflugers Arch* 2001, 442(6 Suppl 1), R204-6), tissue rejection, Alzheimer's disease (Lernere, C. A., J. S. Munger, et al., *Am J Pathol* 1995, 146(4), 848-60), Parkinson's disease (Liu, Y., L. Fallon, et al., *Cell* 2002, 111(2), 209-18), neuronal degeneration, shock (Jaeschke, H., M. A. Fisher, et al., *J Immunol* 1998, 160(7), 3480-6), cancer (Fernandez, P. L., X. Farre, et al., *Int J Cancer* 2001, 95(1), 51-5), malaria (Malhotra, P., P. V. Dasaradhi, et al., *Mol Microbiol* 2002, 45(5), 1245-54), Chagas (Eakin, A. E., A. A. Mills, et al., *J Biol Chem* 1992, 267(11), 7411-20), leishmaniasis, shistosomiasis, and African trypanosomiasis (Caffrey, C. R., S. Scory, et al., *Curr Drug Targets* 2000, 1(2), 155-62; Lalmanach, G., A. Boulange, et al., *Biol Chem* 2002, 383(5), 739-49).

Cathepsins are a subclass of cysteine protease that belong to the enzyme classification EC 3.4.22 (Barrett, A. J., N. D. Rawlings, et al., *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281-94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al., *Immunity* 1999, 10(2) 197-206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al., *J Biol Chem* 1996, 271(4), 2126-32). There is a need in the art for compounds and methods that selectively inhibit specific cysteine proteases for treating several pathogenic disorders in mammals. The present invention satisfies these and other needs.

SUMMARY OF THE INVENTION

The present invention provides compounds, compositions and methods for the selective inhibition of cathepsin S. The compounds of the present invention are selective for cathepsin S in the presence of other cathepsin isozymes. In a preferred embodiment, the compounds of the present invention are selective for cathepsin S in the presence of cathepsin K, L, B, or combinations thereof. The present invention also provides methods for treating a disease state in a subject by selectively inhibiting cathepsin S in the presence of other cathepsin isozymes. In a preferred aspect, cathepsin S is selectively inhibited in the presence of cathepsin K, L, B, or combinations thereof.

In one aspect, the present invention provides compounds of Formula I:

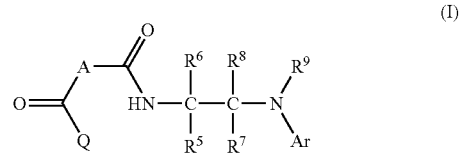

(I)

or a pharmaceutically acceptable salt or prodrug thereof, wherein:

Q is a heterocycle selected from the group consisting of azetidinyl, pyrrolidinyl, piperidyl, morpholinyl, thiomorpholinyl, piperazinyl and indolinyl substituted with 0-2 $R^Q$, wherein Q is connected to —C(=O)— via a ring nitrogen atom; and $NR^{25}R^{26}$;

each $R^Q$ is independently a member selected from the group consisting of OH, F, Cl, —S(=O)$_2$CH$_3$—, acetyl, =O, $C_1$-$C_6$ alkyl, $C_1$-$C_6$ alkoxy, CF$_3$, OCF$_3$ and $NR^{10}R^{11}$;

A is a member selected from the group consisting of —O—CR$^1$R$^2$—, —NH—CR$^1$R$^2$—, —CR$^3$R$^4$—O—, and —CR$^3$R$^4$—CR$^1$R$^2$—;

each of $R^1$ and $R^3$ is independently a member selected from the group consisting of H, a $C_1$-$C_6$ alkoxy, a $C_1$-$C_6$ alkyl substituted with 0-2 $R^{1a}$, wherein said $C_1$-$C_6$ alkyl may optionally contain a heteroatom selected from the group consisting of —O—, —S—, —S(=O)— and —S(=O)$_2$—; a $C_2$-$C_6$ alkenyl, a $C_3$-$C_6$ alkynyl, a $C_3$-$C_7$ cycloalkyl substituted with 0-2 $R^Q$, and a $C_7$-$C_{11}$ bicycloalkyl substituted with 0-2 $R^Q$; phenyl substituted with 0-3 $R^{13}$, a 5- to 6-membered heteroaryl containing 1 to 4 heteroatoms each independently a member selected from the group consisting of N, O and S, wherein said heteroaryl is substituted with 0-3 $R^{13}$;

each $R^{1a}$ is independently a member selected from the group consisting of a $C_6$-$C_{10}$ aryl substituted with 0-3 $R^{13}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{13}$, a $C_3$-$C_8$ cycloalkyl substituted with 0-2 $R^Q$, a $C_7$-$C_{11}$ bicycloalkyl substituted with 0-2 $R^Q$, and a $C_1$-$C_3$ perfluoroalkyl;

each of $R^2$ and $R^4$ is independently a member selected from the group consisting of H, F, OH, $C_1$-$C_6$ alkyl and $C_1$-$C_6$ alkoxy;

$R^5$ is a member selected from the group consisting of H, C(=O)OR$^{14}$, C(=O)NR$^{15}$R$^{16}$, phenyl substituted with 0-2 R$^{13}$, and a 5- to 6-membered heteroaryl containing 1 to 4 heteroatoms each independently a member selected from the group consisting of N, O and S, wherein said heteroaryl is substituted with 0-2 R$^{13}$, C$_3$-C$_7$ cycloalkyl, C$_1$-C$_6$ alkyl substituted with 0-2 R$^{21}$, wherein said C$_1$-C$_6$ alkyl may optionally contain a heteroatom selected from the group consisting of —O—, —S—, —S(=O)—, —S(=O)$_2$— and —NR$^{22}$—;

each of R$^6$, R$^7$, R$^8$ and R$^9$ is independently a member selected from the group consisting of H and C$_1$-C$_6$ alkyl;

alternatively, R$^5$ and R$^7$ are taken together to form a C$_5$-C$_7$ cycloalkyl, wherein a methylene of said C$_5$-C$_7$ cycloalkyl may optionally be replaced with a heteroatom selected from the group of —O—, —S—, —S(=O)—, and —S(=O)$_2$—;

each R$^{10}$ is independently a member selected from the group consisting of H, C$_1$-C$_4$ alkyl, (C$_1$-C$_4$ alkyl)-C(=O)— and (C$_1$-C$_4$ alkyl)-S(=O)$_2$—;

each R$^{11}$ is independently a member selected from the group consisting of H and C$_1$-C$_4$ alkyl;

each R$^{12}$ is independently a member selected from the group consisting of H, C$_3$-C$_8$ cycloalkyl, a phenyl substituted with 0-3 R$^{13}$, a 5- to 6-membered heteroaryl containing 1 to 4 heteroatoms each independently a member selected from the group consisting of N, O and S, wherein said 5- to 6-membered heteroaryl is substituted with 0-3 R$^{13}$, and a C$_1$-C$_6$ alkyl substituted with 0-1 R$^{19}$;

each R$^{13}$ is independently a member selected from the group consisting of H, OH, F, Cl, Br, CN, NO$_2$, COOR$^{17}$, C(=O)NR$^{17}$R$^{18}$, S(=O)$_2$NR$^{17}$R$^{18}$, acetyl, —SCH$_3$, —S(=O)CH$_3$, —S(=O)$_2$CH$_3$, —NR$^{10}$R$^{11}$, C$_1$-C$_6$ alkoxy, C$_1$-C$_3$ perfluoroalkyl, C$_1$-C$_3$ perfluoroalkoxy and a C$_1$-C$_6$ alkyl;

each R$^{14}$ is independently a member selected from the group consisting of H, C$_3$-C$_7$ cycloalkyl, C$_1$-C$_4$ alkyl substituted with 0-1 R$^{19}$, and a phenyl substituted with 0-3 R$^{13}$;

each R$^{15}$ is independently a member selected from the group consisting of H, C$_3$-C$_8$ cycloalkyl, a phenyl substituted with 0-3 R$^{13}$, and a C$_1$-C$_6$ alkyl substituted with 0-1 R$^{19}$;

each R$^{16}$ is independently a member selected from the group consisting of H and C$_1$-C$_4$ alkyl;

alternatively, R$^{15}$ and R$^{16}$ on the same N atom are taken together to form a C$_5$-C$_7$ heterocycle containing 1-2 heteroatoms each independently a member selected from the group consisting of N, O and S;

each of R$^{17}$ and R$^{18}$ is independently a member selected from the group consisting of H, C$_1$-C$_4$ alkyl and C$_3$-C$_6$ cycloalkyl;

each R$^{19}$ is independently a member selected from the group consisting of H, C$_3$-C$_7$ cycloalkyl, a phenyl substituted with 0-3 R$^{13}$ and a 5- to 6-membered heteroaryl containing 1 to 4 heteroatoms each independently a member selected from the group consisting of N, O and S, wherein said 5- to 6-membered heteroaryl is substituted with 0-3 R$^{13}$;

Ar is a member selected from the group consisting of phenyl substituted with 0-3 R$^{20}$, and a 5- to 10-membered heteroaryl containing 1 to 4 heteroatoms each independently a member selected from the group consisting of N, O and S; wherein said heteroaryl is substituted with 0-3 R$^{20}$;

each R$^{20}$ is independently a member selected from the group consisting of H, F, Cl, Br, CN, OR$^{12}$, SCH$_3$, S(=O)CH$_3$, S(=O)$_2$CH$_3$, S(=O)$_2$NR$^{17}$R$^{18}$, NR$^{10}$R$^{11}$, acetyl, —S(=O)$_2$NH(C=O)CH$_3$, C(=O)NR$^{17}$R$^{18}$, CO$_2$R$^{17}$, C(=NH)NH$_2$, C$_1$-C$_6$ alkyl, CF$_3$, OCF$_3$ and OCF$_2$H;

alternatively, R$^{20}$ and R$^9$ are taken together to form a 5- to 7-membered heterocyclic ring containing 1-2 heteroatoms each independently a member selected from the group consisting of N, O and S; wherein said 5 to 7 membered heterocyclic ring is ortho-fused to Ar; wherein said 5- to 7-membered heterocyclic ring may be optionally substituted with 0-2 R$^{24}$;

each R$^{21}$ is independently a member selected from the group consisting of H, OH, F, Cl, CN, NO$_2$, C(=O)OR$^{14}$, C(=O)NR$^{15}$R$^{16}$, NR$^{22}$R$^{23}$, C$_1$-C$_3$ perfluoroalkoxy, C$_1$-C$_4$ alkoxy, C$_2$-C$_4$ alkenyl, C$_2$-C$_4$ alkynyl, phenyl substituted with 0-3 R$^{13}$, a 5- to 6-membered heteroaryl containing 1 to 4 heteroatoms each independently a member selected from the group consisting of N, O and S, wherein said heteroaryl is substituted with 0-3 R$^{13}$, C$_3$-C$_8$ heterocycle containing 1 to 2 heteroatoms each independently a member selected from the group consisting of N, O and S, wherein said heterocycle is substituted with 0-2 R$^{13}$ and is saturated or partially unsaturated, and C$_3$-C$_8$ cycloalkyl;

R$^{22}$ is independently a member selected from the group consisting of H, $^t$BOC, Cbz, C$_3$-C$_8$ cycloalkyl, (C$_1$-C$_6$ alkyl)-C(=O)—, (C$_1$-C$_6$ alkyl)-S(=O)$_2$—, a C$_1$-C$_6$ alkyl substituted with 0-1 R$^{19}$, a phenyl substituted with 0-3 R$^{13}$ and a 5- to 6-membered heteroaryl containing 1 to 4 heteroatoms each independently a member selected from the group consisting of N, O and S, wherein said 5- to 6-membered heteroaryl is substituted with 0-3 R$^{13}$;

each R$^{23}$ is independently a member selected from the group consisting of H and C$_1$-C$_4$ alkyl.

each R$^{24}$ is independently a member selected from the group consisting of C$_1$-C$_4$ alkyl, F, Cl and C$_1$-C$_4$ alkoxy, CF$_3$ and OCF$_3$;

alternatively, two R$^{24}$ may be combined to form C$_3$-C$_6$ cycloalkyl.

each of R$^{25}$ and R$^{26}$ is independently a member selected from the group consisting of C$_1$-C$_6$ alkyl, wherein said C$_1$-C$_6$ alkyl may optionally contain a heteroatom selected from the group consisting of —O—, —S—, —S(=O)—, —S(=O)$_2$— and —NR$_{22}$—.

In a second aspect, the present invention provides a pharmaceutical composition comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

These and other aspects, objects and embodiments will become more apparent when read with the accompanying FIGURE and detailed description which follows.

DETAILED DESCRIPTION OF THE INVENTION

I. Definitions

Figure 1:
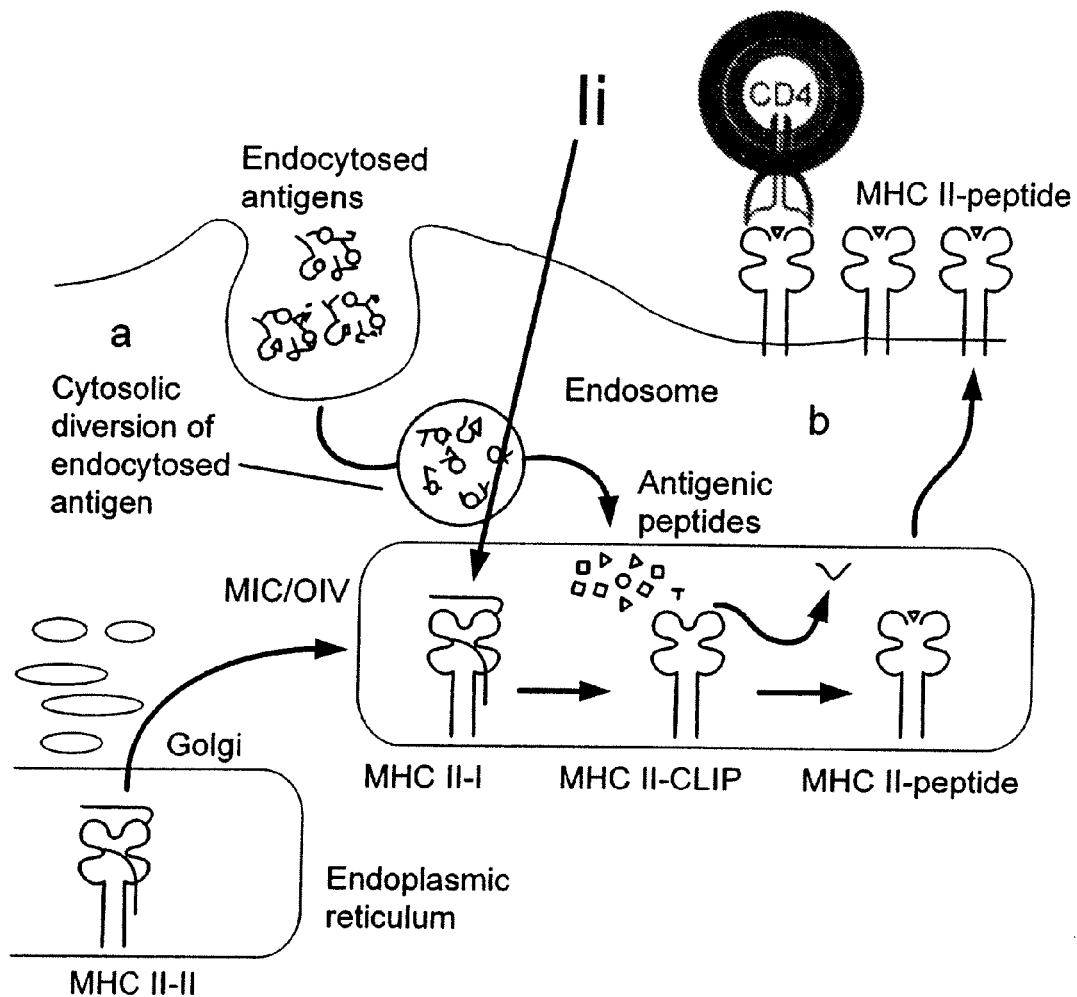
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

| | |
|---|---|
| Ac | acetyl |
| Bn | benzyl |
| Boc | t-butoxycarbonyl |
| Cbz or Z | benzyloxycarbonyl |
| DCC | N,N'-dicyclohexylcarbodiimide |
| DCM | dichoromethane |
| DIBAL | diisobutylaluminum hydride |
| DIC | N,N'-diisopropylcarbodiimide |
| DIEA or DIPEA | diisopropylethylamine |
| DMAP | 4-(dimethylamino)pyridine |
| DMF | dimethylformamide |
| DMSO | dimethyl sulfoxide |
| EDC or EDCI | 1-ethyl-3-(dimethylaminopropyl)-carbodiimide |
| Fmoc | 9-fluorenylmethoxycarbonyl |
| HATU | O-(7-azabenzoatriazol-1-yl)-N,N,N',N'-tetramethyluronium hexafluorophosphate |
| HOBt | 1-hydroxybenzotriazole |
| KHMDS | potassium hexamethyldisilazide |
| LAH | lithium aluminum hydride |
| LDA | lithium diisopropylamide |
| LHMDS | lithium hexamethyldisilazide |
| m-CPBA | m-chloroperbenzoic acid |
| MW | microwave |
| NaHMDS | sodium hexamethyldisilazide |
| PG | protecting group |
| PTSA | p-toluenesulfonic acid |
| Py | pyridine |
| RT or rt | room temperature |
| TEA | triethylamine |
| Tf | trifluoromethanesulfonyl |
| TFA | trifluoroacetic acid |
| THF | tetrahydrofuran |
| Tol | p-tolyl |

The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

An alkyl group is branched or unbranched and contains 1 to 7 carbon atoms, preferably 1-4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2-4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2-4 carbon atoms, e.g. as acetylenyl, propynyl, isoprpropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, or optionally substituted amino-oxy or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7.

An alkoxy (or alkyloxy) group preferably contains 1-7 carbon atoms, more preferably 1-6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl.

Amino can be optionally substituted by, e.g., alkyl.

Carbocyclic represents a saturated or partially unsaturated cyclic hydrocarbon with 5 to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2, hetero atoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W.H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{app}$ using described methods (Kuzmic, P., K. C. Elrod, et al., *Anal Biochem* 2000, 286(1), 45-50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$ for competitive inhibitors by using the following relationship:

$$K_i = \frac{K_i^{app}}{1 + [S]/K_m}.$$

Polycyclic ring systems in which any two adjacent rings have two (e.g., only two), adjacent atoms in common are said to be "ortho-fused". Such ring systems have n common sides and 2n common atoms.

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

II. General

Cathepsin S is a cysteine protease that has been associated with several normal and disease processes in mammals. Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme.

III. Compounds

A. Preparation of Compounds

In one embodiment, the arylaminoethylamines 1A (Scheme 1) used in the present invention can be prepared by a decarboxylative ring opening of oxazolidin-2-one with an aromatic amine as described in E. Altman et al., *J. Med Chem.* 2002, 45, 2352-54 and references cited therein.

Scheme 1

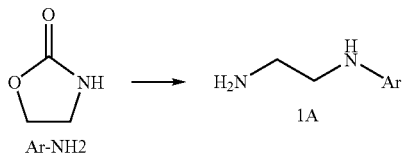

Another synthetic route to the diamines used in the present invention is illustrated in Scheme 2.

Scheme 2

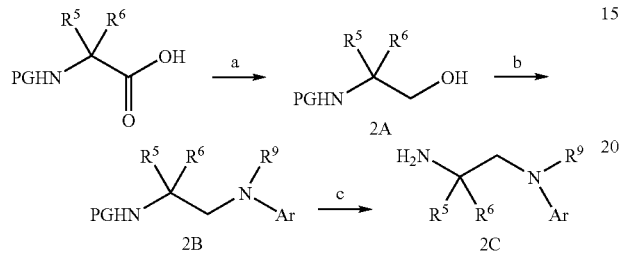

a) [BH$_3$.THF, THF 0° C.] or [i)TEA, i-butyl-chloroformate, THF, 0° C.; ii) NaBH$_4$, H$_2$O, 0° C. to RT];
b) i) Dess-Martin periodinane, DCM; ii) NHR$^9$Ar, NaCNBH$_3$, AcOH, MeOH;
c) removal of PG.

A N-protected amino acid can be reduced using either a BH$_3$ method or NaBH$_4$ reduction of the corresponding mixed anhydride [see R. C. Larock *A guide to functional group preparations* pp. 548-552, Wiley-VCH, 1989] to obtain 2A (Scheme 2). One can then oxidize the alcohol to the aldehyde and reductively aminate the resulting aldehyde with an amine to afford 2B. This intermediate can then be deprotected using the appropriate reagents for the PG, such as TFA for Boc.

Synthetic approaches to indolines used in this invention are widely described in the literature and well know to one skilled in the art. Typical methods include, but are not limited to, the methods disclosed in the following references: (a) G. W. Gribble et al., *Synthesis* 1977, 859; (b) A. Smith et al., *Chem. Commun.* 1965, 427; (c) G. W. Gribble et al., *J. Am. Chem. Soc.* 1974, 96, 7812; (d) J. G. Berger *Synthesis* 1974, 508; (e) L. J. Dolby et al., *J. Heterocycl. Chem.* 1966, 3, 124; (f) W. A. Remers et al., *J. Org. Chem.* 1971, 36, 279; (g) S. O'Brien et al., *J. Chem. Soc.* 1960, 4609; (h) Y. Kikugawa et al., *Synthesis* 1978, 477.

Synthetic approaches to non-commercially available α- and β-amino acids used in this invention are widely described in the literature and well know to one skilled in the art. Suitable methods include, but are not limited to, those disclosed in the following references: (a) D. J. Ager et al., *Current opinion in drug discovery & development* 2001, 4, 800-807; (b) R. O. Duthaler *Tetrahedron* 1994, 50, 1539-1650; (c) M. J. O'Donnell *Aldrichimica Acta* 2001, 34, 3-15; (d) K. B. Sharpless et al., *J. Am. Chem. Soc.* 1998, 120, 1207-17; (e) E. Juaristi et al., *Aldrichimica Acta* 1994, 27, 3-11; (f) D.C. Cole *Tetrahedron* 1994, 50, 9517-9582 and references cited therein.

Compounds of the present invention in which A is —NH—CR$^1$R$^2$ in Formula I, can be made via the route shown in Scheme 3. Polystyrene aldehyde (PAL) resin was reductively aminated with a monoaryl diamine (NH$_2$CH$_2$CH$_2$NR$^9$Ar) to obtain the resin 3A (Scheme 3). This material was acylated with an N-protected amino acid using standard conditions [as described in A. R. Chamberlin, *Chem. Rev.* 1997, 97, 2243-2266] and the product was then deprotected with piperidine to furnish 3B. After acylation with QCOCl under standard coupling condition, cleavage from resin using TFA furnished the urea 3C.

Scheme 3

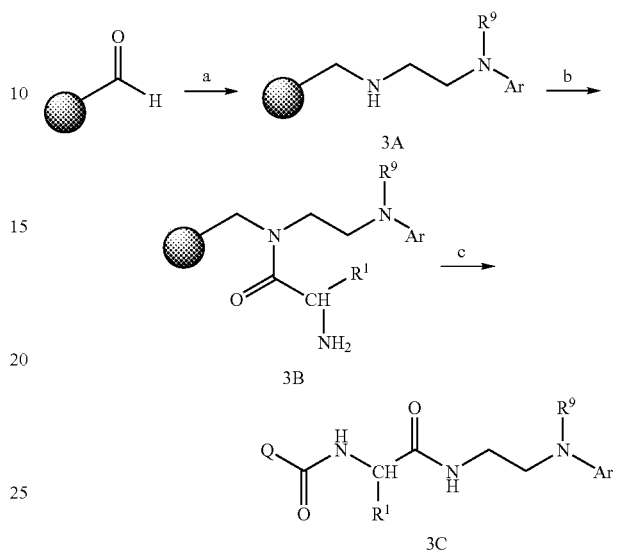

a) i) NH$_2$CH$_2$CH$_2$NR$^9$Ar, AcOH, DMF, rt;
   ii) NaHB(OAc)$_3$, DMF;
b) i) FmocHNCHR$^1$CO$_2$H, HOBt, DIC, DMF, rt;
   ii) 20% piperidine in DMF;
c) i) QCOCl, base, DMF, rt;
   ii) TFA/DCM/H$_2$O.

An illustration of the compounds of the present invention in which A=—CR$^3$H—O— in Formula I, is given in Scheme 4.

Scheme 4

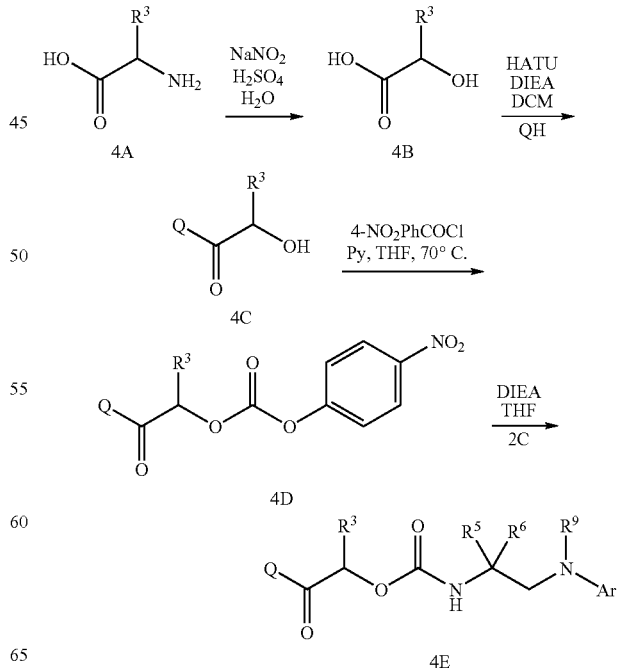

Scheme 5

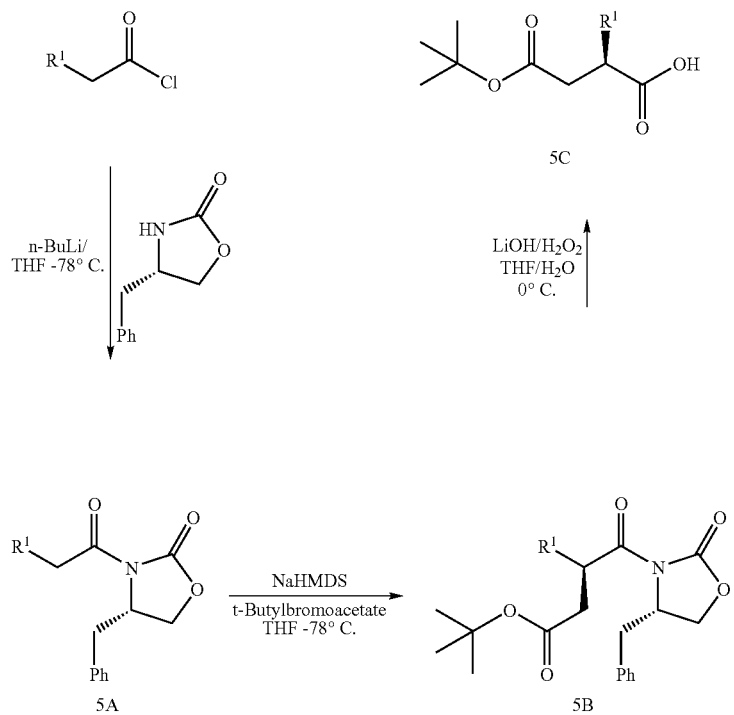

Methods for the synthesis of monosubstituted succinate derivatives are known in the art and are disclosed in a number of references including (a) D. A. Evans et al., *J. Org. Chem.* 1999, 64, 6411; (b) D. W. C. MacMillan et al., *J. Am. Chem. Soc.* 2001, 123, 2912; (c) S. Azam et al., *J. Chem. Soc. Perkin Trans.* 1 1996, 621; (d) A. Abell et al., *Org. Lett.* 2002, 4, 3663; (e) R. J. Cherney et al., *Bioorg. Med. Chem. Lett.* 2003, 13, 1297; (f) G. Shapiro et al., *Tetrahedron Lett.* 1992, 33, 2447; (g) N. J. S. Harmat et al., *Tetrahedron Lett.* 2000, 41, 1261. A representative procedure is outlined in Scheme 5 where acylation of an oxazolidinone chiral auxiliary with an acid chloride provides structure 5A. Alkylation of the corresponding enolate with t-butyl bromoacetate followed by LiOH/H$_2$O$_2$ mediated cleavage of the chiral auxiliary gives rise to the enantiomerically pure monosubstituted succinic acid monoester 5C.

Syn-2,3-disubstituted succinate derivatives can be accessed using the chemistry illustrated in Scheme 6, adapted from (a) M. J. Crimmin et al., *Synlett* 1993, 137; (b) C. Xue et al., *J. Org. Chem.* 2002, 67, 865 incorporated herein by references. Intermediate 5C was subjected to enolate formation using a 2.2 equivalent of a strong base followed by quenching with 1.5 equivalent of R$^3$X (wherein X=OTf, I, Br and the like), providing exclusively the syn diastereomer 6A after chromatography.

Scheme 6

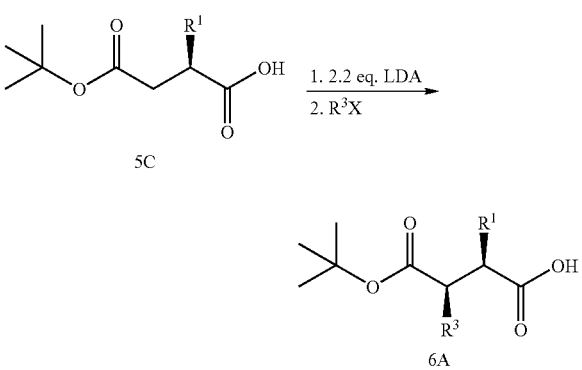

Anti-2,3-disubstituted succinate derivatives can be obtained via selective inversion at the C-3 carbon center described by M. J. Crimmin et al., *Synlett* 1993, 137.

Alternatively, racemic succinic acid esters can be converted to enantiomerically enriched succinic acids via an enzyme catalyzed kinetic resolution, according to the procedures described by (a) H. Oikiwa et al., *Tetrahedron Lett.* 1996, 37, 6169; (b) B. Wirz et al., *Tetrahedron: Asymmetry* 1997, 8, 187 and references cited therein.

The compounds of the present invention in which A=—CHR$^3$—CHR$^1$— in Formula I, can be prepared as illustrated in Scheme 7.

Scheme 7

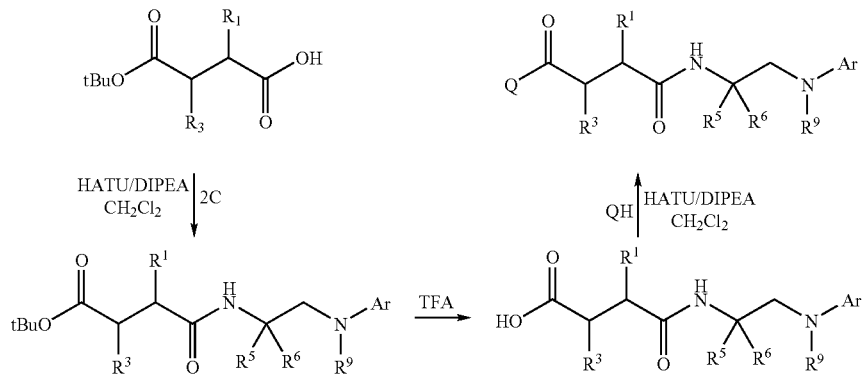

An illustration of the compounds of the present invention in which A=—O—CR³H— in formula I, is given in Scheme 8.

Scheme 8

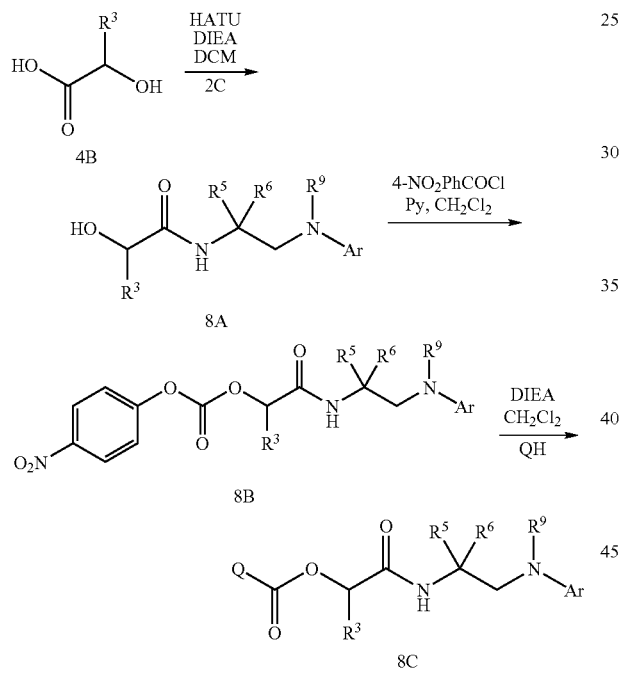

B. Preferred Compounds

Compounds that inhibit the cathepsin S activity can be found in U.S. Provisional Application Nos. 60/457,848 and 60/457,595, both filed Mar. 24, 2003, and 60/478,625 filed Jun. 13, 2003. The contents of each of the foregoing applications are incorporated herein by reference.

In one aspect, the present invention provides a compound of Formula I:

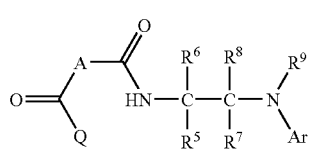

(I)

or a pharmaceutically acceptable salt or prodrug thereof, wherein:

Q is a heterocycle selected from the group consisting of azetidinyl, pyrrolidinyl, piperidyl, morpholinyl, thiomorpholinyl, piperazinyl and indolinyl substituted with 0-2 $R^Q$, wherein Q is connected to —C(=O)— via a ring nitrogen atom; and $NR^{25}R^{26}$;

each $R^Q$ is independently a member selected from the group consisting of OH, F, Cl, —S(=O)$_2$CH$_3$—, acetyl, =O, $C_1$-$C_6$ alkyl, $C_1$-$C_6$ alkoxy, $CF_3$, $OCF_3$ and $NR^{10}R^{11}$;

A is a member selected from the group consisting of —O—CR¹R²—, —NH—CR¹R²—, —CR³R⁴—O—, and —CR³R⁴—CR¹R²—;

each of $R^1$ and $R^3$ is independently a member selected from the group consisting of H, a $C_1$-$C_6$ alkoxy, a $C_1$-$C_6$ alkyl substituted with 0-2 $R^{13}$, wherein said $C_1$-$C_6$ alkyl may optionally contain a heteroatom selected from the group consisting of —O—, —S—, —S(=O)— and —S(=O)$_2$—; a $C_2$-$C_6$ alkenyl, a $C_3$-$C_6$ alkynyl, a $C_3$-$C_7$ cycloalkyl substituted with 0-2 $R^Q$, and a $C_7$-$C_{11}$ bicycloalkyl substituted with 0-2 $R^Q$; phenyl substituted with 0-3 $R^{13}$, a 5- to 6-membered heteroaryl containing 1 to 4 heteroatoms each independently a member selected from the group consisting of N, O and S, wherein said heteroaryl is substituted with 0-3 $R^{13}$;

each $R^{13}$ is independently a member selected from the group consisting of a $C_6$-$C_{10}$ aryl substituted with 0-3 $R^{13}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{13}$, a $C_3$-$C_8$ cycloalkyl substituted with 0-2 $R^Q$, a $C_7$-$C_{11}$ bicycloalkyl substituted with 0-2 $R^Q$, and a $C_1$-$C_3$ perfluoroalkyl;

each of $R^2$ and $R^4$ is independently a member selected from the group consisting of H, F, OH, $C_1$-$C_6$ alkyl and $C_1$-$C_6$ alkoxy;

$R^5$ is a member selected from the group consisting of H, C(=O)OR¹⁴, C(=O)NR¹⁵R¹⁶, phenyl substituted with 0-2 $R^{13}$, and a 5- to 6-membered heteroaryl containing 1 to 4 heteroatoms each independently a member selected from the group consisting of N, O and S, wherein said heteroaryl is substituted with 0-2 $R^{13}$, $C_3$-$C_7$ cycloalkyl, $C_1$-$C_6$ alkyl substituted with 0-2 $R^{21}$, wherein said $C_1$-$C_6$ alkyl may optionally contain a heteroatom selected from the group consisting of —O—, —S—, —S(=O)—, —S(=O)$_2$— and —NR$^{22}$—;

each of R$^6$, R$^7$, R$^8$ and R$^9$ is independently a member selected from the group consisting of H and C$_1$-C$_6$ alkyl;

alternatively, R$^5$ and R$^7$ are taken together to form a C$_5$-C$_7$ cycloalkyl, wherein a methylene of said C$_5$-C$_7$ cycloalkyl may optionally be replaced with a heteroatom selected from the group of —O—, —S—, —S(=O)—, and —S(=O)$_2$—;

each R$^{10}$ is independently a member selected from the group consisting of H, C$_1$-C$_4$ alkyl, (C$_1$-C$_4$ alkyl)-C(=O)— and (C$_1$-C$_4$ alkyl)-S(=O)$_2$—;

each R$^{11}$ is independently a member selected from the group consisting of H and C$_1$-C$_4$ alkyl;

each R$^{12}$ is independently a member selected from the group consisting of H, C$_3$-C$_8$ cycloalkyl, a phenyl substituted with 0-3 R$^{13}$, a 5- to 6-membered heteroaryl containing 1 to 4 heteroatoms each independently a member selected from the group consisting of N, O and S, wherein said 5- to 6-membered heteroaryl is substituted with 0-3 R$^{13}$, and a C$_1$-C$_6$ alkyl substituted with 0-1 R$^{19}$;

each R$^{13}$ is independently a member selected from the group consisting of H, OH, F, Cl, Br, CN, NO$_2$, COOR$^{17}$, C(=O)NR$^{17}$R$^{18}$, S(=O)$_2$NR$^{17}$R$^{18}$, acetyl, —SCH$_3$, —S(=O)CH$_3$, —S(=O)$_2$CH$_3$, —NR$^{10}$R$^{11}$, C$_1$-C$_6$ alkoxy, C$_1$-C$_3$ perfluoroalkyl, C$_1$-C$_3$ perfluoroalkoxy and a C$_1$-C$_6$ alkyl;

each R$^{14}$ is independently a member selected from the group consisting of H, C$_3$-C$_7$ cycloalkyl, C$_1$-C$_4$ alkyl substituted with 0-1 R$^{19}$, and a phenyl substituted with 0-3 R$^{13}$;

each R$^{15}$ is independently a member selected from the group consisting of H, C$_3$-C$_8$ cycloalkyl, a phenyl substituted with 0-3 R$^{13}$, and a C$_1$-C$_6$ alkyl substituted with 0-1 R$^{19}$;

each R$^{16}$ is independently a member selected from the group consisting of H and C$_1$-C$_4$ alkyl;

alternatively, R$^{15}$ and R$^{16}$ on the same N atom are taken together to form a C$_5$-C$_7$ heterocycle containing 1-2 heteroatoms each independently a member selected from the group consisting of N, O and S;

each of R$^{17}$ and R$^{18}$ is independently a member selected from the group consisting of H, C$_1$-C$_4$ alkyl and C$_3$-C$_6$ cycloalkyl;

each R$^{19}$ is independently a member selected from the group consisting of H, C$_3$-C$_7$ cycloalkyl, a phenyl substituted with 0-3 R$^{13}$ and a 5- to 6-membered heteroaryl containing 1 to 4 heteroatoms each independently a member selected from the group consisting of N, O and S, wherein said 5- to 6-membered heteroaryl is substituted with 0-3 R$^{13}$;

Ar is a member selected from the group consisting of phenyl substituted with 0-3 R$^{20}$, and a 5- to 10-membered heteroaryl containing 1 to 4 heteroatoms each independently a member selected from the group consisting of N, O and S; wherein said heteroaryl is substituted with 0-3 R$^{20}$;

each R$^{20}$ is independently a member selected from the group consisting of H, F, Cl, Br, CN, OR$^{12}$, SCH$_3$, S(=O)CH$_3$, S(=O)$_2$CH$_3$, S(=O)$_2$NR$^{17}$R$^{18}$, NR$^{10}$R$^{11}$, acetyl, —S(=O)$_2$NH(C=O)CH$_3$, C(=O)NR$^{17}$R$^{18}$, CO$_2$R$^{17}$, C(=NH)NH$_2$, C$_1$-C$_6$ alkyl, CF$_3$, OCF$_3$ and OCF$_2$H;

alternatively, R$^{20}$ and R$^9$ are taken together to form a 5- to 7-membered heterocyclic ring containing 1-2 heteroatoms each independently a member selected from the group consisting of N, O and S; wherein said 5 to 7 membered heterocyclic ring is ortho-fused to Ar; wherein said 5- to 7-membered heterocyclic ring may be optionally substituted with 0-2 R$^{24}$;

each R$^{21}$ is independently a member selected from the group consisting of H, OH, F, Cl, CN, NO$_2$, C(=O)OR$^{14}$, C(=O)NR$^{15}$R$^{16}$, NR$^{22}$R$^{23}$, C$_1$-C$_3$ perfluoroalkoxy, C$_1$-C$_4$ alkoxy, C$_2$-C$_4$ alkenyl, C$_2$-C$_4$ alkynyl, phenyl substituted with 0-3 R$^{13}$, a 5- to 6-membered heteroaryl containing 1 to 4 heteroatoms each independently a member selected from the group consisting of N, O and S, wherein said heteroaryl is substituted with 0-3 R$^{13}$, C$_3$-C$_8$ heterocycle containing 1 to 2 heteroatoms each independently a member selected from the group consisting of N, O and S, wherein said heterocycle is substituted with 0-2 R$^{13}$ and is saturated or partially unsaturated, and C$_3$-C$_8$ cycloalkyl;

R$^{22}$ is independently a member selected from the group consisting of H, $^t$BOC, Cbz, C$_3$-C$_8$ cycloalkyl, (C$_1$-C$_6$ alkyl)-C(=O)—, (C$_1$-C$_6$ alkyl)-S(=O)$_2$—, a C$_1$-C$_6$ alkyl substituted with 0-1 R$^{19}$, a phenyl substituted with 0-3 R$^{13}$ and a 5- to 6-membered heteroaryl containing 1 to 4 heteroatoms each independently a member selected from the group consisting of N, O and S, wherein said 5- to 6-membered heteroaryl is substituted with 0-3 R$^{13}$;

each R$^{23}$ is independently a member selected from the group consisting of H and C$_1$-C$_4$ alkyl.

each R$^{24}$ is independently a member selected from the group consisting of C$_1$-C$_4$ alkyl, F, Cl and C$_1$-C$_4$ alkoxy, CF$_3$ and OCF$_3$;

alternatively, two R$^{24}$ may be combined to form C$_3$-C$_6$ cycloalkyl.

each of R$^{25}$ and R$^{26}$ is independently a member selected from the group consisting of C$_1$-C$_6$ alkyl, wherein said C$_1$-C$_6$ alkyl may optionally contain a heteroatom selected from the group consisting of —O—, —S—, —S(=O)—, —S(=O)$_2$— and —NR$_{22}$—.

Compounds of the present invention are cathepsin S inhibitors. In particularly preferred aspects, the cathepsin S inhibitors are non-inhibitory toward cathepsin K, L, B, or combinations thereof.

In a preferred aspect, the present invention provides a compound according to Formula Ia:

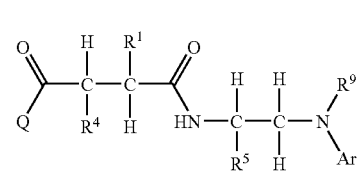

(Ia)

wherein:

R$^1$ is independently a member selected from the group consisting of H, C$_1$-C$_6$ alkyl substituted with 0-1 R$^{1a}$, wherein said C$_1$-C$_6$ alkyl may optionally contain a heteroatom selected from the group consisting of —O—, —S—, and —S(=O)$_2$, a C$_2$-C$_6$ alkenyl, a C$_3$-C$_7$ cycloalkyl substituted with 0-2 R$^Q$, and a C$_7$-C$_{11}$ bicycloalkyl substituted with 0-2 R$^Q$; phenyl substituted with 0-3 R$^{13}$, a 5- to 6-membered heteroaryl containing 1 to 4 heteroatoms each independently a member selected from the group consisting of N, O and S, wherein said heteroaryl is substituted with 0-3 R$^{13}$;

R$^4$ is a member selected from the group consisting of H, F, OH and C$_1$-C$_6$ alkyl.

In another preferred aspect, the present invention provides a compound according to Formula Ib:

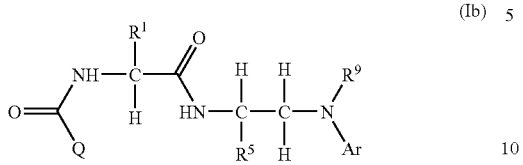

wherein:
R$^1$ is selected from the group consisting of C$_1$-C$_6$ alkyl, C$_1$-C$_4$ alkyl substituted with 1 R$^{1a}$, wherein said C$_1$-C$_4$ alkyl may optionally contain a heteroatom selected from the group consisting of —O—, —S— and —S(=O)$_2$—;
R$^{1a}$ is a member selected from the group consisting of a phenyl substituted with 0-3 R$^{13}$, a C$_3$-C$_7$ cycloalkyl substituted with 0-2 R$^Q$, and a C$_7$-C$_{11}$ bicycloalkyl substituted with 0-2 R$^Q$.

In yet another preferred aspect, the present invention provides a compound according to Formula Ic:

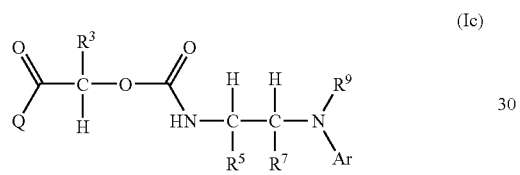

wherein:
R$^{1a}$ is selected from the group consisting of C$_1$-C$_6$ alkyl, C$_1$-C$_4$ alkyl substituted with 1 R$^{1a}$, wherein said C$_1$-C$_4$ alkyl may optionally contain a heteroatom selected from the group consisting of —O—, —S— and —S(=O)$_2$—; a C$_3$-C$_7$ cycloalkyl substituted with 0-2 R$^Q$, and a C$_7$-C$_{11}$ bicycloalkyl substituted with 0-2 R$^Q$; phenyl substituted with 0-3 R$^{13}$;
R$^{1a}$ is a member selected from the group consisting of a phenyl substituted with 0-3 R$^{13}$, a C$_3$-C$_7$ cycloalkyl substituted with 0-2 R$^Q$, and a C$_7$-C$_{11}$ bicycloalkyl substituted with 0-2 R$^Q$.

In still yet another preferred aspect, the present invention provides a compound according to Formula Id:

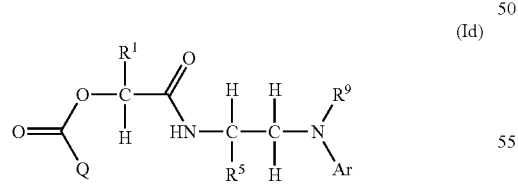

wherein:
R$^1$ is selected from the group consisting of C$_1$-C$_6$ alkyl, C$_1$-C$_4$ alkyl substituted with 1 R$^{1a}$, wherein said C$_1$-C$_4$ alkyl may optionally contain a heteroatom selected from the group consisting of —O—, —S—, and —S(=O)$_2$;
R$^{1a}$ is a member selected from the group consisting of a phenyl substituted with 0-3 R$^{13}$, C$_3$-C$_7$ cycloalkyl substituted with 0-2 R$^Q$, and a C$_7$-C$_{11}$ bicycloalkyl substituted with 0-2 R$^Q$;

R$^5$ is a member selected from the group consisting of H, phenyl substituted with 0-2 R$^{13}$, C$_3$-C$_7$ cycloalkyl, C$_1$-C$_6$ alkyl substituted with 0-1 R$^{21}$, wherein said C$_1$-C$_6$ alkyl may optionally contain a heteroatom selected from the group consisting of —O—, —S—, —S(=O)$_2$—;
each R$^{21}$ is independently a member selected from the group consisting of H, OH, F, C(=O)OR$^{14}$, C(=O)NR$^{15}$R$^{16}$, NR$^{22}$R$^{23}$, phenyl substituted with 0-3 R$^{13}$, and C$_3$-C$_7$ cycloalkyl;
Ar is a member selected from the group consisting of phenyl substituted with 0-3 R$^{20}$;
each R$^{20}$ is independently a member selected from the group consisting of H, F, Cl, Br, CN, OR$^{12}$, SCH$_3$, S(=O)CH$_3$, S(=O)$_2$CH$_3$, S(=O)$_2$NR$^{17}$R$^{18}$, NR$^{10}$R$^{11}$, acetyl, C(=O)NR$^{17}$R$^{18}$, CO$_2$R$^{17}$, C(=NH)NH$_2$, C$_1$-C$_6$ alkyl, CF$_3$, OCF$_3$;
alternatively, R$^{20}$ and R$^9$ are taken together to form a 5 membered heterocyclic ring containing 1 nitrogen, wherein said 5 membered heterocyclic ring is ortho-fused to Ar; wherein said 5-membered heterocyclic ring may be optionally substituted with 0-2 R$^{24}$.

In another aspect, the present invention provides a compound according to Formula Ie:

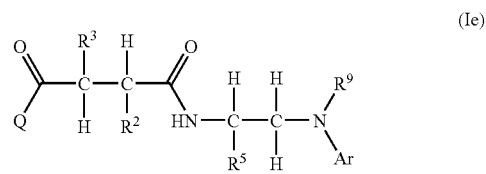

wherein:
R$^2$ is H;
R$^3$ are each independently selected from the group consisting of H, C$_1$-C$_6$ alkyl, C$_1$-C$_4$ alkyl substituted with 1 R$^{1a}$,
R$^{1a}$ is a member selected from the group consisting of a C$_3$-C$_7$ cycloalkyl substituted with 0-2 R$^Q$, and a C$_7$-C$_{11}$ bicycloalkyl substituted with 0-2 R$^Q$;
R$^5$ is a member selected from the group consisting of H, phenyl substituted with 0-2 R$^{13}$, C$_3$-C$_7$ cycloalkyl, C$_1$-C$_6$ alkyl substituted with 0-1 R$^{21}$, wherein said C$_1$-C$_6$ alkyl may optionally contain a heteroatom selected from the group consisting of —O—, —S—, —S(=O)$_2$—;
each R$^{21}$ is independently a member selected from the group consisting of H, OH, C(=O)OR$^{14}$, C(=O)NR$^{15}$R$^{16}$, NR$^{22}$R$^{23}$, phenyl substituted with 0-3 R$^{13}$, and C$_3$-C$_8$ cycloalkyl;
Ar is a member selected from the group consisting of phenyl substituted with 0-3 R$^{20}$,
each R$^{20}$ is independently a member selected from the group consisting of H, F, Cl, Br, CN, OR$^{12}$, SCH$_3$, S(=O)CH$_3$, S(=O)$_2$CH$_3$, S(=O)$_2$NR$^{17}$R$^{18}$, NR$^{10}$R$^{11}$, acetyl, —S(=O)$_2$NH(C=O)CH$_3$, C(=O)NR$^{17}$R$^{18}$, CO$_2$R$^{17}$, C(=NH)NH$_2$, C$_1$-C$_6$ alkyl, CF$_3$, OCF$_3$ and OCF$_2$H;
alternatively, R$^{20}$ and R$^9$ are taken together to form a 5-membered heterocyclic ring containing 1 nitrogen; wherein said 5-membered heterocyclic ring is ortho-fused to Ar; wherein said 5-membered heterocyclic ring may be optionally substituted with 0-2 R$^{24}$.

Q preferably has the following structures:

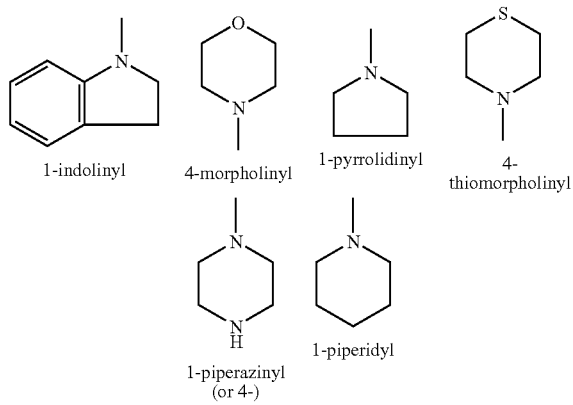

1-indolinyl   4-morpholinyl   1-pyrrolidinyl   4-thiomorpholinyl 1-piperazinyl (or 4-)   1-piperidyl Preferred compounds of Formula I are set forth below:
1. Morpholine-4-carboxylic acid (S)-2-cyclohexyl-1-[2-(5-fluoro-2,3-dihydro-indol-1-yl)-ethylcarbamoyl]-ethyl ester;
2. Morpholine-4-carboxylic acid {2-cyclohexyl-1-(S)-[2-(5-fluoro-2,3-dihydro-indol-1-yl)-ethylcarbamoyl]-ethyl}-amide;
3. Morpholine-4-carboxylic acid {2-cyclohexyl-1-(S)-[2-(4-fluoro-phenylamino)-ethylcarbamoyl]-ethyl}-amide;
4. Morpholine-4-carboxylic acid {2-cyclohexyl-1-(S)-[2-(4-methoxy-phenylamino)-ethylcarbamoyl]-ethyl}-amide;
5. [2-(4-Fluoro-phenylamino)-ethyl]-carbamic acid 1-(S)-cyclohexylmethyl-2-morpholin-4-yl-2-oxo-ethyl ester;
6. 2-(R)-Cyclohexylmethyl-N-[2-(4-fluoro-phenylamino)-ethyl]-4-morpholin-4-yl-4-oxo-butyramide;
7. [4-(R)-(5-Fluoro-3,3-dimethyl-2,3-dihydro-indol-1-yl)-tetrahydro-furan-3-(R)-yl]-carbamic acid 1-(S)-cyclohexylmethyl-2-morpholin-4-yl-2-oxo-ethyl ester;
8. 2-(R)-Cyclohexylmethyl-N-[2-(5-fluoro-2,3-dihydro-indol-1-yl)-1-(S)-methyl-ethyl]-4-morpholin-4-yl-4-oxo-butyramide;
9. 3-(R)-Cyclohexylmethyl-N-[2-(4-fluoro-phenylamino)-ethyl]-4-morpholin-4-yl-4-oxo-butyramide;
10. [1-(R)—Benzyloxymethyl-2-(5-fluoro-2,3-dihydro-indol-1-yl)-ethyl]-carbamic acid 1-(S)-cyclohexylmethyl-2-morpholin-4-yl-2-oxo-ethyl ester;
11. Morpholine-4-carboxylic acid 2-cyclohexyl-1-(S)-[2-(5-fluoro-2,3-dihydro-indol-1-yl)-1-(S)-methyl-ethylcarbamoyl]-ethyl ester;
12. Morpholine-4-carboxylic acid 2-cyclohexyl-1-(S)-[2-(5-fluoro-2,3-dihydro-indol-1-yl)-1-(S)-methyl-ethylcarbamoyl]-ethyl ester;
13. 2-(R)-Cyclohexylmethyl-4-morpholin-4-yl-4-oxo-N-[2-(4-trifluoromethoxy-phenylamino)-ethyl]-butyramide;
14. 2-(R)-Cyclohexylmethyl-N-[1-(S)-methyl-2-(4-trifluoromethoxy-phenylamino)-ethyl]-4-morpholin-4-yl-4-oxo-butyramide;
15. 2-(R)-Cyclopentylmethyl-N-[1-(S)-methyl-2-(4-trifluoromethoxy-phenylamino)-ethyl]-4-morpholin-4-yl-4-oxo-butyramide;
16. 2-(R)-Cyclopentylmethyl-3-(R)-methyl-N-[1-(S)-methyl-2-(4-trifluoromethoxy-phenylamino)-ethyl]-4-morpholin-4-yl-4-oxo-butyramide;
17. Morpholine-4-carboxylic acid {2-benzylsulfanyl-1-(R)-[1-(S)-methyl-2-(4-trifluoromethoxy-phenylamino)-ethylcarbamoyl]-ethyl}-amide;
18. Morpholine-4-carboxylic acid {1-(R)-[1-(S)-methyl-2-(4-trifluoromethoxy-phenylamino)-ethylcarbamoyl]-2-phenylmethanesulfonyl-ethyl}-amide;
19. (R)-2-Cyclohexylmethyl-N-[2-(4-methoxy-phenylamino)-ethyl]-4-morpholin-4-yl-4-oxo-butyramide;
20. 2-(R)-Cyclohexylmethyl-4-morpholin-4-yl-4-oxo-N-{1-(S)-[(4-trifluoromethoxy-phenylamino)-methyl]-butyl}-butyramide;
21. 2-(R)-(2-Cyclohexyl-ethyl)-N-[1-(S)-methyl-2-(4-trifluoromethoxy-phenylamino)-ethyl]-4-morpholin-4-yl-4-oxo-butyramide;
22. 2-(R)-Cyclohexylmethyl-4-morpholin-4-yl-4-oxo-N-{1-(S)-[(4-trifluoromethoxy-phenylamino)-methyl]-propyl}-butyramide;
23. 2-(R)-Cyclohexylmethyl-4-morpholin-4-yl-4-oxo-N-{3-phenyl-1-(S)-[(4-trifluoromethoxy-phenylamino)-methyl]-propyl}-butyramide;
24. 2-(R)-Cyclohexylmethyl-N-{2-methyl-1-(S)-[(4-trifluoromethoxy-phenylamino)-methyl]-propyl}-4-morpholin-4-yl-4-oxo-butyramide;
25. 5,5-Dimethyl-2-(R)-(2-morpholin-4-yl-2-oxo-ethyl)-hexanoic acid [1-(S)-methyl-2-(4-trifluoromethoxy-phenylamino)-ethyl]-amide;
26. 4,4-Dimethyl-2-(R)-(2-morpholin-4-yl-2-oxo-ethyl)-pentanoic acid [1-(S)-methyl-2-(4-trifluoromethoxy-phenylamino)-ethyl]-amide;
27. 2-(R)-Cyclopentylmethyl-4-morpholin-4-yl-4-oxo-N-{1-(S)-[(4-trifluoromethoxy-phenylamino)-methyl]-butyl}-butyramide;
28. 2-(R)-Cyclohexylmethyl-N-{3-methanesulfonyl-1-(S)-[(4-trifluoromethoxy-phenylamino)-methyl]-propyl}-4-morpholin-4-yl-4-oxo-butyramide;
29. 2-(R)-Cyclohexylmethyl-N-{3-methanesulfonyl-1-(R)-[(4-trifluoromethoxy-phenylamino)-methyl]-propyl}-4-morpholin-4-yl-4-oxo-butyramide;
30. 2-(R)-(2-Morpholin-4-yl-2-oxo-ethyl)-5-phenyl-pentanoic acid {2-methyl-1-(S)-[(4-trifluoromethoxy-phenylamino)-methyl]-propyl}-amide;
31. 2-(R)-Cyclopentylmethyl-N-{2-methyl-1-(S)-[(4-trifluoromethoxy-phenylamino)-methyl]-propyl}-4-morpholin-4-yl-4-oxo-butyramide;
32. N-{2-Methyl-1-(S)-[(4-trifluoromethoxy-phenylamino)-methyl]-propyl}-4-morpholin-4-yl-4-oxo-2-(R)-phenethyl-butyramide;
33. 2-(R)-(2-Cyclopentyl-ethyl)-N-{2-methyl-1-(S)-[(4-trifluoromethoxy-phenylamino)-methyl]-propyl}-4-morpholin-4-yl-4-oxo-butyramide;
34. N-{2-Methyl-1-(S)-[(4-trifluoromethoxy-phenylamino)-methyl]-propyl}-4-morpholin-4-yl-4-oxo-2-(S)-phenyl-butyramide;
35. 2-(S)-Cyclohexyl-N-{2-methyl-1-(S)-[(4-trifluoromethoxy-phenylamino)-methyl]-propyl}-4-morpholin-4-yl-4-oxo-butyramide;
36. 2-(R)-(2-Cyclopentyl-ethyl)-4-morpholin-4-yl-4-oxo-N-{1-(S)-[(4-trifluoromethoxy-phenylamino)-methyl]-propyl}-butyramide;
37. 2-(R)-(2-Cyclopentyl-ethyl)-4-morpholin-4-yl-4-oxo-N-{3-phenyl-1-(S)-[(4-trifluoromethoxy-phenylamino)-methyl]-propyl}-butyramide;
38. 4-Morpholin-4-yl-4-oxo-2-(R)-phenethyl-N-{1-(S)-[(4-trifluoromethoxy-phenylamino)-methyl]-propyl}-butyramide;
39. 4-Morpholin-4-yl-4-oxo-2-(S)-phenyl-N-{1-(S)-[(4-trifluoromethoxy-phenylamino)-methyl]-butyl}-butyramide;
40. 4-Morpholin-4-yl-4-oxo-2-(S)-phenyl-N-{3-phenyl-1-(S)-[(4-trifluoromethoxy-phenylamino)-methyl]-propyl}-butyramide;

41. 2-(S)-(4-Fluoro-phenyl)-N-{2-methyl-1-(S)-[(4-trifluoromethoxy-phenylamino)-methyl]-propyl}-4-morpholin-4-yl-4-oxo-butyramide;
42. 2-(S)-(4-Chloro-phenyl)-N-{2-methyl-1-(S)-[(4-trifluoromethoxy-phenylamino)-methyl]-propyl}-4-morpholin-4-yl-4-oxo-butyramide;
43. 2-(R)-(4-Chloro-phenyl)-N-{2-methyl-1-(S)-[(4-trifluoromethoxy-phenylamino)-methyl]-propyl}-4-morpholin-4-yl-4-oxo-butyramide;
44. 4-Morpholin-4-yl-4-oxo-2-(S)-phenyl-N-[1-(S)-phenyl-2-(4-trifluoromethoxy-phenylamino)-ethyl]-butyramide;
45. 2-(R)-Cyclohexylmethyl-4-morpholin-4-yl-4-oxo-N-[1-(S)-phenyl-2-(4-trifluoromethoxy-phenylamino)-ethyl]-butyramide;
46. 2-(R)-(2-Cyclopentyl-ethyl)-4-morpholin-4-yl-4-oxo-N-[1-(S)-phenyl-2-(4-trifluoromethoxy-phenylamino)-ethyl]-butyramide;
47. 2-(R)-(2-Morpholin-4-yl-2-oxo-ethyl)-pent-4-enoic acid {2-methyl-1-(S)-[(4-trifluoromethoxy-phenylamino)-methyl]-propyl}-amide;
48. 2-(S)-(4-Chloro-phenyl)-4-morpholin-4-yl-4-oxo-N-[1-(S)-phenyl-2-(4-trifluoromethoxy-phenylamino)-ethyl]-butyramide;
49. (R)-5,5-Dimethyl-2-(2-morpholin-4-yl-2-oxo-ethyl)-hexanoic acid [2-(5-methyl-isoxazol-3-ylamino)-ethyl]-amide;
50. 2-(R)-Cyclohexylmethyl-4-(cis-2,6-dimethyl-morpholin-4-yl)-N-[1-(S)-methyl-2-(4-trifluoromethoxy-phenylamino)-ethyl]-4-oxo-butyramide;
51. 2-(R)-Cyclohexylmethyl-N-[1-(S)-methyl-2-(4-trifluoromethoxy-phenylamino)-ethyl]-4-oxo-4-thiomorpholin-4-yl-butyramide;
52. 4-(4-Acetyl-piperazin-1-yl)-2-(R)-cyclohexylmethyl-N-[1-(S)-methyl-2-(4-trifluoromethoxy-phenylamino)-ethyl]-4-oxo-butyramide;
53. 2-(S)-(4-Methoxy-phenyl)-N-{2-methyl-1-(S)-[(4-trifluoromethoxy-phenylamino)-methyl]-propyl}-4-morpholin-4-yl-4-oxo-butyramide;
54. 2-(R)-Cyclohexylmethyl-N-[2-(5-fluoro-3,3-dimethyl-2,3-dihydro-indol-1-yl)-1-(S)-methyl-ethyl]-4-morpholin-4-yl-4-oxo-butyramide;
55. N-{2-Methyl-1-(S)-[(4-trifluoromethoxy-phenylamino)-methyl]-propyl}-4-morpholin-4-yl-4-oxo-2-(S)-(4-trifluoromethyl-phenyl)-butyramide;
56. -{2-Methyl-1-(S)-[(4-trifluoromethoxy-phenylamino)-methyl]-propyl}-4-morpholin-4-yl-4-oxo-2-(R)-(4-trifluoromethyl-phenyl)-butyramide;
57. N-{2-Methyl-1-(S)-[(4-trifluoromethoxy-phenylamino)-methyl]-propyl}-4-morpholin-4-yl-4-oxo-2-(S)-p-tolyl-butyramide;
58. 2-(R)-Cyclohexylmethyl-4-(1,1-dioxo-thiomorpholin-4-yl)-N-[1-(S)-methyl-2-(4-trifluoromethoxy-phenylamino)-ethyl]-4-oxo-butyramide;
59. 2-(R)-(3-Ethyl-3-hydroxy-cyclohexylmethyl)-N-[1-(S)-methyl-2-(4-trifluoromethoxy-phenylamino)-ethyl]-4-morpholin-4-yl-4-oxo-butyramide;
60. N-[1-(S)-Methyl-2-(4-trifluoromethoxy-phenylamino)-ethyl]-4-morpholin-4-yl-4-oxo-2-(S)-(4-trifluoromethyl-phenyl)-butyramide;
61. N-[1-(S)-Methyl-2-(4-trifluoromethoxy-phenylamino)-ethyl]-4-morpholin-4-yl-4-oxo-2-(S)-phenyl-butyramide;
62. 2-(S)-(4-Fluoro-phenyl)-N-[1-(S)-methyl-2-(4-trifluoromethoxy-phenylamino)-ethyl]-4-morpholin-4-yl-4-oxo-butyramide;
63. 2-(S)-(4-Methoxy-phenyl)-N-[1-(S)-methyl-2-(4-trifluoromethoxy-phenylamino)-ethyl]-4-morpholin-4-yl-4-oxo-butyramide;
64. 2-(S)-(4-Fluoro-phenyl)-N-{1-(S)-[(6-methoxy-pyridin-3-ylamino)-methyl]-2-methyl-propyl}-4-morpholin-4-yl-4-oxo-butyramide;
65. N-[1-(S)-Methyl-2-(4-trifluoromethoxy-phenylamino)-ethyl]-4-morpholin-4-yl-4-oxo-2-(R)-spiro[2.5]oct-6-yl-methyl-butyramide;
66. N-[2-(5-Fluoro-3,3-dimethyl-2,3-dihydro-indol-1-yl)-1-(S)-methyl-ethyl]-4-morpholin-4-yl-4-oxo-2-(S)-(4-trifluoromethyl-phenyl)-butyramide;
67. 2-(S)-(4-Fluoro-phenyl)-N-{1-(S)-[(3-methanesulfonyl-phenylamino)-methyl]-2-methyl-propyl}-4-morpholin-4-yl-4-oxo-butyramide;
68. N-[1-(S)-(5-Fluoro-3,3-dimethyl-2,3-dihydro-indol-1-ylmethyl)-2-methyl-propyl]-4-morpholin-4-yl-4-oxo-2-(S)-(4-trifluoromethyl-phenyl)-butyramide;
69. N-[1-(S)-Cyclopropyl-2-(5-fluoro-3,3-dimethyl-2,3-dihydro-indol-1-yl)-ethyl]-4-morpholin-4-yl-4-oxo-2-(S)-(4-trifluoromethyl-phenyl)-butyramide;
70. N-[1-(S)-Cyclopropyl-2-(4-trifluoromethoxy-phenylamino)-ethyl]-4-morpholin-4-yl-4-oxo-2-(S)-(4-trifluoromethyl-phenyl)-butyramide;
71. 2-(R)-(4-methanesulfonyl-phenyl)-N-{2-methyl-1-(S)-[(4-trifluoromethoxy-phenylamino)-methyl]-propyl}-4-morpholin-4-yl-4-oxo-butyramide;
72. (S,S)-Morpholine-4-carboxylic acid {2-cyclohexyl-1-[2-(4-methoxy-phenylamino)-1-methyl-ethylcarbamoyl]-ethyl}-amide;
73. Morpholine-4-carboxylic acid {2-cyclopentyl-1-(S)-[2-(4-methoxy-phenylamino)-1-(S)-methyl-ethylcarbamoyl]-ethyl}-amide;
74. Morpholine-4-carboxylic acid (2-cyclohexyl-1-(S)-{3-methanesulfonyl-1-(S)-[(4-trifluoromethoxy-phenylamino)-methyl]-propylcarbamoyl}-ethyl)-amide;
75. Morpholine-4-carboxylic acid (2-cyclohexyl-1(S)-{1-(S)-[(4-trifluoromethoxy-phenylamino)-methyl]-propylcarbamoyl}-ethyl)-amide;
76. Morpholine-4-carboxylic acid {2-cyclohexyl-1-(S)-[2-methyl-1-(S)-(pyridin-3-ylaminomethyl)-propylcarbamoyl]-ethyl}-amide;
77. Morpholine-4-carboxylic acid {2-cyclohexyl-1-(S)-[1-(S)-methyl-2-(5-methyl-isoxazol-3-ylamino)-ethylcarbamoyl]-ethyl}-amide;
78. Morpholine-4-carboxylic acid {1-(S)-[2-(benzothiazol-2-ylamino)-1-(S)-methyl-ethylcarbamoyl]-2-cyclohexyl-ethyl}-amide;
79. Morpholine-4-carboxylic acid {1-(S)-[2-(benzooxazol-2-ylamino)-1-(S)-methyl-ethylcarbamoyl]-2-cyclohexyl-ethyl}-amide;
80. (S,S)-Morpholine-4-carboxylic acid {2-cyclohexyl-1-[2-(5-fluoro-3,3-dimethyl-2,3-dihydro-indol-1-yl)-1-methyl-ethylcarbamoyl]-ethyl}-amide;
81. Morpholine-4-carboxylic acid {2-cyclohexyl-1-(S)-[1-(S)-cyclopropyl-2-(5-fluoro-3,3-dimethyl-2,3-dihydro-indol-1-yl)-ethylcarbamoyl]-ethyl}-amide;
82. Morpholine-4-carboxylic acid {2-cyclohexyl-1-(S)-[1-(S)-cyclopropyl-2-(5-fluoro-3,3-spirocyclopropyl-2,3-dihydro-indol-1-yl)-ethylcarbamoyl]-ethyl}-amide;
83. [1-(S)-Methyl-2-(4-trifluoromethoxy-phenylamino)-ethyl]-carbamic acid 1-(S)-cyclohexylmethyl-2-morpholin-4-yl-2-oxo-ethyl ester;
84. [1-(S)-Methyl-2-(4-trifluoromethoxy-phenylamino)-ethyl]-carbamic acid 3,3-dimethyl-1-(S)-(morpholine-4-carbonyl)-butyl ester;
85. [2-(4-Difluoromethoxy-phenylamino)-1-(S)-methyl-ethyl]-carbamic acid 3,3-dimethyl-1-(S)-(morpholine-4-carbonyl)-butyl ester;

86. {2-Methyl-1-(S)-[(4-trifluoromethoxy-phenylamino)-methyl]-propyl}-carbamic acid 1-(S)-cyclohexylmethyl-2-morpholin-4-yl-2-oxo-ethyl ester;
87. {3-Phenyl-1-(S)-[(4-trifluoromethoxy-phenylamino)-methyl]-propyl}-carbamic acid 1-(S)-cyclohexylmethyl-2-morpholin-4-yl-2-oxo-ethyl ester;
88. {1-(S)-[(4-Trifluoromethoxy-phenylamino)-methyl]-butyl}-carbamic acid 1-(S)-cyclohexylmethyl-2-morpholin-4-yl-2-oxo-ethyl ester;
89. [2-(4-Acetylsulfamoyl-phenylamino)-1-(S)-methyl-ethyl]-carbamic acid 1-(S)-cyclohexylmethyl-2-morpholin-4-yl-2-oxo-ethyl ester;
90. [2-(5-Fluoro-2,2-dimethyl-2,3-dihydro-indol-1-yl)-1-(S)-methyl-ethyl]-carbamic acid 1-(S)-cyclohexylmethyl-2-morpholin-4-yl-2-oxo-ethyl ester;
91. [1-(S)-Methyl-2-(5-methyl-isoxazol-3-ylamino)-ethyl]-carbamic acid 1-(S)-cyclohexylmethyl-2-morpholin-4-yl-2-oxo-ethyl ester;
92. (S,S)-[1-(5-Fluoro-3,3-dimethyl-2,3-dihydro-indol-1-yl-methyl)-propyl]-carbamic acid 1-cyclohexylmethyl-2-morpholin-4-yl-2-oxo-ethyl ester;
93. [2-(5-Fluoro-2,2-dimethyl-2,3-dihydro-indol-1-yl)-1-(S)-methyl-ethyl]-carbamic acid 1-(S)-cyclohexylmethyl-2-(2,6-cis-dimethyl-morpholin-4-yl)-2-oxo-ethyl ester;
94. (S,S)-[2-(5-Fluoro-2,2-dimethyl-2,3-dihydro-indol-1-yl)-1-methyl-ethyl]-carbamic acid 2-(4-acetyl-piperazin-1-yl)-1-cyclohexylmethyl-2-oxo-ethyl ester;
95. [2-(5-Fluoro-2,2-dimethyl-2,3-dihydro-indol-1-yl)-1-(S)-methyl-ethyl]-carbamic acid 1-(S)-cyclohexylmethyl-2-(4-methanesulfonyl-piperazin-1-yl)-2-oxo-ethyl ester;
96. [2-(5-Fluoro-2,2-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester;
97. [2-(5-Fluoro-3,3-dimethyl-2,3-dihydro-indol-1-yl)-1-(S)-methyl-ethyl]-carbamic acid 1-(S)-cyclohexylmethyl-2-(2,6-cis-dimethyl-morpholin-4-yl)-2-oxo-ethyl ester;
98. [2-(5-Fluoro-3,3-dimethyl-2,3-dihydro-indol-1-yl)-1-(S)-methyl-ethyl]-carbamic acid 2-(4-acetyl-piperazin-1-yl)-1-(S)-cyclohexylmethyl-2-oxo-ethyl ester;
99. [2-(5-Fluoro-3,3-dimethyl-2,3-dihydro-indol-1-yl)-1-(S)-methyl-ethyl]-carbamic acid 1-(S)-cyclohexylmethyl-2-(4-methanesulfonyl-piperazin-1-yl)-2-oxo-ethyl ester;
100. [2-(5-Fluoro-3,3-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester;
101. [2-(5-Fluoro-3,3-spiro-cylopropyl-2,3-dihydro-indol-1-yl)-1-(S)-methyl-ethyl]-carbamic acid 1-(S)-cyclohexylmethyl-2-morpholin-4-yl-2-oxo-ethyl ester;
102. [2-(5-Fluoro-3,3-dimethyl-2,3-dihydro-indol-1-yl)-1-(S)-methyl-ethyl]-carbamic acid 1-(S)-cyclohexylmethyl-2-oxo-2-piperidin-1-yl-ethyl ester;
103. [2-(5-Fluoro-3,3-dimethyl-2,3-dihydro-indol-1-yl)-1-(S)-methyl-ethyl]-carbamic acid 1-(S)-cyclohexylmethyl-2-oxo-2-pyrrolidin-1-yl-ethyl ester;
104. [2-(5-Fluoro-3,3-dimethyl-2,3-dihydro-indol-1-yl)-1-(S)-methyl-ethyl]-carbamic acid 2-cyclohexyl-1-(S)-dimethylcarbamoyl-ethyl ester;
105. [2-(5-Fluoro-3,3-dimethyl-2,3-dihydro-indol-1-yl)-1-(S)-methyl-ethyl]-carbamic acid 1-(S)-cyclohexylmethyl-2-(1,1-dioxo-1$\lambda^6$-thiomorpholin-4-yl)-2-oxo-ethyl ester;
106. [2-(5-Fluoro-3,3-dimethyl-2,3-dihydro-indol-1-yl)-1-(S)-methyl-ethyl]-carbamic acid 2-cyclohexyl-1-(S)-[(2-methoxy-ethyl)-methyl-carbamoyl]-ethyl ester;
107. [2-(5-Fluoro-3,3-dimethyl-2,3-dihydro-indol-1-yl)-1-(S)-methyl-ethyl]-carbamic acid 2-azetidin-1-yl-1-(S)-cyclohexylmethyl-2-oxo-ethyl ester;
108. [1-(S)-Cyclopropyl-2-(5-fluoro-3,3-dimethyl-2,3-dihydro-indol-1-yl)-ethyl]-carbamic acid 1-(S)-cyclohexylmethyl-2-morpholin-4-yl-2-oxo-ethyl ester;
109. [1-(S)-(5-Fluoro-3,3-dimethyl-2,3-dihydro-indol-1-ylmethyl)-2-methyl-propyl]-carbamic acid 2-morpholin-4-yl-2-oxo-1-(R,S)-phenyl-ethyl ester;
110. [1-(S)-(5-Fluoro-3,3-dimethyl-2,3-dihydro-indol-1-ylmethyl)-2-methyl-propyl]-carbamic acid 2-morpholin-4-yl-2-oxo-1-(R)-phenylmethanesulfonylmethyl-ethyl ester;
111. [1-(S)-(5-Fluoro-3,3-dimethyl-2,3-dihydro-indol-1-ylmethyl)-2-methyl-propyl]-carbamic acid 1-(S)-cyclohexyl-2-morpholin-4-yl-2-oxo-ethyl ester.

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$-$C_4$) alkane carboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example, glycolic, lactic, malic, tartaric or citric acid, such as amino acids, for example, aspartic or glutamic acid, or with organic sulfonic acids, such as ($C_1$-$C_4$)-alkylsuflonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W and X. In a more preferred aspect, the present invention provides compounds which selectively inhibit cathepsin S in the presence of cathepsin K, L, B, or combinations thereof.

Compounds of the present invention useful for treating cathepsin S dependent conditions, preferably have cathepsin S inhibition constants less than 10 µM. More preferably, compounds of the present invention useful for treating cathepsin S dependent conditions have cathepsin S inhibition constants of less than 1.0 µM. Most preferably, compounds of the present invention useful for treating cathepsin S dependent conditions have cathepsin S inhibition constants of less than 0.1 µM.

In a preferred aspect, compounds of the present invention that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular chronic neuropathic pain (see, WO 03/020287), Alzheimer's disease and certain autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In a preferred aspect, the pharmaceutical composition of the present invention provides a compound according to Formula I.

In one aspect of the present invention, compositions of the present invention that comprise compounds of the present invention and pharmaceutically acceptable excipients, selectively inhibit cathepsin S in the presence of other cathepsin isozymes. In a more preferred aspect, the present invention provides compositions which selectively inhibit cathepsin S in the presence of cathepsin K, L, B, or combinations thereof.

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in vitro and in vivo pharmacological tests generally known in the art, and as illustrated herein.

The above cited properties are demonstrable in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et al., *J. Rheumatology* 1993, 20, 1176). The efficacy of the compounds of the present invention for the treatment of osteoarthritis can be determined using models such as, or similar to, the rabbit partial lateral meniscectomy model, as described previously (Colombo et al., *Arth. Rheum.* 1993, 26, 875-886). The efficacy of the compounds in the model can be quantified using histological scoring methods, as described previously (O'Byrne et al., *Inflamm. Res.* 1995, 44, S 177-S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I.

Methods of the present invention useful for treating cathepsin S dependent conditions, preferably use compounds that have cathepsin S inhibition constants less than 10 µM. More preferably, methods of the present invention useful for treating cathepsin S dependent conditions use compounds that have cathepsin S inhibition constants of less than 1.0 µM. Most preferably, methods of the present invention useful for treating cathepsin S dependent conditions use compounds that have cathepsin S inhibition constants of less than 0.1 µM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W and X. In a more preferred aspect, methods of the present invention use compounds that selectively inhibit cathepsin S in the presence of cathepsin K, L, B, or combinations thereof.

In a preferred aspect, methods of the present invention use compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

VI. EXAMPLES

A. Compounds

General Procedure. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard.

Reference 1

Synthesis of
(S)-2-(4-Methoxy-phenylamino)-1-methyl ethyl amine

Step A: Preparation of (S)-2-(tert-Butoxycarbonylamino)-propionaldehyde. (S)-(−)-2-(tert-Butoxycarbonylamino)-1-propanol (523 mg, 2.98 mmol, 1.0 equiv.) was dissolved in 45 mL methylene chloride in a 100 mL r.b. flask with a magnetic stir bar. To this clear homogeneous solution, Dess-Martin periodinane (1.523 g, 3.591 mmol, 1.2 equiv.) was added in one portion and the cloudy white reaction mixture was allowed to stir at room temperature for 2 h. Thin-layer chromotography monitored the reaction to completion. The reaction mixture was diluted with 100 mL ethyl acetate. Sodium bisulfite solution (2 M, 20 mL) was added to the reaction mixture and the organic layer was separated. The aqueous layer was washed with 3×30 mL EtOAc. The combined organic layers were washed with 50 mL 1 M NaOH, followed by saturated NaCl (30 mL) and dried over $MgSO_4$. Filtration and rotary evaporation produced the desired product as a yellow oil (475 mg, 92% yield, $R_f$=0.63, 1:1 hexanes/ethyl acetate).

Step B: Preparation of [2-(4-methoxy-phenylamino)-(1S)-methyl-ethyl]-carbamic acid tert-butyl ester.

(S)-2-(tert-Butoxycarbonylamino)-propionaldehyde (473 mg, 2.74 mmol) and p-anisidine (1.031 g, 8.371 mmol, 3.0 equiv.) was dissolved in 45 mL of MeOH at 0° C. in a 100 mL r.b. flask with a magnetic stir bar. Optionally, acetic acid (469 μL, 8.21 mmol, 3.0 equiv.) can be added via syringe to assist in the reaction. To the stirring dark colored solution was added sodium cyanoborohydride (326 mg, 5.82 mmol, 1.89 equiv.). Gas evolution and disappearance of color were observed. The reaction was allowed to slowly warm to room temperature with stirring over 30 minutes and the reaction was monitored by LC/MS. At the completion of the reaction, the mixture was quenched with 1 M NaOH, and extracted 3×50 mL ethyl acetate. The resulting organics were washed with 50 mL saturated $NaHCO_3$, 40 mL saturated NaCl, and dried over $MgSO_4$. Evaporation of ethyl acetate provided 728 mg of a brown oil. Purification by automated ISCO chromatography provided a clear oil of [2-(4-methoxy-phenylamino)-(1S)-methyl-ethyl]-carbamic acid tert-butyl ester (583 mg, 2.079 mmol, 76% yield). HPLC-MS calcd. for $C_{15}H_{24}N_2O_3$ $(M+H^+)$ 281.2, found 281.5. $^1H$ NMR ($CDCl_3$, 400 MHz) δ 1.21 (d, 6H, J=6.6 Hz), 1.47 (s, 9H), 3.05 (dd, 1H, J=12.2, 7.3 Hz), 3.13 (dd, 1H, J=12.2, 4.6 Hz), 3.76 (s, 3H), 3.93 (broad s, 1H), 4.62 (broad s, 1H), 6.60 (d, 2H, J=6.8 Hz), 6.80 (2H, d, J=6.8 Hz).

Step C: [2-(4-Methoxy-phenylamino)-(1S)-methyl-ethyl]-carbamic acid tert-butyl ester (383 mg, 1.37 mmol) was added to 10 mL of a trifluoroacetic acid solution (10 v/v % in methylene chloride) at room temperature in a 25 mL r.b. flask with a magnetic stirbar. The reaction turns dark purple/black in color after 5 minutes. The reaction is allowed to stir at room temperature until the reaction is judged complete by HPLC/MS. The solvent is removed by evaporation and to provide 2-(4-Methoxy-phenylamino)-(1S)-methyl-ethyl-ammonium; trifluoro-acetate salt as a brown oil (394 mg, 1.34 mmol, 98% yield) and used directly in the next reaction. HPLC-MS calcd. for $C_{10}H_{16}N_2O$ $(M+H^+)$ 181.1, found 181.5.

Reference 2

(R)-3-Benzyloxy-$N^1$-(4-methoxy-phenyl)-propane-1,2-diamine

Step A: N-Boc-OBn-Serine (750 mg, 2.54 mmol), p-anisidine (344 mg, 2.79 mmol) and HOBt (377 mg, 2.79 mmol) were charged to a 50 mL roundbottom flask and treated with $CH_2Cl_2$ (6 mL). The reaction was then treated with EDCI (535 mg, 2.79 mmol) and allowed to stir for 2 hours. The reaction was then diluted with ethyl acetate and extracted twice with water, twice with 1 M HCl and twice with 1 M NaOH. The organics were then dried over $MgSO_4$ and the solvent was removed to afford 450 mg (44%) of a white solid: $^1H$ NMR ($CDCl_3$, 400 MHz) δ 1.49 (s, 9H), 3.63-3.72 (m, 1H), 3.81 (s, 3H), 4.00-4.08 (m, 1H), 4.47-4.50 (m, 1H), 4.55-4.70 (m, 2H), 5.45-5.60 (m, 1H), 6.87 (d, 2H, J=8.8), 7.30-7.41 (m, 7H), 8.20-8.33 (m, 1H); HPLC-MS calcd. for $C_{22}H_{28}N_2O_5$ $(M+H^+)$ 401.2, found 401.4.

Step B: The product from Step A (400 mg, 1.00 mmol) was added to an ice cold solution of borane (1 M) in THF. The cooling bath was removed and the reaction was allowed to stir for 24 h at which point the excess reagent was quenched using 5% $NaHSO_4$. The reaction was diluted with ethyl acetate and extracted twice with 1 M NaOH. The organics were dried over $MgSO_4$ and the solvent was removed. The resulting residue contained material that was missing the Boc group and some material that still had it (by HPLC-MS). The oil was treated with MeOH (2 mL) and 4 M HCl (2 mL) and stirred for 3 hours. The solvent was then removed and the reaction was partitioned between ethyl acetate and 1 M NaOH. The aqueous phase was extracted twice more with ethyl acetate and the combined organics were dried over $MgSO_4$ and the solvent was removed.

Reference 3

Synthesis of (S)—N1-(4-trifluoromethoxy-phenyl)-propane-1,2-diamine

Step A: (S)-2-(benzylcarbonylamino)-propionaldehyde.

(S)-2-(benzylcarbonylamino)-propanol (5 g, 23.9 mmol) was dissolved in $CH_2Cl_2$ (200 mL) and treated with Dess-Martin periodinane (12.26 g, 1.1 eq). The mixture was stirred for 2 hours, then quenched with sodium thiosulphate, and the solvent removed in vacuo. The residue was then separated between sodium hydroxide (1M, 500 mL) and ethyl acetate (500 mL). The organics were washed with brine, dried ($MgSO_4$) and evaporated in vacuo to yield a clear oil which was used immediately in the next step without further purification.

Step B: [1-(S)-Methyl-2-(4-trifluoromethoxy-phenylamino)-ethyl]-carbamic acid benzyl ester.

(S)-2-(benzylcarbonylamino)-propionaldehyde was dissolved in methanol (300 mL). Acetic acid (4 mL, 2.9 eq) was added and the mixture treated with 4-trifluoromethoxy aniline (9.6 mL, 3 eq) and stirred for 15 minutes then sodium cyanoborohydride (4.36 g, 2.9 eq) was added with some effervescence. The mixture was stirred for 3 hours, and then the solvent reduced in vacuo. This was then separated between hydrochloric acid (1M, 500 mL×2) and ethyl acetate (500 mL). The organics were washed with sodium bicarbonate (500 mL), brine (500 mL), dried ($MgSO_4$) and evaporated in vacuo to give a clear oil which was purified by silica gel chromatography eluted with a gradient of 0-100% ethyl acetate/hexane.

Step C: (S)—N1-(4-Trifluoromethoxy-phenyl)-propane-1,2-diamine.

[1-(S)-Methyl-2-(4-trifluoromethoxy-phenylamino)-ethyl]-carbamic acid benzyl ester (23.9 mmol) was dissolved in ethanol (200 mL) then placed under nitrogen. 10% Palladium on carbon was added (0.5 g) and the mixture was stirred under hydrogen (atmospheric pressure) overnight. When reaction was complete, the mixture was filtered through celite. The celite was washed with ethanol (5×50 ml) then evaporated in vacuo to give a brown oil (4.03 g, 17.21 mmol, 72% yield over 3 steps).

Reference 4

Synthesis of 2,2-dimethyl-5-fluoroindoline

Step A: A solution of N-Boc-4-fluoroaniline (9.02 g, 42.7 mmol) in THF (112 mL) was cooled to −60° C. using a cryocool instrument. The solution was treated with 1.7 M t-BuLi in pentane (63 mL, 106.7 mmol) dropwise. After the first equivalent of base was consumed, a yellow solution formed. The reaction was allowed to warm to −20° C. and was stirred at that temperature for 2.5 hours. The reaction was then treated with a solution of methallyl bromide (5.67 g, 42.7 mmol) in THF (35 mL) dropwise and stirred for an additional 1.5 hours at −20° C. The reaction was then quenched by addition of water. After coming to room temperature, the reaction was treated with ethyl acetate and extracted with water and brine, dried over $MgSO_4$ and filtered. The solvent was then removed and the residue was purified on silica gel using a gradient of 0-25% ethyl acetate in hexane to afford 11.3 g (80% yield) of [4-Fluoro-2-(2-methyl-allyl)-phenyl]-carbamic acid tert-butyl ester as a white solid; $^1H$ NMR ($CDCl_3$, 400 MHz) δ 1.50 (s, 9H), 1.72 (s, 3H), 3.28 (s, 2H), 4.71 (s, 1H), 4.92 (s, 1H), 6.32-6.50 (m, 1H), 6.86 (dd, 1H, $J_1$=3.0, $J_2$=9.1), 6.93 (ddd, 1H, $J_1$=3.0, $J_2$=8.5, $J_3$=11.5), 7.65-7.82 (m, 1H); HPLC-MS calcd. for $C_{15}H_{20}FNO_2$ (M+H$^+$-tBu) 210.1, found 210.3.

Step B: A sample of [4-Fluoro-2-(2-methyl-allyl)-phenyl]-carbamic acid tert-butyl ester (1.10 g, 4.14 mmol) was treated with anisole (5 mL), dichloromethane (5 mL) and trifluoroacetic acid (5 mL) and stirred for 4 hours. The solvent was removed and the reaction was transferred to a microwave reaction vial using methanesulfonic acid (3 mL). The reaction was heated to 170° C. for 10 minutes. The reaction was cooled to room temperature and quenched into excess stirring 1 M NaOH. The aqueous phase was extracted twice with ethyl acetate and the combined organics were dried over $MgSO_4$ and filtered. The resulting oil was purified on silica gel using a gradient of 0-70% t-butyl ethyl ether and hexane to afford 450 mg (66% yield) of 2,2-dimethyl-5-fluoroindoline; $^1H$ NMR ($CDCl_3$, 400 MHz) δ 1.08 (s, 6H), 2.58 (s, 2H), 6.24 (dd, 1H, $J_1$=4.4, $J_2$=8.4), 6.43-6.48 (m, 1H), 6.53-6.56 (m, 1H); HPLC-MS calcd. for $C_{10}H_{12}FN$ (M+H$^+$) 166.1, found 166.4.

Reference 5

Synthesis of 3,3-dimethyl-5-fluoroindoline

According to the procedure described in S. Coulton et al. WO9925709 with the following modifications. N-(4-Fluoro-phenyl)-N-(2-methyl-allyl)-acetamide (5 grams, 24.12 mmol) was added to a microwave tube with aluminum trichloride (7 grams, 52.4 mmol). The tube was capped and heated to 150° C. for 20 minutes under microwave. The slurry was worked up with water and ethyl acetate, the organic layer was extracted with 3 washes of saturated sodium bicarbonate solution and the organic layer was dried over magnesium sulfate. The solution was then filtered and rotary evaporated to yield pure 1-(5-Fluoro-3,3-dimethyl-2,3-dihydro-indol-1-yl)-ethanone in quantitative yield. This was converted to the free indoline by suspending the entire 5 grams of product in 20 mL of 6 M HCl and heating in a microwave to 200° C. for 10 minutes. The resulting 5-Fluoro-3,3-dimethyl-2,3-dihydro-1H-indole crystallized on cooling as the hydrochloride salt in quantitative yield. This material was identical to the previously reported compound.

Reference 6

Synthesis of (S)-[1-Cyclopropyl-2-(5-fluoro-3,3-dimethyl-2,3-dihydro-indol-1-yl)-ethyl]-carbamic acid benzyl ester Step A: (S)-cyclopropyl glycine was prepared according to a modified procedure from that reported in D. J. Bayston et al. U.S. Pat. No. 6,191,306. A sample of (R)-phenethyl-(S)-cyclopropyl glycine (16.8 g, 76.7 mmol) was treated with THF (200 mL), water (100 mL) and 10% Pd/C (4.76 g). To the stirring mixture was added formic acid (17 mL) and the reaction was stirred overnight. The catalyst was then removed by filtration through a pad of celite and the solvent was removed by rotary evaporation. The material was co-evaporated with methanol several times and dried under vacuum to afford 4.75 g (54% yield) of the desired material as a solid which was used without further purification.

The material from the previous step (4.75 g, 41 mmol) was dissolved in 130 mL of 1 N NaOH and treated with benzyl chloroformate (5.92 g, 49.5 mmol) with vigorous stirring. The reaction was stirred overnight and then extracted with dichloromethane twice. The organics were discarded and the aqueous phase was acidified with conc. HCl and extracted with dichloromethane three times. The combined organics were dried over $MgSO_4$ and the solvent was removed to afford 7.38 g (72% yield) of the (S)-benzyloxycarbonylamino-cyclopropyl-acetic acid as a white solid.

Step B: A solution of (S)-benzyloxycarbonylamino-cyclopropyl-acetic acid (3.2 g, 12.8 mmol) in THF (20 mL) was cooled in an ice/water bath and treated with a 1 M solution of $BH_3$ in THF (16.7 mL, 16.7 mmol). The reaction was stirred for 4 hours and then treated with 1 M HCl until the bubbling ceased. The reaction was stirred overnight and the organic solvent was removed by rotary evaporation. The residue was treated with ethyl acetate and transferred to a separatory funnel. The aqueous phase was discarded and the organics were washed twice with 1 M NaOH, dried over $MgSO_4$ and the solvent was removed. The residue was purified on silica gel using a gradient of 0-100% ethyl acetate in hexane to afford 1.5 g (50% yield) of (S)-(1-Cyclopropyl-2-hydroxy-ethyl)-carbamic acid benzyl ester as a white solid; $^1H$ NMR ($CDCl_3$, 400 MHz) δ 0.26-0.37 (m, 1H), 0.34-0.44 (m, 1H), 0.47-0.61 (m, 2H), 0.83-0.94 (m, 1H), 2.95-3.04 (m, 1H), 3.70 (dd, 1H, $J_1$=5.8, $J_2$=11.1), 3.79-3.88 (m, 1H), 5.00-5.12 (m, 1H), 5.10 (s, 2H), 7.29-7.31 (m, 5H); HPLC-MS calcd. for $C_{13}H_{17}NO_3$ (M+H$^+$) 236.1, found 236.3.

Step C: (S)-[1-Cyclopropyl-2-(5-fluoro-3,3-dimethyl-2,3-dihydro-indol-1-yl)-ethyl]-carbamic acid benzyl ester was prepared in 67% yield an analogous manner to reference 3 except that the alcohol from the previous step and 1 equivalent of 3,3-dimethyl-5-fluoroindoline (WO 9925709) were used as coupling partners; HPLC-MS calcd. for $C_{23}H_{27}FN_2O_2$ (M+H$^+$) 383.2, found 383.4.

Reference 7

Synthesis of 5-fluoro-3,3-spirocyclopropyl-indoline

Step A: A solution of 5-fluoroisatin (5 g, 30.2 mmol) in DMF (60 mL) was cooled in an ice/water bath and treated with sodium hydride (1.44 g, 60.6 mmol) portionwise. The reaction was stirred for 15 minutes after the addition of the last portion and then treated with p-methoxybenzyl chloride (5.32 g, 45.3 mmol) and allowed to stir for 1 hour. The reaction was then quenched by slow addition of excess methanol. After bubbling had stopped, the reaction was poured into water (100 mL) and extracted twice with ethyl acetate. The organics were combined, dried over $MgSO_4$ and the solvent was removed. The residue was purified by silica gel chromatography using a gradient of 0-100% ethyl acetate in hexane to afford 7.1 g (82%) of 5-Fluoro-1-(4-methoxybenzyl)-1H-indole-2,3-dione; $^1H$ NMR ($CDCl_3$, 400 MHz) δ 3.79 (s, 3H), 4.86 (s, 2H), 6.75 (dd, 1H, $J_1$=3.6, $J_2$=8.6), 6.84-6.90 (m, 2H), 7.19 (ddd, 1H, $J_1$=$J_2$=8.6, $J_3$=3.6), 7.22-7.27 (m, 1H), 7.26-7.31 (m, 2H); HPLC-MS calcd. for $C_{16}H_{12}FNO_3$ (M+H$^+$) 286.1, found 286.3.

Step B: A solution of 5-fluoro-1-(4-methoxy-benzyl)-1H-indole-2,3-dione (7.1 g, 24.9 mmol) in hydrazine hydrate (35 mL) and ethanol (15 mL) was refluxed overnight, diluted with water and extracted twice with ethyl acetate. The combined organics were dried over $Na_2SO_4$, filtered and concentrated. The residue was purified by silica gel chromatography using a gradient of 0-100% ethyl acetate in hexane to afford 6.1 g (90%) of 5-fluoro-1-(4-methoxy-benzyl)-1,3-dihydro-indol-2-one; $^1H$ NMR ($CDCl_3$, 400 MHz) δ 3.59 (s, 2H), 3.77 (s, 3H), 4.83 (s, 2H), 6.63 (dd, 1H, $J_1$=4.2, $J_2$=8.6), 6.82-6.91 (m, 3H), 6.96-7.01 (m, 1H), 7.19-7.23 (m, 1H), 7.27-7.31 (m, 1H); HPLC-MS calcd. for $C_{16}H_{14}FNO_2$ (M+H$^+$) 272.1, found 272.3.

Step C: A solution of 5-fluoro-1-(4-methoxy-benzyl)-1,3-dihydro-indol-2-one (6.12 g, 22.6 mmol) in DMF (65 mL) was cooled in an ice/water bath and treated with dibromoethane (6.35 g, 33.8 mmol) followed by sodium hydride (1.09 g, 45 mmol) portionwise. After stirring at 0° C. for 1 hour, the reaction was cooled to −78° C. and treated with excess methanol. After bubbling had stopped, the reaction was poured into water (100 mL) and extracted twice with ethyl acetate. The organics were combined, dried over $Na_2SO_4$ and the solvent was removed. The residue was purified by silica gel chromatography using a gradient of 0-100% ethyl acetate in hexane to afford 4.1 g (61%) of 5-fluoro-1-(4-methoxy-benzyl)-siprocyclopropyloxindole; $^1H$ NMR ($CDCl_3$, 400 MHz) δ 1.54 (dd, 2H, $J_1$=4.0, $J_2$=7.8), 1.83 (dd, 2H, $J_1$=4.3, $J_2$=8.1), 3.77 (s, 3H), 4.91 (s, 2H), 6.57 (dd, 1H, $J_1$=2.5, $J_2$=8.0), 6.69 (dd, 1H, $J_1$=4.2, $J_2$=8.5), 6.81 (dd, 1H, $J_1$=2.5, $J_2$=9.3), 6.83-6.87 (m, 2H), 7.22-7.25 (m, 2H); HPLC-MS calcd. for $C_{18}H_{16}FNO_2$ (M+H$^+$) 298.1, found 298.3.

Step D: A solution of 5-fluoro-1-(4-methoxy-benzyl)-siprocyclopropyloxindole (3.38 g, 11.4 mmol) in TFA (20 mL) was stirred at 60° C. overnight. The solvent was then removed and the reaction was diluted with ethyl acetate and washed with saturated aqueous $NaHCO_3$ until the washings were neutral. The organic phase was then washed with brine, dried over $Na_2SO_4$ and the solvent was removed. The residue was purified by silica gel chromatography using a gradient of 0-100% ethyl acetate in hexane to afford 1.94 g (96%) of 5-fluoro-siprocyclopropyloxindole; $^1H$ NMR (MeOD, 400 MHz) δ 1.76-1.86 (m, 4H), 6.91-6.94 (m, 1H), 7.07-7.11 (m, 2H); HPLC-MS calcd. for $C_{10}H_8FNO$ (M+H$^+$) 178.2, found 178.3.

Step E: A sample of 5-fluoro-siprocyclopropyloxindole (172 mg, 97 μmol) was cooled in an ice/water bath and treated with a 1.0 M solution of LAH (1.94 ml, 1.9 mmol). The reaction was stirred at room temperature for 15 minutes and then at 50° C. for 3 hours and finally was cooled back down with an ice/water bath. The reaction was treated with 1 M NaOH (1.9 mL) followed by water (1.9 mL). The reaction was filtered over celite and dried over $MgSO_4$. After filtration, the solvent was removed and the crude material of 5-fluoro-siprocyclopropylindoline was used without purification.

In addition, synthesis of other 3,3-spiro-cycloalkylindolines are also described in (1) Jackson, A. H. et al. Tetrahedron (1968), 24(1), 403-13; (2) Jansen, A. B. A. et al. Tetrahedron (1965), 21(6), 1327-31; (3) Bermudez, J. et al. J. Med. Chem. (1990), 33(7), 1929-32; (4) Nishio, T. et al. Helv. Chim. Acta (1990), 73(6), 1719-23; (5) Nishio, T. et al. J. Chem. Soc., Perkin Trans 1 (1991), (1), 141-3; (6) Kucerovy, A. et al. Synth. Commun. (1992), 22(5), 729-33; (7) Kato, M. et al. Chem. Pharm. Bull. (1995), 43(8), 1351-7.

Reference 8

Synthesis of 2,2,5-trifluoroindoline

Step A: 5-Fluoro-1H-indole-2,3-dione (956 mg, 5.79 mmol, 1 eq) was added as a solution in dry DMF to a stirred slurry of sodium hydride (278 mg, 11.6 mmol, 2 eq) in dry DMF drop wise over 15 minutes under an inert atmosphere with adequate pressure release to accommodate $H_2$ evolution. The resulting mixture was stirred for 1 hour and p-methoxybenzyl chloride was added via syringe to the reaction. The solution was then stirred ca 2 hours and worked up by addition of water followed by extraction into ethyl acetate. The organic layer was washed twice with water and then dried over $MgSO_4$. Column chromatography with ethyl acetate/hexane afforded 5-Fluoro-1-(4-methoxy-benzyl)-1H-indole-2,3-dione as a red solid (1.3 g, 80% yield). $^1H$ NMR ($CDCl_3$) δ (ppm): 7.3-7.24 (m, 3H), 7.20 (td, J=8.7, 2.7 Hz, 1H), 6.9-6.86 (m, 2H), 6.76 (dd, J=8.6, 3.6 Hz, 1H), 3.81 (s, 2H), 3.78 (s, 3H). LC/MS=286.1 (M+1).

Step B: The product from step A (200 mg, 0.701 mmol, 1 eq) was dissolved in 10 mL of dry DCM and placed under and inert atmosphere. DAST (339 mg, 2.103 mmol, 3 eq) was added via syringe and the reaction was stirred overnight. The reaction was worked up by addition of saturated aqueous sodium bicarbonate and the organic layer was dried over $MgSO_4$, filtered, and rotary evaporated to dryness. The resulting crude material was purified by flash chromatography using ethyl acetate/ hexane as a solvent system. $^1H$ NMR ($CDCl_3$) δ (ppm): 7.3-7.28 (m, 1H), 7.22 (d, J=8.7 Hz, 2H), 7.09 (td, J=8.7, 1.3 Hz, 1H), 6.87 (d, J=8.7 Hz, 2H), 6.73 (m, 1H), 4.83 (s, 2H), 3.79 (s, 3H). LC/MS=308.1 (M+1).

Step C: The product from step B (1.178 g, 3.83 mmol, 1 eq) was dissolved in 75 mL of dry THF and placed under an inert atmosphere. $LiAlH_4$ (291 mg, 7.66 mmol, 2 eq) was added as a solid under a positive pressure of $N_2$ at −78° C. The reaction was allowed to stir at this temperature for 30 min and then allowed to warm to room temp over a period of 6 hours. The reaction was worked up by addition of water dropwise followed by 4 equivalents of aqueous KOH. The slurry was diluted with 500 mL of water and extracted with 2×200 mL portions of ethyl acetate. The organic layers were combined, dried over $MgSO_4$, filtered, and rotary evaporated to dryness. The resulting crude material was purified by flash chromatography using ethyl acetate/ hexane as a solvent system yielding 320 mg of pure material (28%). $^1H$ NMR ($CD_3OD$) δ (ppm): 7.21 (d, J=8.8 Hz, 2H), 7.06 (dd, J=8.2, 1.3 Hz, 1H), 6.89 (m, 1H), 6.84 (d, J=8.7 Hz, 2H), 6.77 (dd, J=8.6, 4.3 Hz, 1H), 4.83 (s, 2H), 3.73 (s, 3H), 3.12 (s, 2H). LC/MS=294.1 (M+1).

Step D: The product from step C (50 mg, 0.1704 mmol, 1 eq) was taken up in 1 mL of TFA. The solution was placed in a microwave tube, sealed, and heated to 175° C. for 5 minutes. The resulting black solution was neutralized with saturated sodium bicarbonate and extracted with 2×50 mL portions of ethyl acetate. The organic layers were dried over $MgSO_4$, filtered, and rotary evaporated to dryness. The resulting solid was dissolved in a 50:50 mix of DMSO/ MeOH and purified by prep HPLC. Yield 23.8 mg of white solid (81%). $^1H$ NMR (DMSO D$_6$) δ (ppm): 10.41 (s, 1H), 7.13 (dd, J=8.6, 2.4 Hz, 1H), 7.01 (td, J=8.6, 2.7 Hz, 1H), 6.8 (dd, J=8.5, 4.5 Hz, 1H), 3.5 (s, 2H).

Example 1

Morpholine-4-carboxylic acid (S)-2-cyclohexyl-1-[2-(5-fluoro-2,3-dihydro-indol-1-yl)-ethylcarbamoyl]-ethyl ester

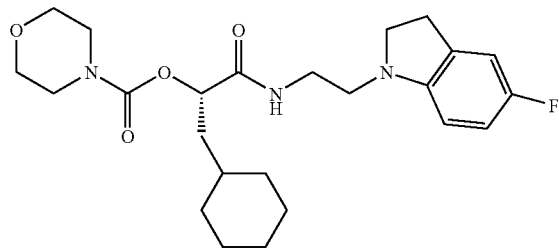

To a stirring suspension of L-cyclohexylalanine (4.00 g, 23.4 mmol) in 0.5M H$_2$SO$_4$ (120 mL) at 0° C. was slowly added dropwise an aqueous solution of NaNO$_2$ (12.1 g in 40 mL H$_2$O). Addition was complete after approximately 1 h, at which point the solution was allowed to warm to room temperature. After 16h, the reaction mixture was extracted with ether (3×100 mL), and the combined organic extracts were washed with 1M NaHSO$_4$ (1×200 mL) and brine (1×100 mL) and then dried over anhydrous Na$_2$SO$_4$. The solvent was removed in vacuo, and the crude product was recrystallized from Et$_2$O/pentane (10 mL/100 mL) to afford 2.1 g (52% yield) of (S)-cyclohexyl lactic acid as fine white needles.

To a stirring suspension of (S)-cyclohexyl lactic acid (558 mg, 3.42 mmol) in CH$_2$Cl$_2$ was added 2-(5-fluoro-2,3-dihydro-indol-1-yl)-ethylamine (616 mg, 3.42 mmol), HATU (1.429 g, 3.76 mmol), and DIEA (1.79 mL, 10.3 mmol). The reaction mixture was stirred at room temperature for several hours until the starting material had disappeared by LCMS. Ethyl acetate (100 mL) was added and the solution was washed with 1M NaHSO$_4$ (2×100 mL), sat'd aq NaHCO$_3$ (2×100 mL) and brine (1×100 mL). The solvent was removed in vacuo and the crude material was purified by silica gel chromatography (hexanes/EtOAc) to afford 320 mg of 3-Cyclohexyl-N-[2-(5-fluoro-2,3-dihydro-indol-1-yl)-ethyl]-2-(S)-hydroxy-propionamide as a white powder.

To a stirring solution of 3-Cyclohexyl-N-[2-(5-fluoro-2,3-dihydro-indol-1-yl)-ethyl]-2-(S)-hydroxy-propionamide (263 mg, 0.79 mmol) in CH$_2$Cl$_2$ (2.0 mL) was added pyridine (0.1 mL) and 4-nitrophenyl chloroformate (202 mg, 1.01 mmol). The reaction was stirred at room temperature overnight at which point the starting material had disappeared by LCMS. The crude material was purified by silica gel chromatography to afford the corresponding mixed carbonate as a white powder.

The resulting carbonate (50 mg, 0.094 mmol) was dissolved in CH$_2$Cl$_2$ (1.0 mL), excess morpholine (0.1 mL) was added and the reaction was stirred at room temperature for several until the starting material had disappeared by LCMS. The solvent was removed in vacuo and the crude material was purified by reverse phase HPLC. HPLC-MS calcd. for C$_{24}$H$_{34}$FN$_3$O$_4$ (M+H$^+$) 448.25, found 448.5.

Example 2

Morpholine-4-carboxylic acid {2-cyclohexyl-1-(S)-[2-(5-fluoro-2,3-dihydro-indol-1-yl)-ethylcarbamoyl]-ethyl}-amide

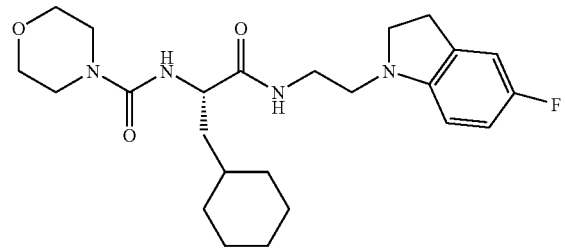

The title compound was synthesized according to the procedure outlined in Example 4 starting from 2-(5-Fluoro-2,3-dihydro-indol-1-yl)-ethylamine.

HPLC-MS calcd. for C$_{24}$H$_{35}$FN$_4$O$_3$ (M+H$^+$) 447.27, found 447.5.

Example 3

Morpholine-4-carboxylic acid {2-cyclohexyl-1-(S)-[2-(4-fluoro-phenylamino)-ethylcarbamoyl]-ethyl}-amide

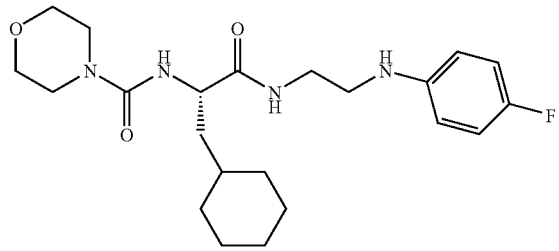

The title compound was synthesized according to the procedure outlined in Example 4 starting from N1-(4-fluorophenyl)-ethane-1,2-diamine.

HPLC-MS calcd. for C$_{22}$H$_{33}$FN$_4$O$_3$ (M+H$^+$) 421.25, found 421.5.

Example 4

Morpholine-4-carboxylic acid {2-cyclohexyl-1-(S)-[2-(4-methoxy-phenylamino)-ethylcarbamoyl]-ethyl}-amide

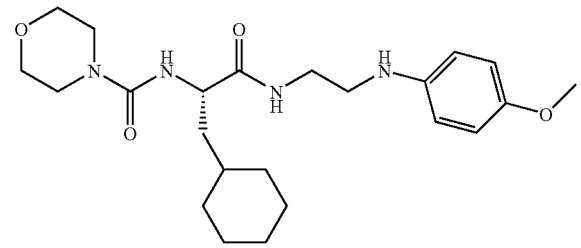

Step A: An aldehyde-functionalized polystyene resin ("Pal-Resin", 16.76 g @ 1.05 mmol/g, 17.6 mmol) was swelled in DMF (50 ml) for 10 min. N1-(4-Methoxy-phenyl)-ethane-1,2-diamine (5.85 g, 35 mmol, prepared according Scheme 1) in DMF (150 mL) was added followed by acetic acid (8.1 mL, 8 eq), and the mixture was agitated for 1 hour at room temperature. Sodium triacetoxyborohydride (11.2 g, 52.8 mmol eq.) is then added and the mixture was shaken for 16 hours at room temperature. The reductively aminated resin was then filtered and washed (DMF ×3, equal mixture of methanol/dichloromethane ×4, Acetonitrile ×3).

Step B: The resin (17.6 mmol) is swelled in dimethylformamide (50 mL) and a solution of Fmoc-CHA-OH (20.45 g, 3 eq), HOBt (8.08 g, 3 eq) and DIC (4.58 mL, 3 eq) was added. The mixture was shaken for 3 hours then washed (dimethylformamide ×3, equal mixture of methanol/dichloromethane ×4, Acetonitrile ×3).

Synthesis of final products is performed on an Argonaut Quest 210 with automated washing module performing washes automatically.

Step C: Fmoc Deprotection.

The resin (250 mg, 0.163 mmol) is weighed into reaction vessels followed by a stirrer bar then treated with piperidine in dimethylformamide (4 mL of a 20% solution) and the mixture agitated for one hour. The resin is then washed (3× dimethylformamide, 3× dichloromethane).

Step D: Urea Formation.

A solution morpholine carbonyl chloride (3 eq, 0.490 mmol) dissolved in dichloromethane (10 mL) was added to the resin (0.163 mmol). DIEA (3 eq, 0.490 mmol) was added, and the reaction is agitated for three hours then washed with dimethylformamide four times, dichloromethane four times, then dried with nitrogen.

Step E: Cleavage.

The resin is treated with a mixture of trifluoroacetic acid, dichloromethane and water (45:45: 10, 10 mL). It is agitated for one hour then retreated, agitated for five minutes, then washed one more time and filtered into vials. The solvent is evaporated in vacuo then purified using a Waters mass directed LCMS system (7.5 min method, gradient 10-90% acetonitrile/water with 0.35% trifluoroacetic acid). The compounds are then analyzed then concentrated to a solid via lyophilization.

HPLC-MS calcd. for $C_{23}H_{36}FN_4O_4$ (M+H$^+$) 433.27, found 433.5.

Example 5

[2-(4-Fluoro-phenylamino)-ethyl]-carbamic acid 1-(S)-cyclohexylmethyl-2-morpholin-4-yl-2-oxo-ethyl ester

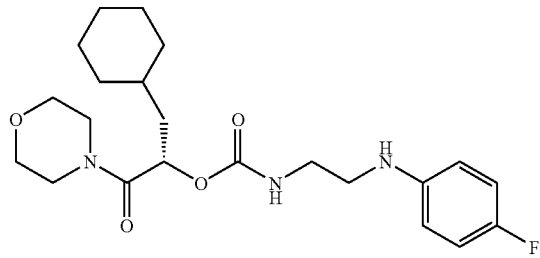

To a stirring suspension of L-cyclohexylalanine (4.00 g, 23.4 mmol) in 0.5M $H_2SO_4$ (120 mL) at 0° C. was slowly added dropwise an aqueous solution of $NaNO_2$ (12.1 g in 40 mL $H_2O$). Addition was complete after approximately 1 h, at which point the solution was allowed to warm to room temperature. After 16h, the reaction mixture was extracted with ether (3×100 mL), and the combined organic extracts were washed with 1M $NaHSO_4$ (1×200 mL) and brine (1×100 mL) and then dried over anhydrous $Na_2SO_4$. The solvent was removed in vacuo, and the crude product was recrystallized from $Et_2O$/pentane (10 mL/100 mL) to afford 2.1 g (52% yield) of (S)-cyclohexyl lactic acid as fine white needles.

To a stirring solution of (S)-cyclohexyl lactic acid (300 mg, 1.74 mmol), morpholine (0.15 mL, 1.74 mmol), and DIEA (0.91 mL, 5.23 mmol) in $CH_2Cl_2$ (3 mL) was added HATU (728 mmol, 1.92 mmol) and the reaction mixture was stirred at room temperature overnight. EtOAc (100 mL) was added and the solution was washed with sat'd $NaHCO_3$ (2×100 mL), brine (1×100 mL), dried over $Na_2SO_4$, and concentrated in vacuo to afford the corresponding amide as a colorless oil which was used without purification.

The resulting amide (1.74 mmol) was dissolved in pyridine (5 mL) and 4-nitrophenyl chloroformate (405 mg, 2.21 mmol) was added. The reaction mixture was stirred at 70° C. for 4 h at which point the starting material had disappeared by LCMS. The reaction was then cooled to room temperature, EtOAC (100 mL) was added, the organic layer was washed with 1M $NaHSO_4$, and dried over $Na_2SO_4$. The crude material was purified by silica gel chromatography (hexanes/EtOAc) to afford 550 mg (78% yield, over two steps) of the nitrophenyl carbonate as a white powder.

To a stirring suspension of N1-(4-fluorophenyl)-ethane-1, 2-diamine-2HCl (110 mg, 0.48 mmol) and DIEA (0.34 mL, 1.93 mmol) in THF (2.0 mL) was added nitrophenyl carbonate obtained in the last step (196 mg, 0.48 mmol). The reaction mixture was stirred at room temperature, and after 18h the starting material had disappeared by LCMS. Solvent was evaporated and the crude material was purified by silica gel chromatography (Hexanes/EtOAc) followed by a second purification by reverse phase HPLC to afford the title compound of example 5 as a white powder (55 mg, 27% yield).

HPLC-MS calcd. for $C_{22}H_{32}FN_3O_4$ (M+H$^+$) 422.24, found 422.5.

Example 6

2-(R)-Cyclohexylmethyl-N-[2-(4-fluoro-phenylamino)-ethyl]-4-morpholin-4-yl-4-oxo-butyramide

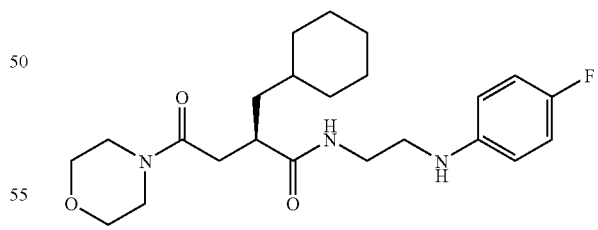

(R)-2-(Cyclohexylmethyl)succinic acid-1-methyl ester (470 mg, 2.06 mmol) (Acros Organics) was treated with morpholine (350 mg, 4.00 mmol, 2 eq.) and HATU (745 mg, 2.26 mmol). The reagents were dissolved in dry dichloromethane (5 mL) and treated with diisopropylethyl-amine (1 mL, 5.741 mmol). The reaction was allowed to stir overnight. The reaction was monitored by LC/MS and the reaction directly purified by prep-LC/MS. Product was obtained as a clear oil (460 mg, 1.54 mmol, 75%). This resulting product (460 mg, 1.54 mmol) was dissolved in a 2:1 mixture of MeOH (10 mL) and H$_2$O (5 mL) and placed in a 0° C. ice bath. Lithium hydroxide (45 mg, 1.87 mmol, 1.2 eq.) was added in one portion and allowed to stir for 8 hours, slowly warming to 23° C. After the reaction was completed, methanol was removed by evaporation. Ethyl acetate (75 mL) was added and the solution was extracted with 1M HCl (50 mL). The aqueous phase was extracted 2×75 mL of ethyl acetate and the combined organic phases were washed with saturated sodium bicarbonate (50 mL), saturated sodium chloride (50 mL) dried over magnesium sulfate, filtered and evaporated to provide 220 mg of product as an yellow oil (0.77 mmol, 50% yield). A portion of the resulting product (220 mg, 0.77 mmol), N1-(4-Fluoro-phenyl)-ethane-1,2-diamine (193 mg, 0.85 mmol, 1.1 eq. prepared according to Scheme 1) and HATU (280 mg, 0.85 mmol, 1.1 eq.) were dissolved in dry dichloromethane (4 mL) and treated with diisopropylethylamine (400 µL, 5.741 mmol). The reaction mixture was allowed to stir overnight and monitored by LC/MS. The reaction mixture was directly purified by prep-LC/MS and provided 56 mg (0.10 mmol, 13%) of the title compound as a white solid: $^1$H NMR (CDCl$_3$, 400 MHz) δ 0.74-1.96 (m, 13H), 2.42-2.98 (m, 3H), 3.21-3.98 (m, 12H), 7.11-7.36 (m, 4H); HPLC-MS calcd. for C$_{23}$H$_{34}$FN$_3$O$_3$ (M+H$^+$) 420.5, found 420.5.

Example 7

[4-(R)-(5-Fluoro-3,3-dimethyl-2,3-dihydro-indol-1-yl)-tetrahydro-furan-3-(R)-yl]-carbamic acid 1-(S)-cyclohexylmethyl-2-morpholin-4-yl-2-oxo-ethyl ester

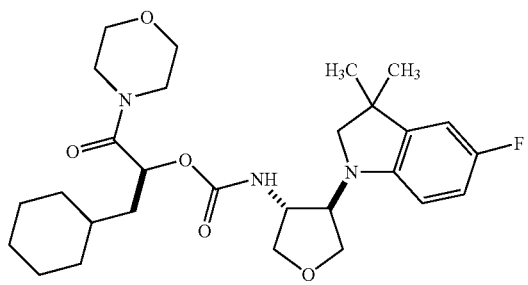

Step A: Synthesis of 1-(4-(R)-Azido-tetrahydro-furan-3-(R)-yl)-5-fluoro-3,3-dimethyl-2,3-dihydro-1H-indole and 1-(4-(R)-Azido-tetrahydro-furan-3-(S)-yl)-5-fluoro-3,3-dimethyl-2,3-dihydro-1H-indole.

A sample of 3-(R)-azido-4-(R)-hydroxytetrahydrofuran (232 mg, 1.8 mmol) was dissolved in dichloromethane (10 mL), cooled in an ice/water bath and treated with the Dess-Martin periodinane (917 mg, 2.2 mmol). The reaction was allowed to warm to room temperature and stirred for 1 hour, at which point TLC analysis indicated that the reaction was over. The resulting solution of the ketone was then treated with a solution of 5-fluoro-3,3-dimethylindoline (328 mg, 2.0 mmol) and acetic acid (148 mg, 2.7 mmol) in methanol (10 mL) and THF (5 mL). The reaction was then treated with sodium cyanoborohydride (170 mg, 2.7 mmol) and stirred overnight. The volatiles were then removed in vacuo and the reaction was picked up in ethyl acetate and extracted with 1 M NaOH. The organics were dried over Na$_2$SO$_4$ and the solvent was removed. The residue was purified by silica gel chromatography using a linear gradient of 0-50% ethyl acetate in hexane to afford 155 mg (31%) of the trans isomer and 50 mg (10%) of the trans isomer.

1-(4-(R)-Azido-tetrahydro-furan-3-(R)-yl)-5-fluoro-3,3-dimethyl-2,3-dihydro-1H-indole: $^1$H NMR (400 MHz, CDCl$_3$) δ 6.77 (m, 2H), 6.38 (dd, J=6.0, 4.0 Hz, 1H), 4.31 (m, 1H), 4.09 (dd, J=10.0, 5.8 Hz, 1H), 4.03 (m, 3H), 3.83 (dd, J=10.0, 3.2 Hz, 1H), 3.45 (d, J=8.2 Hz, 1H), 3.26 (d, J=8.2 Hz, 1H), 1.32 (s, 3H), 1.31 (s, 3H); HPLC-MS calcd. for C$_{14}$H$_{17}$FN$_4$O$_2$ (M+H$^+$) 277.3, found 277.4.

1-(4-(R)-Azido-tetrahydro-furan-3-(S)-yl)-5-fluoro-3,3-dimethyl-2,3-dihydro-1H-indole: $^1$H NMR (400 MHz, CDCl$_3$) δ 6.77 (m, 2H), 6.44 (dd, J=8.5, 4.0 Hz, 1H), 4.11 (m, 2H), 4.02 (m, 3H), 3.75 (dd, J=8.6, 2.6 Hz, 1H), 3.23 (d, J=8.3 Hz, 1H), 3.07 (d, J=8.4 Hz, 1H), 1.29 (s, 3H), 1.27 (s, 3H); HPLC-MS calcd. for C$_{14}$H$_{17}$FN$_4$O$_2$ (M+H$^+$) 277.3, found 277.4.

Step B. A sample of 1-(4-(R)-Azido-tetrahydro-furan-3-(R)-yl)-5-fluoro-3,3-dimethyl-2,3-dihydro-1H-indole (55 mg, 0.20 mmol) was treated with methanol (5 mL) and PtO$_2$ (2.4 mg, 0.01 mmol). A stream of hydrogen was bubbled though the reaction for 5 minutes and the reaction was stirred under a balloon pressure of hydrogen for 3 hours. The atmosphere in the reaction was switched back to nitrogen and the reaction was filtered through a bed of celite. The solvent was removed and the residue was removed and the resulting material was dried on the high vac for an hour. The reaction was then treated with isopropanol (10 mL) and (S)-carbonic acid 1-cyclohexylmethyl-2-morpholin-4-yl-2-oxo-ethyl ester 4-nitro-phenyl ester (81 mg, 0.20 mmol) and diisopropylethylamine (38 mg, 0.3 mmol). The reaction was stirred at room temperature for 24 hours and then at 60° C. for 4 hours. The volatiles were then removed in vacuo and the reaction was picked up in ethyl acetate and extracted with 1 M HCl. The organics were dried over Na$_2$SO$_4$ and the solvent was removed. The residue was purified by silica gel chromatography using a linear gradient of 0-100% ethyl acetate in hexane to afford 64 mg (62%) of material; $^1$H NMR (400 MHz, CDCl$_3$) δ 7.16 (d, J=8.0 Hz, 1H), 6.72 (dd, J=8.4, 2.6 Hz, 1H), 6.66 (ddd, J=8.9, 8.9, 2.7 Hz, 1H), 6.39 (dd, J=8.6, 4.1 Hz, 1H), 5.08 (dd, J=10.3, 3.0 Hz, 1H), 4.44 (m, 1H), 4.03 (m, 2H), 3.70 (m, 2H), 3.44-3.64 (m, 7H), 3.32 (d, J=6.6 Hz, 1H), 3.29 (m, 1H), 3.24 (d, J=8.4 Hz, 1H), 1.55 (m, 8H), 1.25-1.37 (m, 2H), 1.29 (s, 3H), 1.27 (s, 3H), 1.12 (m, 2H), 0.78-0.93 (m, 1H); HPLC-MS calcd. for C$_{28}$H$_{40}$FN$_3$O$_5$ (M+H$^+$) 518.6, found 518.6.

A similar sequence of reactions converted 1-(4-(R)-Azido-tetrahydro-furan-3-(S)-yl)-5-fluoro-3,3-dimethyl-2,3-dihydro-1H-indole to the corresponding [4-(S)-(5-Fluoro-3,3-dimethyl-2,3-dihydro-indol-1-yl)-tetrahydro-furan-3-(R)-yl]-carbamic acid (S)-1-cyclohexylmethyl-2-morpholin-4-yl-2-oxo-ethyl ester: HPLC-MS calcd. for C$_{28}$H$_{40}$FN$_3$O$_5$ (M+H$^+$) 518.6, found 518.6.

Example 8

2-(R)-Cyclohexylmethyl-N-[2-(5-fluoro-2,3-dihydro-indol-1-yl)-1-(S)-methyl-ethyl]-4-morpholin-4-yl-4-oxo-butyramide

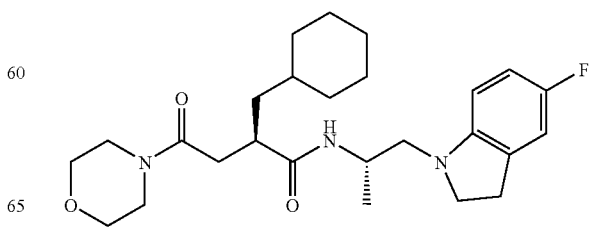

The title compound was synthesized according to the procedure described in Example 6 as a off-white solid: HPLC-MS calcd. for $C_{26}H_{38}FN_3O_3$ (M+H+) 460.3, found 460.5.

Example 9

3-(R)-Cyclohexylmethyl-N-[2-(4-fluoro-phenylamino)-ethyl]-4-morpholin-4-yl-4-oxo-butyramide

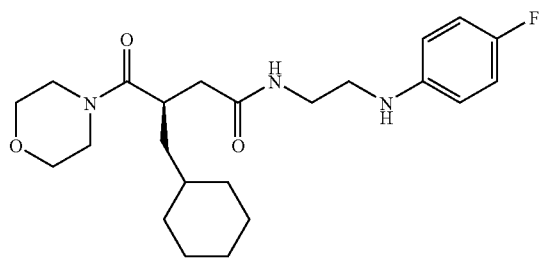

Step A: (R)-2-(Cyclohexylmethyl)succinic acid-1-methyl ester (211 mg, 0.93 mmol) from Acros Organics was treated with (500 µL, 2.87 mmol, 3.1 eq.) of diisopropylethylamine, HATU (360 mg, 1.096 mmol, 1.2 eq.) and (N-(4-Fluorophenyl)-ethane-1,2-diamine) (210 mg, 0.93 mmol, 1 eq.). The reagents were dissolved in dry dichloromethane (5 mL). The reaction was allowed to stir for 5 hours and monitored by LC/MS. Volatiles were removed and the reaction directly purified by automated normal-phase chromatography (0-100% ethyl acetate in hexanes gradient). (R)-2-cyclohexylmethyl-N-[2-(4-fluoro-phenylamino)-ethyl]-succinamic acid methyl ester was obtained as clear oil (220 mg, 0.60 mmol, 65%).

Step B: (R)-2-cyclohexylmethyl-N-[2-(4-fluoro-phenylamino)-ethyl]-succinamic acid methyl ester (220 mg, 0.60 mmol, 1.0 eq.) was dissolved in a mixture of MeOH (4.5 mL) and H₂O (3 mL) and placed in a 0° C. ice bath. Lithium hydroxide (30 mg, 1.25 mmol, 2.1 eq.) was added in one portion and allowed to stir for 8 hours, slowly warming to 23° C. After the reaction was judged complete by LC/MS, methanol was removed by evaporation. Ethyl acetate (75 mL) was added to the resulting solution and was extracted with 1 M HCl (50 mL). The aqueous phase was extracted 2×75 mL of ethyl acetate and the combined organic phases were washed with saturated sodium bicarbonate (50 mL), saturated sodium chloride (50 mL) dried over magnesium sulfate, filtered and evaporated to provide 183 mg of (R)-2-cyclohexylmethyl-N-[2-(4-fluoro-phenylamino)-ethyl]-succinamic acid an yellow oil (0.52 mmol, 86%) and was used directly in the following reaction.

Step C: (R)-2-cyclohexylmethyl-N-[2-(4-fluoro-phenylamino)-ethyl]-succinamic acid (220 mg, 0.52 mmol) was treated with morpholine (110 µL, 1.26 mmol, 2.4 eq.) and HATU (238 mg, 0.72 mmol, 1.4 eq.). The reagents were dissolved in dry dichloromethane (4 mL) and treated with diisopropylethylamine (315 µL, 1.81 mmol, 3.5 eq.). The reaction was judged to completion by LC/MS, volatiles were evaporated and the reaction was purified by prep-LC/MS and provided 131 mg (0.25 mmol, 40%) of a off-white solid: HPLC-MS calcd. for $C_{23}H_{34}FN_3O_3$ (M+H+) 420.3, found 420.5.

Example 10

[1-(R)—Benzyloxymethyl-2-(5-fluoro-2,3-dihydro-indol-1-yl)-ethyl]-carbamic acid 1-(S)-cyclohexylmethyl-2-morpholin-4-yl-2-oxo-ethyl ester

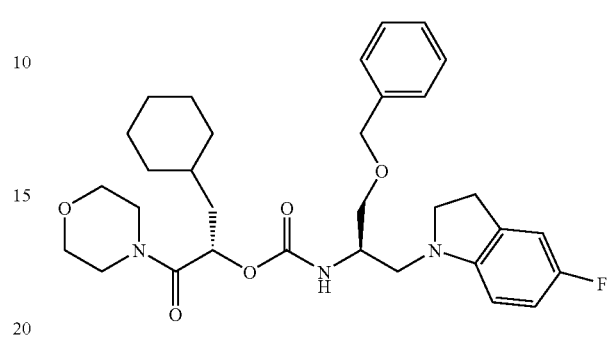

The title compound was synthesized according to the procedure outlined in Example 5 starting from 1-(R)-benzyloxymethyl-2(5-fluoro-2,3-dihydro-indol-1-yl)-ethylamine.

¹H-NMR (CD₃OD) δ 7.35(m, 5H), 6.78 (m, 1H), 6.66 (m, 1H), 6.42 (m, 1H), 5.28 (m, 1H), 4.52 (m, 2H), 3.99 (m, 1H), 3.60 (m, 11H), 3.43 (m, 1H), 3.14 (m, 2H), 2.87 (m, 2H), 1.80 (m, 1H), 1.67 (m, 5H), 1.42 (m, 2H), 1.18 (m, 3H), 0.92 (m, 2H). HPLC-MS calcd. for $C_{32}H_{42}FN_3O_5$ (M+H+) 568.31, found 568.6.

Example 11

[2-(5-Fluoro-2,3-dihydro-indol-1-yl)-1-(R)-hydroxymethyl-ethyl]-carbamic acid 1-(S)-cyclohexylmethyl-2-morpholin-4-yl-2-oxo-ethyl ester

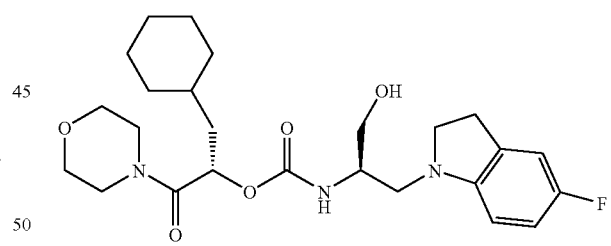

The title compound of Example 10 (50 mg, 0.088 mmol) was dissolved in a minimum amount of methanol (approx. 1-2 mL) and a catalytic amount of 10% Pd/C was added. Air was purged from the reaction vessel and H₂ gas was introduced via a balloon. The reaction mixture was stirred for several hours under a H₂ atmosphere, after which point the starting material had disappeared by LCMS. The Pd/C was filtered and the crude material was purified by reverse-phase HPLC to afford the title compound (30 mg, 71% yield).

¹H-NMR (CD₃OD) δ 6.78 (m, 1H), 6.71 (m, 1H), 6.49 (m, 1H), 5.28 (m, 1H), 3.88 (m, 1H), 3.62 (m, 9H), 3.47 (m, 3H), 3.12 (m, 2H), 2.89 (m, 2H), 1.80 (m, 1H), 1.67 (m, 5H), 1.45 (m, 2H), 1.19 (m, 3H), 0.92 (m, 2H). HPLC-MS calcd. for $C_{25}H_{36}FN_3O_5$ (M+H+) 478.26, found 478.5.

Example 12

Morpholine-4-carboxylic acid 2-cyclohexyl-1-(S)-[2-(5-fluoro-2,3-dihydro-indol-1-yl)-1-(S)-methyl-ethylcarbamoyl]-ethyl ester

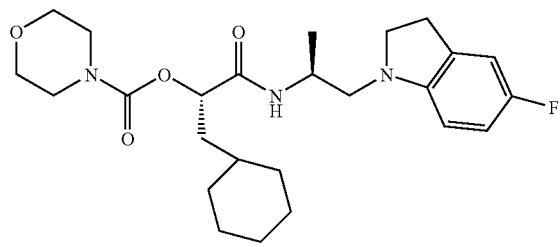

The title compound was synthesized according to the procedure outlined in Example 1 starting from 2-(5-fluoro-2,3-dihydro-indol-1-yl)-1-(S)-methyl-ethylamine.
HPLC-MS calcd. for $C_{25}H_{36}FN_3O_4$ (M+H$^+$) 462.27, found 462.2.

Example 13

2-(R)-Cyclohexylmethyl-4-morpholin-4-yl-4-oxo-N-[2-(4-trifluoromethoxy-phenylamino)-ethyl]-butyramide

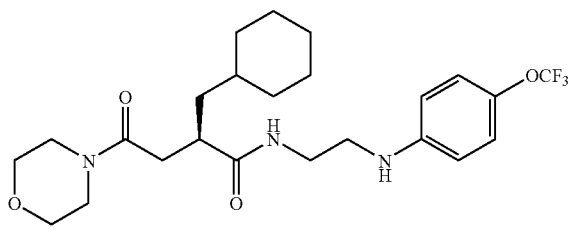

The title compound was synthesized according to the procedure described in Example 6 as a off-white solid: HPLC-MS calcd. for $C_{24}H_{34}F_3N_3O_4$ (M+H$^+$) 486.3, found 486.4.

Example 14

2-(R)-Cyclohexylmethyl-N-[1-(S)-methyl-2-(4-trifluoromethoxy-phenylamino)-ethyl]-4-morpholin-4-yl-4-oxo-butyramide

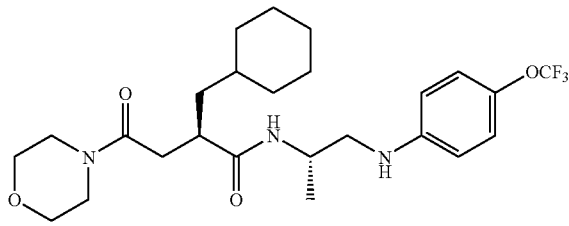

The title compound was synthesized according to the procedure described in Example 6 as a off-white solid: HPLC-MS calcd. for $C_{25}H_{36}F_3N_3O_4$ (M+H$^+$) 500.3, found 500.4.

Example 15

2-(R)-Cyclopentylmethyl-N-[1-(S)-methyl-2-(4-trifluoromethoxy-phenylamino)-ethyl]-4-morpholin-4-yl-4-oxo-butyramide

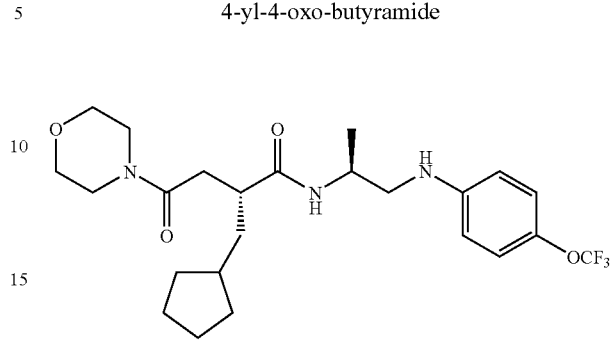

The title compound was synthesized according to the procedure described in Example 21 as a light brown solid: HPLC-MS calcd. for $C_{24}H_{34}F_3N_3O_4$ (M+H$^+$) 486.3, found 486.4.

Example 16

2-(R)-Cyclopentylmethyl-3-(R)-methyl-N-[1-(S)-methyl-2-(4-trifluoromethoxy-phenylamino)-ethyl]-4-morpholin-4-yl-4-oxo-butyramide

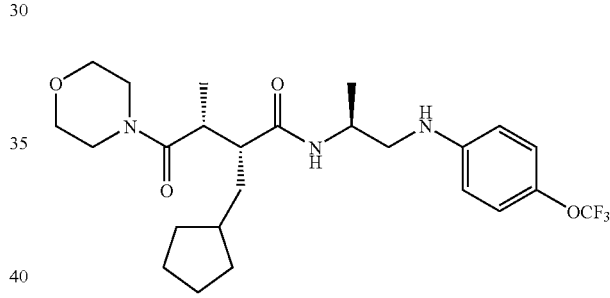

Step A: 4-(4-(S)-Benzyl-2-oxo-oxazolidin-3-yl)-3-(R)-cyclopentylmethyl-4-oxo-butyric acid tert-butyl ester (620 mg, 1.49 mmol, 1.0 eq.) was dissolved in THF (35 mL) and cooled in a 0° C. ice-water bath. Hydrogen peroxide (31 w/w %) (654 μL, 5.97 mmol, 4.0 eq.) and LiOH (72 mg, 2.98 mmol, 2.0 eq.) in water (7.5 mL) was added to the reaction mixture. The reaction stirred at 0° C. and judged to completion by LC/MS. Saturated sodium sulfite (18 mL) and sodium bicarbonate (18 mL) is added to the reaction. THF was evaporated by rotary evaporation and extracted the aqueous layer with $CH_2Cl_2$ (3×75 mL) to remove the chiral auxiliary. The aqueous layer was acidified at 0° C. with 6M HCl to pH~1 and extracted with ethyl acetate (4×75 mL). The combined organic extracts were dried over $MgSO_4$, filtered and evaporated to provide 281 mg (1.10 mmol, 73%) of 2-(R)—Cyclopentylmethyl-succinic acid 4-tert-butyl ester as clear oil and used directly in Step B. HPLC-MS calcd. for $C_{14}H_{24}O_4$ (M+Na$^+$) 279.3, found 279.3.

Step B: 2-(R)-Cyclopentylmethyl-succinic acid 4-tert-butyl ester (138 mg, 0.54 mmol, 1.0 eq.) was dissolved in dry THF (3 mL) and cooled to −78° C. in an acetone/dry ice bath. Lithium diisopropylamide (2.0M in THF, 600 μL, 1.20 mmol, 2.2 eq.) was added to the reaction and allowed to stir at −78° C. for 1 hour. Methyl iodide (40 μL, 0.65 mmol, 1.2 eq.) was added and the reaction stirred at −78° C. for 2 hours. MeOH (2 mL) was added at −78° C. to quench the reaction. THF and MeOH were removed by rotary evaporation and dissolved in ethyl acetate (30 mL). The organic layer was washed with 1M HCl (20 mL), saturated NaHCO$_3$ (20 mL), and brine. Dried organic layer over magnesium sulfate, filtered and evaporated to provide 130 mg (0.51, 96%) of a clear oil. The reaction provides a 3:1 mixture of starting material and desired product, 2-(R)-Cyclopentylmethyl-3-(R)-methyl-succinic acid 4-tert-butyl ester. The material is used directly. HPLC-MS calcd. for C$_{15}$H$_{26}$O$_4$ (M+Na$^+$) 293.3, found 293.3.

Step C: 3-(R)-Cyclopentylmethyl-2-(R)-methyl-N-[1-(S)-methyl-2-(4-trifluoromethoxy-phenylamino)-ethyl]-succinamic acid tert-butyl ester was prepared according to example 21. The product was isolated and used directly in the next reaction. HPLC-MS calcd. for C$_{25}$H$_{37}$F$_3$N$_2$O$_4$ (M+H$^+$) 487.3, found 487.4.

Step D: 3-(R)-Cyclopentylmethyl-2-(R)-methyl-N-[1-(S)-methyl-2-(4-trifluoromethoxy-phenylamino)-ethyl]-succinamic acid was prepared according to example 21. The product was isolated and used directly in the next reaction. HPLC-MS calcd. for C$_{21}$H$_{29}$F$_3$N$_2$O$_4$ 431.2 (M+H$^+$), found 431.4.

Step E: The title compound 2-(R)-Cyclopentylmethyl-3-(R)-methyl-N-[1-(S)-methyl-2-(4-trifluoromethoxy-phenylamino)-ethyl]-4-morpholin-4-yl-4-oxo-butyramide was prepared according to example 21. The product was isolated by mass-directed HPLC to provide 12 mg of a white solid after evaporation and lyophilization (0.020 mmol, 3.6% over 3 steps). HPLC-MS calcd. for C$_{25}$H$_{36}$F$_3$N$_3$O$_4$ (M+H$^+$) 500.3, found 500.5.

Example 17

Morpholine-4-carboxylic acid {2-benzylsulfanyl-1-(R)-[1-(S)-methyl-2-(4-trifluoromethoxy-phenylamino)-ethylcarbamoyl]-ethyl}-amide

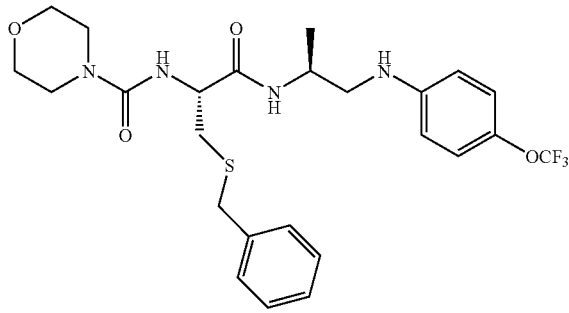

Step A: 2-(R)-Amino-3-benzylsulfanyl-propionic acid (1.21 g, 5.75 mmol, 1.0 eq.) was suspended in acetonitrile (18 mL) and water (1.5 mL) and treated with Et$_3$N and allowed to stir at 23° C. for 20 minutes. Added morpholine carbonyl chloride via syringe and allowed to stir for 3 hours and monitored by LC/MS. Upon completion, the reaction was diluted with ethyl acetate (150 mL) and extracted with 1M HCl (50 mL), saturated NaHCO$_3$ (50 mL) and brine. Dried organic layer over magnesium sulfate, filtered and evaporated to provide 2.80 g of 3-(R)—Benzylsulfanyl-2-[(morpholine-4-carbonyl)-amino]-propionic acid as a light yellow oil that was used directly in the next step. HPLC-MS calcd. for C$_{15}$H$_{20}$N$_2$O$_4$S (M+H$^+$) 325.1, found 325.3.

Step B: 3-Benzylsulfanyl-2-(R)-[(morpholine-4-carbonyl)-amino]-propionic acid (182 mg, 0.56 mmol, 1.2 eq.), N$^1$-(4-Trifluoromethoxy-phenyl)-(S)-propane-1,2-diamine from Scheme 1a (110 mg, 0.47 mmol, 1.0 eq.), and HATU (185 mg, 0.56 mmol, 1.2 eq.) were dissolved in CH$_2$Cl$_2$ (2 mL) at room temperature. DIPEA (245 μL, 1.41 mmol, 3.0 eq.) was added via syringe and the resulting mixture was monitored by LC/MS to completion. After the reaction was complete, the solvent was evaporated and directly purified by mass-directed HPLC and provided 22 mg (0.03 mmol, 5%) of a off-white solid (mono-TFA salt): HPLC-MS calcd. for C$_{25}$H$_{31}$F$_3$N$_4$O$_4$S (M+H$^+$) 541.2, found 541.3.

Example 18

Morpholine-4-carboxylic acid {1-(R)-[1-(S)-methyl-2-(4-trifluoromethoxy-phenylamino)-ethylcarbamoyl]-2-phenylmethanesulfonyl-ethyl}-amide

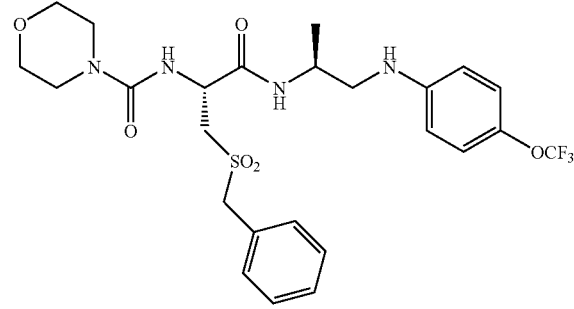

Step A: 3-Benzylsulfanyl-2-(R)-[(morpholine-4-carbonyl)-amino]-propionic acid (780 mg, 2.41 mmol, 1.0 eq.) was dissolved in CH$_2$Cl$_2$ and placed in a 0° C. ice-water bath. Added mCPBA (77%) (1.62 g, 7.22 mmol, 3 eq.) in one portion and allowed to stir until completion by LC/MS. Reaction quench with dimethyl sulfide (5 mL) and the solvent was evaporated. Direct purification by mass-directly HPLC provided 2-(R)-[(Morpholine-4-carbonyl)-amino]-3-phenylmethanesulfonyl-propionic acid as a clear oil (73 mg, 0.21 mmol, 9%): HPLC-MS calcd. for C$_{15}$H$_{20}$N$_2$O$_6$S (M+H$^+$) 357.1, found 357.3.

Step B: 2-(R)-[(Morpholine-4-carbonyl)-amino]-3-phenylmethanesulfonyl-propionic acid (73 mg, 0.21 mmol, 1.0 eq.), N$^1$-(4-Trifluoromethoxy-phenyl)-(S)-propane-1,2-diamine from Scheme 1a (48 mg, 0.21 mmol, 1.0 eq.), EDC (59 mg, 0.31 mmol, 1.5 eq.), and HOBT (38 mg, 0.25 mmol, 1.2 eq.) were dissolved in CH$_2$Cl$_2$ at room temperature. N-methylmorpholine (225 μL, 2.05 mmol, 10 eq.) was added via syringe and the reaction was monitored to completion by LC/MS. The solvent was evaporated and the reaction was purified by mass-directed HPLC and provided 44 mg (0.06 mmol, 31%) of a off-white solid as a mono-TFA salt: HPLC-MS calcd. for C$_{25}$H$_{31}$F$_3$N$_4$O$_6$S (M+H$^+$) 573.2, found 573.3.

Example 19

(R)-2-Cyclohexylmethyl-N-[2-(4-methoxy-phenylamino)-ethyl]-4-morpholin-4-yl-4-oxo-butyramide

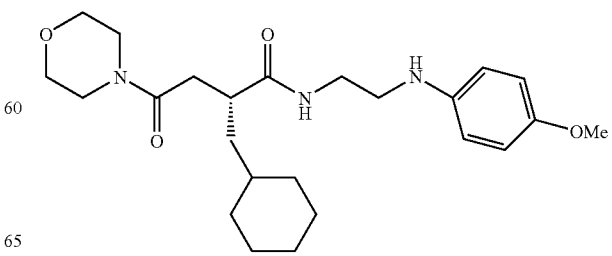

C$_{24}$H$_{37}$N$_3$O$_4$; HPLC-MS: 432.5 (M+H$^+$).

Example 20

2-(R)-Cyclohexylmethyl-4-morpholin-4-yl-4-oxo-N-{1-(S)-[(4-trifluoromethoxy-phenylamino)-methyl]-butyl}-butyramide

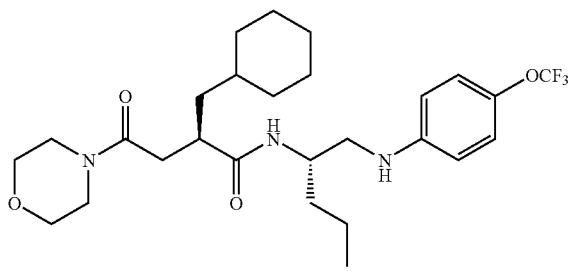

Compound was synthesized in a similar fashion to Example 6 using an appropriate diamine. HPLC-MS calcd. for $C_{27}H_{40}F_3N_3O_4$ (M+H$^+$) 528.3, found 528.6.

Example 21

2-(R)-(2-Cyclohexyl-ethyl)-N-[1-(S)-methyl-2-(4-trifluoromethoxy-phenylamino)-ethyl]-4-morpholin-4-yl-4-oxo-butyramide

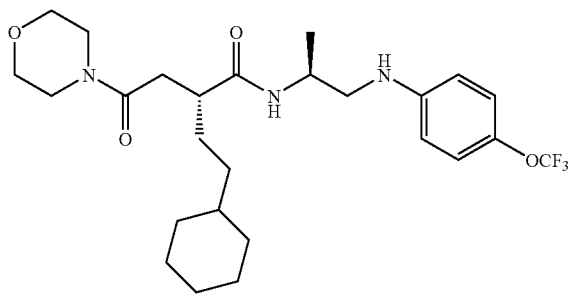

Step A: 4-Cyclohexyl-butyric acid (3.4 g, 20.0 mmol, 1.0 eq.) was dissolved in dry $CH_2Cl_2$ (10 mL) and cooled to 0° C. in an ice water bath. A few drops of DMF was added (~100 μL) followed by slow addition of thionyl chloride (2.07 mL, 20.0 mmol, 1 eq.) via syringe. The reaction mixture was warmed to room temperature and stirred for 2 hours. Solvent was evaporated and the resulting 4-cyclohexyl-butyryl chloride used directly in Step B without further purification.

Step B: Performed as described in Evans, D. A., et al. *Tetrahedron* 1988, 44, 5525 using 4-cyclohexyl-butyryl chloride. (S)-4-Benzyl-3-(4-cyclohexyl-butyryl)-oxazolidin-2-one (5.65 g, 17.15 mmol, 88%) was isolated as a white solid. HPLC-MS calcd. for $C_{20}H_{27}NO_3$ (M+Na$^+$) 352.3, found 352.1.

Step C: Performed as described in Evans, D. A., et al. *J. Org. Chem.* 1999, 64, 6411 using (S)-4-benzyl-3-(4-cyclohexyl-butyryl)-oxazolidin-2-one. 3-(R)-(4-(S)-Benzyl-2-oxo-oxazolidine-3-carbonyl)-5-cyclohexyl-pentanoic acid tert-butyl ester (2.5 g, 5.63 mmol, 84%) was isolated as a clear oil and >20:1 mixture of diastereomers: $^1$H NMR (CDCl$_3$, 400 MHz) δ 0.66-0.78 (m, 2H), 0.96-1.14 (m, 6H), 1.30 (s, 9H), 1.32-1.56 (m, 7H), 2.34 (dd, 1H, J=16.8, 4.0 Hz), 2.61 (dd, 1H, J=12.4, 6.0 Hz), 2.66 (dd, 1H, J=16.8, 10.4 Hz), 3.21 (dd, 1H, J=13.6, 3.2 Hz), 3.96-3.21 (m, 3H), 4.55 (m, 1H), 7.13-7.23 (m, 5H).

Step D: 3-(R)-(4-(S)-Benzyl-2-oxo-oxazolidine-3-carbonyl)-5-cyclohexyl-pentanoic acid tert-butyl ester (2.01 g, 4.53 mmol, 1.0 eq) was treated with a 45:50:5 $CH_2Cl_2$:TFA:$H_2O$ solution. The reaction was monitored by LC/MS and complete after 1 hour. The solution was evaporated and provided a quantitative yield of 3-(R)-(4-(S)-Benzyl-2-oxo-oxazolidine-3-carbonyl)-5-cyclohexyl-pentanoic acid as a yellow oil. $^1$H NMR (CDCl$_3$, 400 MHz) δ 0.80-0.91 (m, 2H), 1.09-1.27 (m, 6H), 1.44-1.53 (m, 1H), 1.61-1.73 (m, 6H), 2.12 (s, 2H), 2.35 (dd, 1H, J=17.2, 4.0 Hz), 2.49 (dd, 1H, J=13.6, 9.6 Hz), 2.71 (dd, 1H, J=17.6, 10.8 Hz), 3.03 (dd, 1H, J=13.6, 3.2 Hz), 3.87-3.97 (m, 3H), 4.43 (m, 1H), 6.90-7.10 (m, 5H).

Step E: 3-(R)-(4-(S)-Benzyl-2-oxo-oxazolidine-3-carbonyl)-5-cyclohexyl-pentanoic acid (1.76 g, 4.53 mmol, 1.0 eq.) dissolved in DMF (10 mL) and treated with HATU (1.3 g, 5.0 mmol, 1.1 eq.), morpholine (680 μL, 7.77 mmol, 1.7 eq.) and DIPEA (870 μL, 5.0 mmol, 1.1 eq.). Alternatively an additional equivalent of morpholine can be used in the reaction and $CH_2Cl_2$ can be used as the reaction solvent. The reaction is monitored by LC/MS. The reaction mixture is diluted with ethyl acetate (50 mL) and extracted with 0.5 M HCl (2×10 mL), saturated NaHCO$_3$, and brine. The organic layer is dried over MgSO$_4$, filtered and evaporated. The crude mixture is used in Step F directly or purified by normal-phase silica chromatography in a 20-50% ethyl acetate in hexanes gradient to provide 1-(4-(S)-Benzyl-2-oxo-oxazolidin-3-yl)-2-(R)-(2-cyclohexyl-ethyl)-4-morpholin-4-yl-butane-1,4-dione as a white solid (1.91 g, 4.18 mmol, 92%): $^1$H NMR (CDCl$_3$, 400 MHz) δ 0.80-0.91 (m, 2H), 1.09-1.27 (m, 6H), 1.44-1.53 (m, 1H), 1.61-1.73 (m, 6H), 2.12 (s, 2H), 2.35 (dd, 1H, J=17.2, 4.0 Hz), 2.49 (dd, 1H, J=13.6, 9.6 Hz), 2.71 (dd, 1H, J=17.6, 10.8 Hz), 3.03 (dd, 1H, J=13.6, 3.2 Hz), 3.48-3.72 (m, 8H), 3.87-3.97 (m, 3H), 4.43 (m, 1H), 6.90-7.10 (m, 5H), 8.02 (s, 1H).

Step F: The chiral auxiliary was removed in an identical manner to Step A of Example 16. 2-(R)-(2-Cyclohexyl-ethyl)-4-morpholin-4-yl-4-oxo-butyric acid was isolated as a white solid (1.0 g, 3.36 mmol, 80%). HPLC-MS calcd. for $C_{16}H_{27}NO_4$ (M+H$^+$) 298.2, found 298.1.

Step G: 2-(R)-(2-Cyclohexyl-ethyl)-4-morpholin-4-yl-4-oxo-butyric acid (98 mg, 0.33 mmol, 1.0 eq.) dissolved in DMF (2 mL) and treated with HATU (137 mg, 0.36 mmol, 1.1 eq.), (S)—N$^1$-(4-Trifluoromethoxy-phenyl)-propane-1,2-diamine (85 mg, 0.36 mmol, 1.1 eq.) and DIPEA (63 μL, 0.36 mmol, 1.1 eq.). Alternatively $CH_2Cl_2$ can be used as the reaction solvent based on starting material solubility. The reaction is monitored by LC/MS. The reaction mixture is diluted with ethyl acetate (20 mL) and extracted with 0.5 M HCl (2×10 mL), saturated NaHCO$_3$, and brine. The organic layer is dried over MgSO$_4$, filtered and evaporated. Alternatively, the crude reaction can be directly purified by mass-directed HPLC. Mass-directed HPLC provides the title compound as a white solid after evaporation and lyophilization: $^1$H NMR (CD$_3$OD, 400 MHz) δ 0.74-0.82 (m, 2H), 1.08-1.65 (m, 13H), 1.21 (d, J=6.8 Hz, 3H), 2.38 (dd, J=4.8, 15.6 Hz, 1H), 2.65 (m, 1H), 2.74 (dd, J=9.6, 15.6 Hz, 1H), 3.10 (m, 2H), 3.54-3.66 (m, 8H), 4.11 (m, 1H), 6.45 (m, 2H), 6.97 (m, 2H). HPLC-MS calcd. for $C_{26}H_{38}F_3N_3O_4$ (M+H$^+$) 514.3, found 514.2.

Example 22

2-(R)-Cyclohexylmethyl-4-morpholin-4-yl-4-oxo-N-{1-(S)-[(4-trifluoromethoxy-phenylamino)-methyl]-propyl}-butyramide

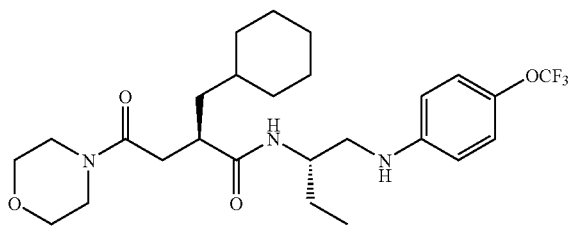

The compound was synthesized in an analogous fashion to Example 6. HPLC-MS calcd. for $C_{26}H_{38}F_3N_3O_4$ (M+H$^+$) 514.3, found 514.6.

Example 23

2-(R)-Cyclohexylmethyl-4-morpholin-4-yl-4-oxo-N-{3-phenyl-1-(S)-[(4-trifluoromethoxy-phenylamino)-methyl]-propyl}-butyramide

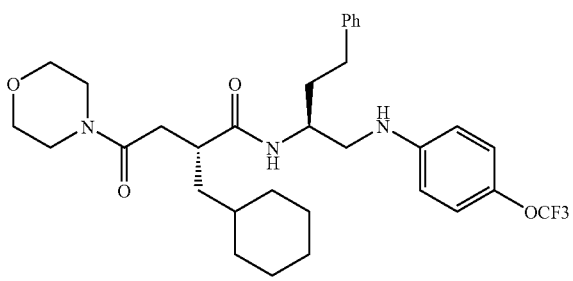

The compound was synthesized in an analogous fashion to Example 6. HPLC-MS calcd. for $C_{32}H_{42}F_3N_3O_4$ (M+H$^+$) 590.3, found 590.6.

Example 24

2-(R)-Cyclohexylmethyl-N-{2-methyl-1-(S)-[(4-trifluoromethoxy-phenylamino)-methyl]-propyl}-4-morpholin-4-yl-4-oxo-butyramide

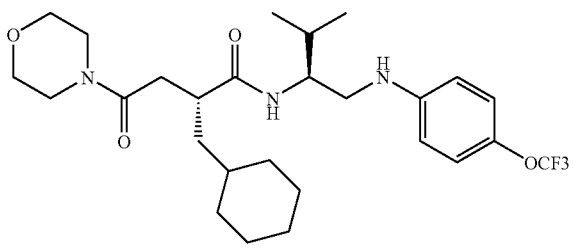

The compound was synthesized in an analogous fashion to Example 6. HPLC-MS calcd. for $C_{27}H_{40}F_3N_3O_4$ (M+H$^+$) 528.3, found 528.6.

Example 25

5,5-Dimethyl-2-(R)-(2-morpholin-4-yl-2-oxo-ethyl)-hexanoic acid [1-(S)-methyl-2-(4-trifluoromethoxy-phenylamino)-ethyl]-amide

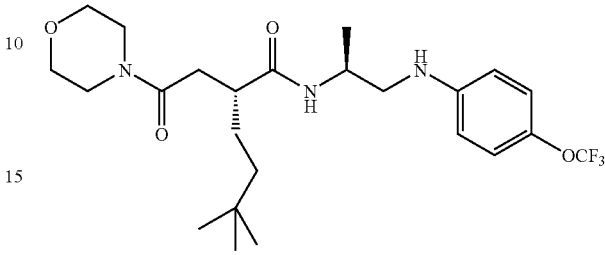

5,5-Dimethyl-hex-2-enoic acid was prepared using a modified procedure from Chatterjee, A. K. et al. *J. Am. Chem. Soc.* 2003, 125(37), 11360-11370. 4,4-Dimethyl-1-pentene (5.0 mL, 34.77 mmol, 1.5 eq.) and acrylic acid (1.54 mL, 22.51 mmol, 1.0 eq.) were added to a solution of ruthenium catalyst ([1,3-bis(2,4,6-trimethylphenyl)-2-imidazolidinylidene]dichloro [[2-(1-methylethoxy-)phenyl]methylene-]ruthenium, 282 mg, 0.45 mmol, 2 mol %) in CH$_2$Cl$_2$ and heated to reflux for 12 hours under nitrogen atmosphere. The resulting brown solution was diluted with CH$_2$Cl$_2$ and washed with 1M NaOH (3×15 mL). The organic phase was acidified with 4 M HCl (20 mL) and extracted with EtOAc (3×25 mL). The combined organics were washed with brine, dried over MgSO$_4$, filtered and evaporated to provide intermediate 5,5-Dimethyl-hex-2-enoic acid as a light brown oil (3.16 g, 22.21 mmol, 99%): $^1$H NMR (CDCl$_3$, 400 MHz) δ 0.94 (s, 9H), 2.11 (d, 2H, J=8.0 Hz), 5.82 (d, 1H, J=16.0 Hz), 7.12 (dt, 1H, J=16.0, 8.0 Hz).

5,5-Dimethyl-hex-2-enoic acid was reduced to 5,5-dimethyl-hexanoic acid by the procedure described in example 26, step B.

5,5-Dimethyl-hexanoic acid was converted to the title compounds using the procedures that described in Example 21.

$^1$H NMR (CD$_3$OD, 400 MHz) δ 0.80 (s, 9H), 1.18 (m, 2H), 1.21 (d, J=6.8 Hz, 3H), 1.43-1.52 (m, 2H), 2.40 (dd, J=4.8, 16 Hz, 1H), 2.61 (m, 1H), 2.76 (dd, J=9.6, 15.6 Hz, 1H), 3.11 (m, 2H), 3.52-3.65 (m, 8H), 4.10 (m, 1H), 6.64 (m, 2H), 6.98 (m, 2H). HPLC-MS calcd. for $C_{24}H_{36}F_3N_3O_4$ (M+H$^+$) 488.3, found 488.2.

Example 26

4,4-Dimethyl-2-(R)-(2-morpholin-4-yl-2-oxo-ethyl)-pentanoic acid [1-(S)-methyl-2-(4-trifluoromethoxy-phenylamino)-ethyl]-amide

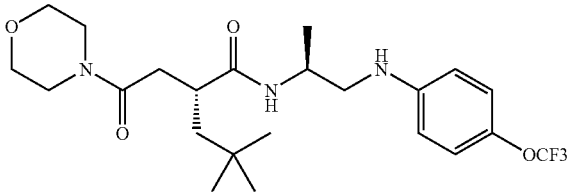

Step A: Methyl diethylphosphonoacetate (13.35 mL, 73.6 mmol, 1.05 eq.) was dissolved in THF (30 mL) and cooled to −78° C. in an acetone-dry ice bath. n-BuLi (1.6M in hexanes) (45.8 mL, 73.2 mmol, 1.05 eq.) was added slowly over 20 min. Trimethylacetaldehyde (6.0 g, 69.6 mmol, 1.0 eq.), was added to the reaction and allowed to stir at −78° C. for 20 minutes and warmed to room temperature and stirred overnight. Water (30 mL) was added to quench and extracted with ethyl ether (3×100 mL). The combined organics were washed with brine and dried over $MgSO_4$, filtered and evaporated to provide 4,4-Dimethyl-pent-2-enoic acid methyl ester, a colorless liquid (8.52 g, 60.0 mmol, 86%) and was used directly in the next reaction. $^1$H NMR ($CDCl_3$, 400 MHz) δ 0.89 (s, 9H), 3.64 (s, 3H), 5.64 (d, 1H, J=16.0 Hz), 6.88 (d, 1H, J=16.0 Hz).

Step B: 4,4-Dimethyl-pent-2-enoic acid methyl ester (8.52 g, 60.0 mmol) was dissolved in MeOH (30 mL) and ethyl acetate (30 mL). Palladium on carbon (10 wt %) (~50 mg) was added to the reaction and was placed under a $H_2$ balloon (1 atm). The reaction was allowed to stir for 12 hours, flushed with nitrogen and filtered over a pad of celite. Evaporated to provide 4,4-dimethyl-pentanoic acid methyl ester (7.0 g, 48.5 mmol, 81%) as a colorless oil: $^1$H NMR ($CDCl_3$, 400 MHz) δ 0.89 (s, 9H), 1.53-1.57 (m, 2H), 2.26-2.30 (m, 2H), 3.67 (s, 3H).

Step C: 4,4-Dimethyl-pentanoic acid methyl ester (7.0 g, 48.5 mmol, 1.0 eq.) was treated with a solution of NaOH (4.0 g, 100 mmol, 2.1 eq.) in water (5 mL). The homogeneous solution was allowed to stir for 4-5 hours. The reaction was diluted with $CH_2Cl_2$ and the aqueous layer was extracted with $CH_2Cl_2$ (50 mL×3). The aqueous layer was acidified with 6M HCl to pH ~1.5 and extracted with ethyl acetate (50 mL×3). The combined ethyl acetate fractions were dried over $MgSO_4$, filtered and evaporated to provide 4,4-dimethyl-pentanoic acid (5.35 g, 41.1 mmol, 85%) as a colorless oil: $^1$H NMR ($CDCl_3$, 400 MHz) δ 0.89 (s, 9H), 1.53-1.57 (m, 2H), 2.26-2.30 (m, 2H).

4,4-dimethyl-pentanoic acid was converted to the title compounds using the procedures that described in Example 21.

$^1$H NMR ($CD_3OD$, 400 MHz) δ 0.90 (s, 9H), 1.18 (d, J=6.8 Hz 3H), 1.20-1.29 (m, 2H), 1.77 (dd, J=9.2, 14 Hz, 1H), 2.39 (dd, J=6.4, 15.6 Hz, 1H), 2.61 (dd, J=8.4, 15.6 Hz, 1H), 2.82 (m, 1H), 2.99-3.05 (m, 1H), 3.21 (dd, J=6.8, 12.8 Hz, 1H), 3.50-3.65 (m, 8H), 4.04 (m, 1H), 6.63-6.66 (m, 2H), 6.96-6.99 (m, 2H). HPLC-MS calcd. for $C_{23}H_{34}F_3N_3O_4$ (M+H$^+$) 474.3, found 474.2.

Example 27

2-(R)-Cyclopentylmethyl-4-morpholin-4-yl-4-oxo-N-{1-(S)-[(4-trifluoromethoxy-phenylamino)-methyl]-butyl}-butyramide

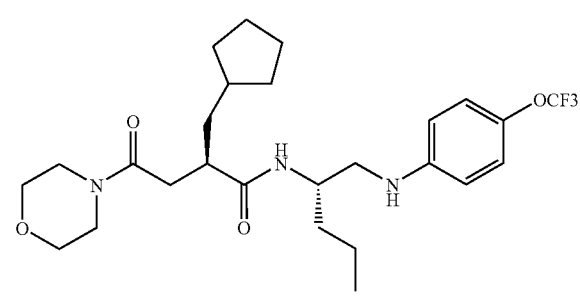

Compound is synthesized in accordance with Example 21. HPLC-MS calcd. for $C_{26}H_{38}F_3N_3O_4$ (M+H$^+$) 514.3, found 514.5.

Example 28

2-(R)-Cyclohexylmethyl-N-{3-methanesulfonyl-1-(S)-[(4-trifluoromethoxy-phenylamino)-methyl]-propyl}-4-morpholin-4-yl-4-oxo-butyramide

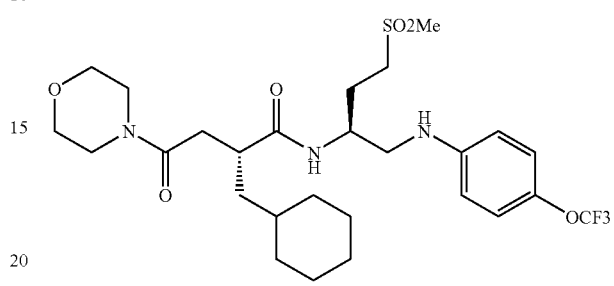

Compound is synthesized in accordance with Example 6. HPLC-MS calcd. for $C_{27}H_{40}F_3N_3O_6S$ (M+H$^+$) 592.3, found 592.5.

Example 29

2-(R)-Cyclohexylmethyl-N-{3-methanesulfonyl-1-(R)-[(4-trifluoromethoxy-phenylamino)-methyl]-propyl}-4-morpholin-4-yl-4-oxo-butyramide

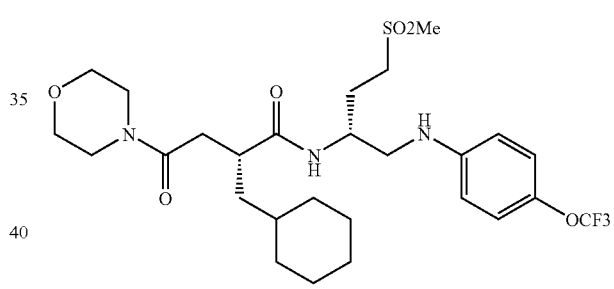

Compound was isolated as a minor diastereomers from the synthesis of Example 28. HPLC-MS calcd. for $C_{27}H_{40}F_3N_3O_6S$ (M+H$^+$) 592.3, found 592.5.

Example 30

2-(R)-(2-Morpholin-4-yl-2-oxo-ethyl)-5-phenyl-pentanoic acid {2-methyl-1-(S)-[(4-trifluoromethoxy-phenylamino)-methyl]-propyl}-amide

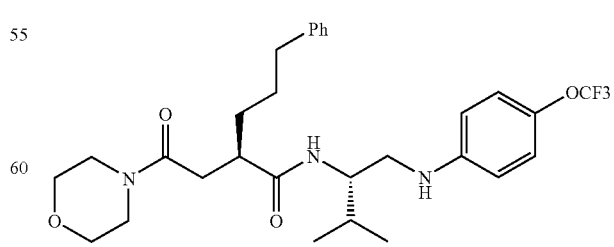

Compound was synthesized in accordance with Example 21. HPLC-MS calcd. for $C_{29}H_{38}F_3N_3O_4$ (M+H$^+$) 550.3, found 550.5.

Example 31

2-(R)-Cyclopentylmethyl-N-{2-methyl-1-(S)-[(4-trifluoromethoxy-phenylamino)-methyl]-propyl}-4-morpholin-4-yl-4-oxo-butyramide

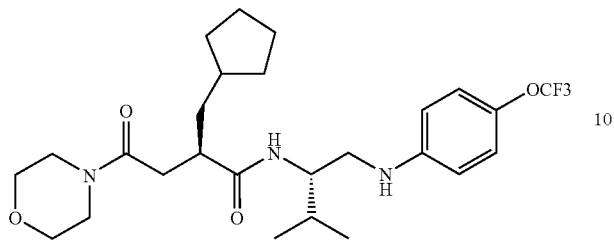

Compound is synthesized in accordance with Example 21. $^1$H NMR (CD$_3$OD, 400 MHz) δ 0.96 (d, J=6.8 Hz, 3H), 0.98 (d, J=6.8 Hz, 3H), 1.03-1.93 (m, 12H), 2.39 (dd, J=4.4, 15.2 Hz, 1H), 2.70-2.76 (m, 1H), 3.11 (dd, J=8.4, 12.8 Hz, 1H), 3.26 (dd, J=4.0, 12.4 Hz, 1H), 3.52-3.66 (m, 8H), 3.87 (m, 1H), 6.59-6.63 (m, 2H), 6.98-7.00 (m, 2H). HPLC-MS calcd. for C$_{26}$H$_{38}$F$_3$N$_3$O$_4$ (M+H$^+$) 514.3, found 514.2.

Example 32

N-{2-Methyl-1-(S)-[(4-trifluoromethoxy-phenylamino)-methyl]-propyl}-4-morpholin-4-yl-4-oxo-2-(R)-phenethyl-butyramide

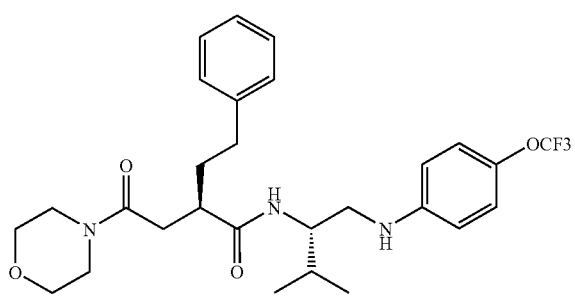

Compound is synthesized in accordance with Example 21. $^1$H NMR (CD$_3$OD, 400 MHz) δ 0.97 (d, J=6.8 Hz, 3H), 1.0 (d, J=6.8 Hz, 3H), 1.70-1.94 (m, 3H), 2.43 (dd, J=3.2, 14.8 Hz, 1H), 2.55-2.60 (m, 2H), 2.80 (m, 1H), 3.14 (dd, J=9.2, 13.2 Hz, 1H), 3.28 (m, 1H), 3.51-3.63 (m, 8H), 3.93 (m, 1H), 4.61 (bs, 1H), 6.60 (m, 2H0, 6.95(m, 2H), 7.05-7.18 (m, 5H). HPLC-MS calcd. for C$_{28}$H$_{36}$F$_3$N$_3$O$_4$ (M+H$^+$) 536.3, found 536.5.

Example 33

2-(R)-(2-Cyclopentyl-ethyl)-N-{2-methyl-1-(S)-[(4-trifluoromethoxy-phenylamino)-methyl]-propyl}-4-morpholin-4-yl-4-oxo-butyramide

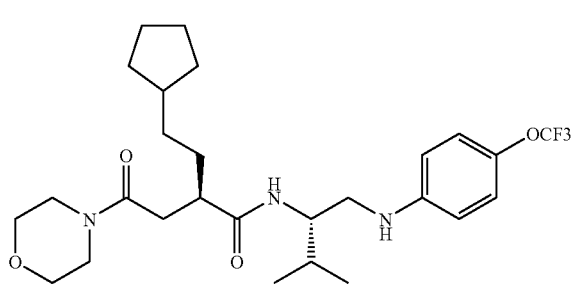

Compound is synthesized in accordance with Example 25 using allylcyclopentene.

$^1$H NMR (CD$_3$OD, 400 MHz) δ 0.97 (d, J=6.8 Hz, 3H), 1.0 (d, J=6.8 Hz, 3H), 1.30-1.69 (m, 12H), 1.90 (m, 1H), 2.38 (m, 1H), 2.75-2.82 (m, 2H), 3.11 (dd, J=8.4, 12.4 Hz, 1H), 3.26 (dd, J=4.4, 12.4 Hz, 1H), 3.54-3.67 (m, 8H), 3.89 (m, 1H), 6.59-6.65 (m, 2H), 6.97-7.00 (m, 2H). HPLC-MS calcd. for C$_{27}$H$_{40}$F$_3$N$_3$O$_4$ (M+H$^+$) 528.3, found 528.5.

Example 34

N-{2-Methyl-1-(S)-[(4-trifluoromethoxy-phenylamino)-methyl]-propyl}-4-morpholin-4-yl-4-oxo-2-(S)-phenyl-butyramide

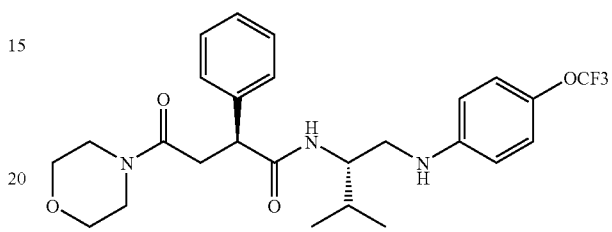

Compound is synthesized in accordance with Example 21. HPLC-MS calcd. for C$_{26}$H$_{32}$F$_3$N$_3$O$_4$ (M+H$^+$) 508.2, found 508.4.

Example 35

2-(S)-Cyclohexyl-N-{2-methyl-1-(S)-[(4-trifluoromethoxy-phenylamino)-methyl]-propyl}-4-morpholin-4-yl-4-oxo-butyramide

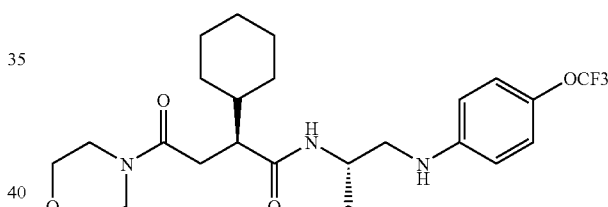

Compound is synthesized in accordance with Example 21. HPLC-MS calcd. for C$_{26}$H$_{38}$F$_3$N$_3$O$_4$ (M+H$^+$) 514.3, found 514.4.

Example 36

2-(R)-(2-Cyclopentyl-ethyl)-4-morpholin-4-yl-4-oxo-N-{1-(S)-[(4-trifluoromethoxy-phenylamino)-methyl]-propyl}-butyramide

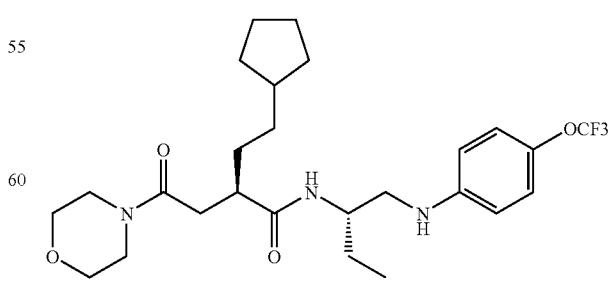

Compound is synthesized in accordance with Example 25. $^1$H NMR (CD$_3$OD, 400 MHz) δ 1.13(t, J=6.8 Hz, 3H), 1.14-

1.84 (m, 14H), 2.55 (dd, J=3.6, 14.8 Hz, 1H), 2.87-2.95 (m, 2H), 3.31 (d, J=6.8 Hz, 3.69-3.81 (m, 8H), 4.05 (m, 1H), 6.82-6.85 (m, 2H), 7.15-7.17 (m, 2H. HPLC-MS calcd. for $C_{26}H_{38}F_3N_3O_4$ (M+H$^+$) 514.3, found 514.3.

Example 37

2-(R)-(2-Cyclopentyl-ethyl)-4-morpholin-4-yl-4-oxo-N-{3-phenyl-1-(S)-[(4-trifluoromethoxy-phenylamino)-methyl]-propyl}-butyramide

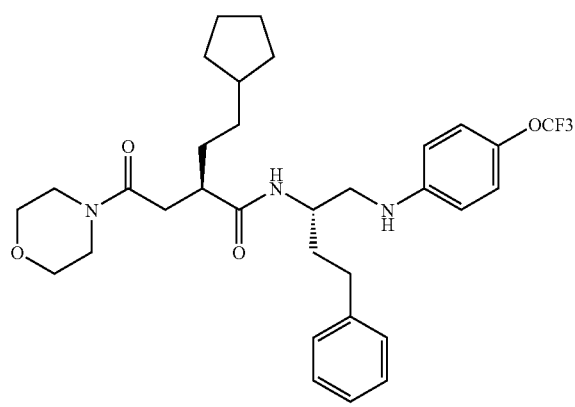

Compound is synthesized in accordance with Example 25. $^1$H NMR (CD$_3$OD, 400 MHz) δ 1.15(m, 2H), 1.47-2.10 (m, 14H), 5.57 (m, 1H), 2.70-2.99 (m, 3H), 3.12-3.35 (m, 2H), 3.69-3.84 (m, 8H), 4.20 (m, 1H), 6.80-6.82 (m, 2H), 7.14-7.16 (m, 2H), 7.31-7.40 (m, 5H). HPLC-MS calcd. for $C_{32}H_{42}F_3N_3O_4$ (M+H$^+$) 590.3, found 590.3.

Example 38

4-Morpholin-4-yl-4-oxo-2-(R)-phenethyl-N-{1-(S)-[(4-trifluoromethoxy-phenylamino)-methyl]-propyl}-butyramide

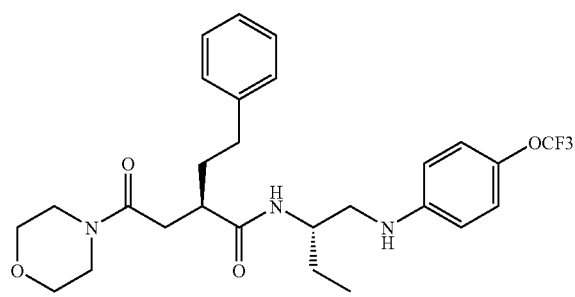

Compound is synthesized in accordance with Example 21. $^1$H NMR (CD$_3$OD, 400 MHz) δ 0.98(t, J=7.2 Hz, 3H), 1.45-1.90 (m, 4H), 2.40-2.50 (m, 1H), 2.58-2.62 (m, 2H), 2.80-2.82 (m, 2H), 3.19 (d, J=6.8 Hz, 2H), 3.51-3.65 (m, 8H), 3.95 (m, 1H), 6.68-6.70 (m, 2H), 6.98-6.99 (m, 2H), 7.00-7.21 (m, 5H). HPLC-MS calcd. for $C_{27}H_{34}F_3N_3O_4$ (M+H$^+$) 522.3, found 522.2.

Example 39

4-Morpholin-4-yl-4-oxo-2-(S)-phenyl-N-{1-(S)-[(4-trifluoromethoxy-phenylamino)-methyl]-butyl}-butyramide Compound is synthesized in accordance with Example 21. $^1$H NMR (CD$_3$OD, 400 MHz) δ 0.81(t, J=7.2 Hz, 3H), 1.20-1.43 (m, 4H), 2.52 (dd, J=4.8, 16 Hz, 1H), 2.85-2.95 (m, 2H), 3.11 (dd, J=10, 16 Hz, 1H), 3.38-3.50 (m, 8H), 3.86 (m, 1H), 3.92 (dd, J=4.8, 10.4 Hz, 1H), 6.34-6.36 (m, 2H), 6.78-6.80 (m, 2H), 7.15-7.26 (m, 5H). HPLC-MS calcd. for $C_{26}H_{32}F_3N_3O_4$ (M+H$^+$) 508.3, found 508.2.

Example 40

4-Morpholin-4-yl-4-oxo-2-(S)-phenyl-N-{3-phenyl-1-(S)-[(4-trifluoromethoxy-phenylamino)-methyl]-propyl}-butyramide Compound is synthesized in accordance with Example 21. $^1$H NMR (CD$_3$OD, 400 MHz) δ 1.76-1.90 (m, 2H), 2.58-2.65 (m, 2H), 2.72-2.77 (m, 1H), 3.00-3.10 (m, 2H), 3.24-3.30 (m, 1H), 3.49-3.66 (m, 8H), 3.97 (m, 1H), 4.09 (dd, J=4.8, 10.4 Hz, 1H), 5.43-6.46 (m, 2H), 6.87-6.89 (m, 2H), 7.18-7.40 (m, 10H). HPLC-MS calcd. for $C_{31}H_{34}F_3N_3O_4$ (M+H$^+$) 570.3, found 570.2.

Example 41

2-(S)-(4-Fluoro-phenyl)-N-{2-methyl-1-(S)-[(4-trifluoromethoxy-phenylamino)-methyl]-propyl}-4-morpholin-4-yl-4-oxo-butyramide

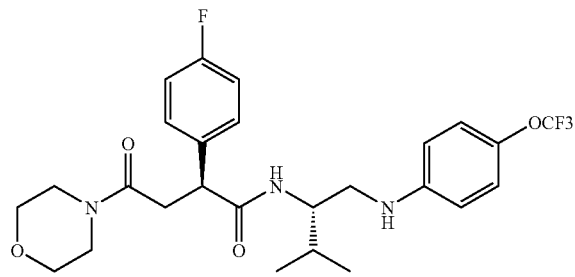

Compound is synthesized in accordance with Example 21. HPLC-MS calcd. for $C_{26}H_{31}F_4N_3O_4$ (M+H$^+$) 526.2, found 526.5.

Example 42

2-(S)-(4-Chloro-phenyl)-N-{2-methyl-1-(S)-[(4-trifluoromethoxy-phenylamino)-methyl]-propyl}-4-morpholin-4-yl-4-oxo-butyramide

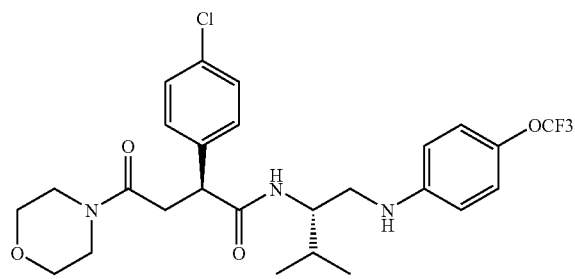

Compound is synthesized in accordance with Example 21. HPLC-MS calcd. for $C_{26}H_{31}ClF_3N_3O_4$ (M+H$^+$) 542.2, found 542.5.

Example 43

2-(R)-(4-Chloro-phenyl)-N-{2-methyl-1-(S)-[(4-trifluoromethoxy-phenylamino)-methyl]-propyl}-4-morpholin-4-yl-4-oxo-butyramide

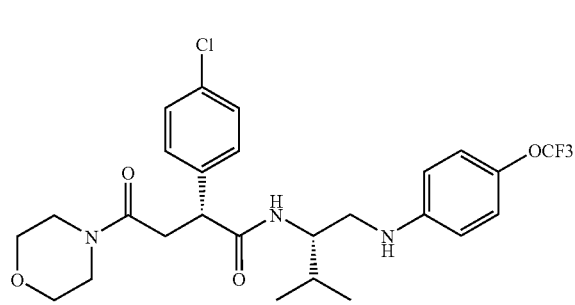

Compound is isolated as a minor side product from Example 42 synthesis. HPLC-MS calcd. for $C_{26}H_{31}ClF_3N_3O_4$ (M+H$^+$) 542.2, found 542.5.

Example 44

4-Morpholin-4-yl-4-oxo-2-(S)-phenyl-N-[1-(S)-phenyl-2-(4-trifluoromethoxy-phenylamino)-ethyl]-butyramide

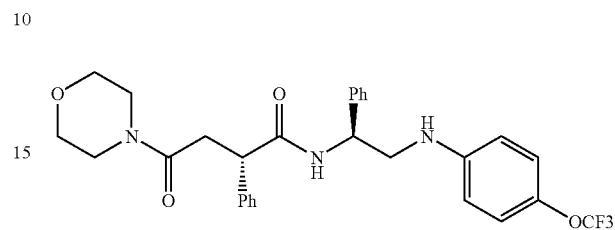

Compound is synthesized in accordance with Example 21. HPLC-MS calcd. for $C_{29}H_{30}F_3N_3O_4$ (M+H$^+$) 542.2, found 542.5.

Example 45

2-(R)-Cyclohexylmethyl-4-morpholin-4-yl-4-oxo-N-[1-(S)-phenyl-2-(4-trifluoromethoxy-phenylamino)-ethyl]-butyramide

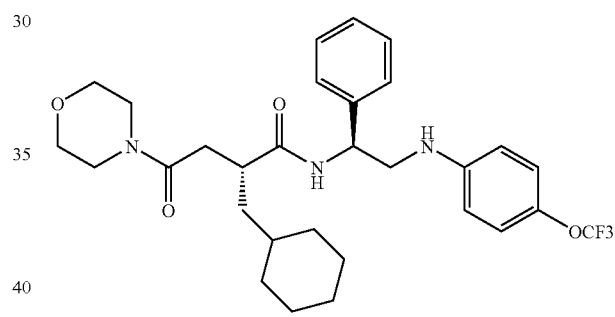

Compound is synthesized in accordance with Example 6. HPLC-MS calcd. for $C_{30}H_{38}F_3N_3O_4$ (M+H$^+$) 562.3, found 562.5.

Example 46

2-(R)-(2-Cyclopentyl-ethyl)-4-morpholin-4-yl-4-oxo-N-[1-(S)-phenyl-2-(4-trifluoromethoxy-phenylamino)-ethyl]-butyramide

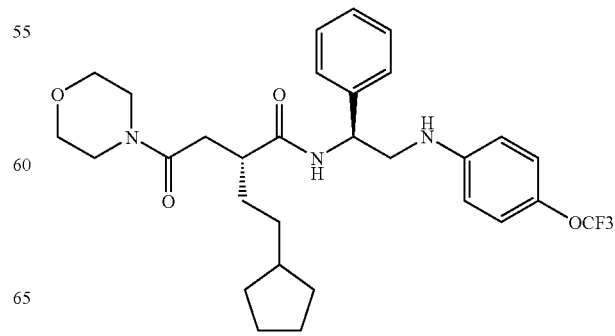

Compound is synthesized in accordance with Example 25. $^1$H NMR (CD$_3$OD, 400 MHz) δ 1.15-1.64 (m, 2H), 1.42-1.85 (m, 12H), 2.44 (dd, J=3.6, 10.8 Hz, 1H), 2.83-2.92 (m, 2H), 3.55-3.65 (m 9H), 5.28 (t, J=7.2 Hz, 1H), 6.77-6.80 (m, 2H), 7.12-7.14 (m, 2H), 7.39-7.53 (m, 5H). HPLC-MS calcd. for C$_{30}$H$_{38}$F$_3$N$_3$O$_4$ (M+H$^+$) 562.3, found 562.5.

Example 47

2-(R)-(2-Morpholin-4-yl-2-oxo-ethyl)-pent-4-enoic acid {2-methyl-1-(S)-[(4-trifluoromethoxy-phenylamino)-methyl]-propyl}-amide

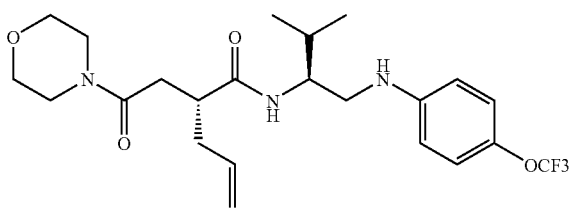

Compound is synthesized in accordance with Example 21. $^1$H NMR (CD$_3$OD, 400 MHz) δ 0.97(d, J=6.8 Hz, 3H), 0.98 (d, J=6.8 Hz, 3H), 1.88-1.93 (m, 1H), 2.15-2.32 (m, 2H), 2.40 (dd, J=4, 16 Hz, 1H), 2.73-2.82 (m, 1H), 2.85-2.90 (m, 1H), 31.0-3.13 (m, 1H), 3.24-3.31 (m, 1H), 3.51-3.67 (m, 8H), 3.90 (m, 1H), 4.97-5.08 (m, 2H), 5.74-5.81 (m, 1H), 6.61-6.63(m, 2H), 6.98-7.01 (m, 2H). HPLC-MS calcd. for C$_{23}$H$_{32}$F$_3$N$_3$O$_4$ (M+H$^+$) 472.3, found 472.2.

Example 48

2-(S)-(4-Chloro-phenyl)-4-morpholin-4-yl-4-oxo-N-[1-(S)-phenyl-2-(4-trifluoromethoxy-phenylamino)-ethyl]-butyramide

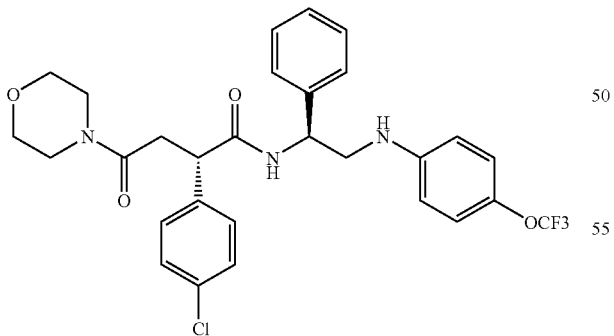

Compound is synthesized in accordance with Example 21. $^1$H NMR (CD$_3$OD, 400 MHz) δ 2.63(dd, J=4.4, 15.6 Hz, 1H), 3.26 (dd, J=10.0, 16 Hz, 1H), 3.42-3.69 (m, 9H), 4.14-4.21 (m, 1H), 5.13 (dd, J=6, 8.8 Hz, 1H), 6.50-6.53 (m, 2H), 6.97-7.00 (m, 2H), 7.27-7.52 (m, 10H). HPLC-MS calcd. for C$_{29}$H$_{29}$ClF$_3$N$_3$O$_4$ (M+H$^+$) 576.2, found 576.1.

Example 49

(R)-5,5-Dimethyl-2-(2-morpholin-4-yl-2-oxo-ethyl)-hexanoic acid [2-(5-methyl-isoxazol-3-ylamino)-ethyl]-amide

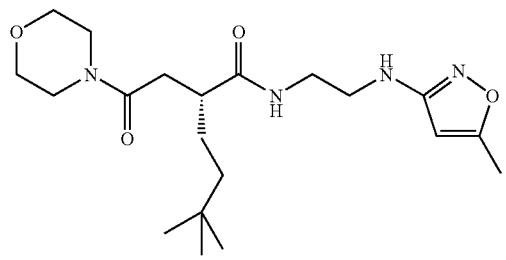

C$_{20}$H$_{34}$N$_4$O$_4$;HPLC-MS: 395.5 (M+H$^+$).

Example 50

2-(R)-Cyclohexylmethyl-4-(cis-2,6-dimethyl-morpholin-4-yl)-N-[1-(S)-methyl-2-(4-trifluoromethoxy-phenylamino)-ethyl]-4-oxo-butyramide

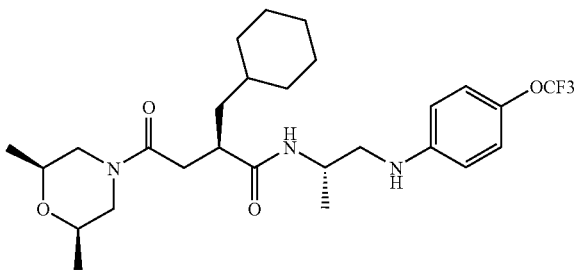

Compound is synthesized in accordance with Example 6, using cis-2,6-dimethylmorpholine. $^1$H NMR (CD$_3$OD, 400 MHz) δ 0.79-0.85 (m, 2H), 1.06-1.21 (m, 14H), 1.42-1.82 (m, 6H), 2.22-2.40 (m, 2H), 2.61-2.76 (m, 3H), 3.01-3.13 (m, 2H), 3.36-3.55 (m, 2H), 3.77-3.81 (m, 1H), 4.05 (m, 1H), 4.26-4.29 (m, 1H), 6.62-6.65 (m, 2H), 6.95-6.97 (m, 2H). HPLC-MS calcd. for C$_{27}$H$_{40}$F$_3$N$_3$O$_4$ (M+H$^+$) 528.3, found 528.6.

Example 51

2-(R)-Cyclohexylmethyl-N-[1-(S)-methyl-2-(4-trifluoromethoxy-phenylamino)-ethyl]-4-oxo-4-thiomorpholin-4-yl-butyramide

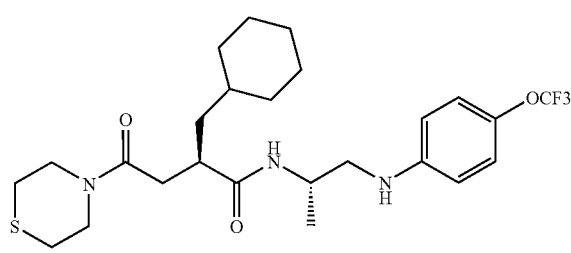

Compound is synthesized in accordance with Example 6, using thiomorpholine. $^1$H NMR (CD$_3$OD, 400 MHz) δ 0.81-0.85 (m, 2H), 1.08-1.23 (m, 5H), 1.19 (d, J=6.8 Hz, 3H), 1.42-1.83 (m, 6H), 2.35 (dd, J=4.4, 15.6 Hz, 1H), 2.50-2.76 (m, 6H), 3.09 (dd, J=5.6, 12.4 Hz, 1H), 3.20 (dd, J=7.6, 12.8 Hz, 1H), 3.66-3.85 (m, 4H), 4.01-4.07 (m, 1H), 6.73-6.75 (m, 2H), 7.01-7.03 (m, 2H). HPLC-MS calcd. for C$_{25}$H$_{36}$F$_3$N$_3$O$_4$ (M+H$^+$) 516.2, found 516.5.

Example 52

4-(4-Acetyl-piperazin-1-yl)-2-(R)-cyclohexylmethyl-N-[1-(S)-methyl-2-(4-trifluoromethoxy-phenylamino)-ethyl]-4-oxo-butyramide

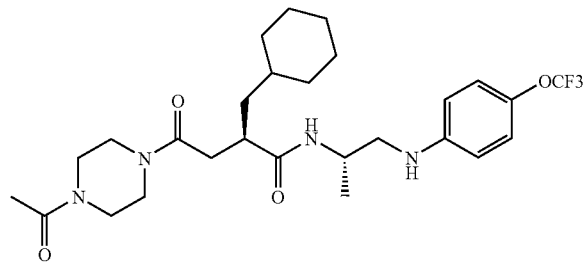

Compound is synthesized in accordance with Example 6, using 1-acetyl-piperazine. $^1$H NMR (CD$_3$OD, 400 MHz) δ 00.74-0.78 (m, 2H), 0.98-1.16 (m, 5H), 1.11 (d, J=6.8 Hz, 3H), 1.36-1.76 (m, 6H), 2.01 (s, 3H), 2.30-2.35 (m, 1H), 2.59-2.72 (m, 2H), 2.98 (dd, J=6.0, 12.8 Hz, 1H), 3.07-3.09 (m, 2H), 3.35-3.54 (m, 8H), 3.96-4.01 (m, 1H), 6.59-6.61 (m, 2H), 6.90-6.92 (m, 2H). HPLC-MS calcd. for C$_{27}$H$_{39}$F$_3$N$_3$O$_4$ (M+H$^+$) 541.3, found 541.6.

Example 53

2-(S)-(4-Methoxy-phenyl)-N-{2-methyl-1-(S)-[(4-trifluoromethoxy-phenylamino)-methyl]-propyl}-4-morpholin-4-yl-4-oxo-butyramide

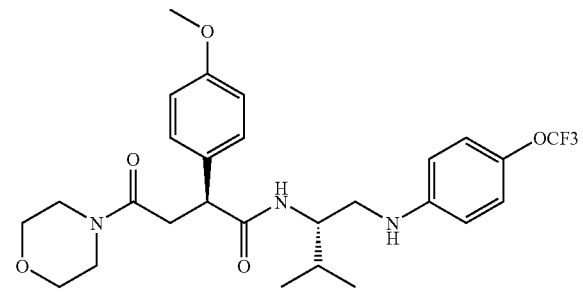

Compound is synthesized in accordance with Example 21. HPLC-MS calcd. for C$_{27}$H$_{34}$F$_3$N$_3$O$_5$ (M+H$^+$) 538.3, found 538.5.

Example 54

2-(R)-Cyclohexylmethyl-N-[2-(5-fluoro-3,3-dimethyl-2,3-dihydro-indol-1-yl)-1-(S)-methyl-ethyl]-4-morpholin-4-yl-4-oxo-butyramide

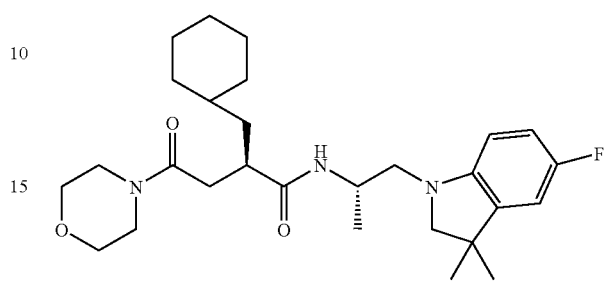

HPLC-MS for C$_{28}$H$_{42}$FN$_3$O$_3$ (M+1)=488.4.

Example 55

N-{2-Methyl-1-(S)-[(4-trifluoromethoxy-phenylamino)-methyl]-propyl}-4-morpholin-4-yl-4-oxo-2-(S)-(4-trifluoromethyl-phenyl)-butyramide

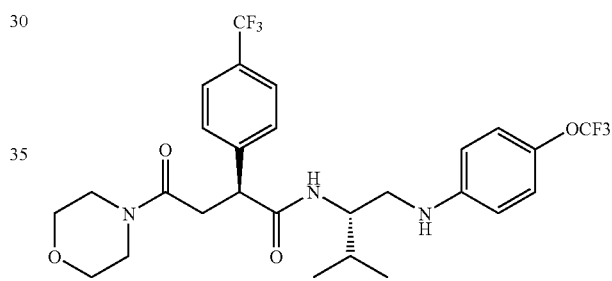

Compound is synthesized in accordance with Example 21. HPLC-MS calcd. for C$_{27}$H$_{31}$F$_6$N$_3$O$_4$ (M+H$^+$) 576.2, found 576.5.

Example 56

N-{2-Methyl-1-(S)-[(4-trifluoromethoxy-phenylamino)-methyl]-propyl}-4-morpholin-4-yl-4-oxo-2-(R)-(4-trifluoromethyl-phenyl)-butyramide

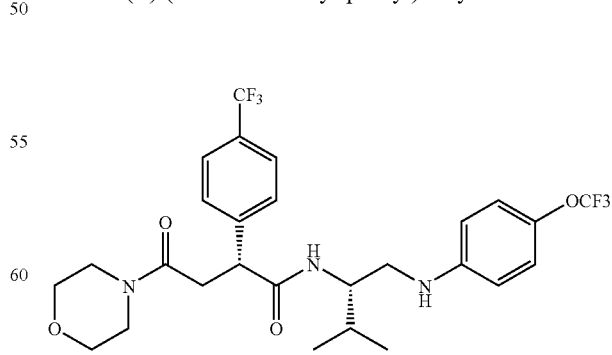

Compound is synthesized as a minor side product from the synthesis of Example 55. HPLC-MS calcd. for C$_{27}$H$_{31}$F$_6$N$_3$O$_4$ (M+H$^+$) 576.2, found 576.5.

Example 57

N-{2-Methyl-1-(S)-[(4-trifluoromethoxy-phenylamino)-methyl]-propyl}-4-morpholin-4-yl-4-oxo-2-(S)-p-tolyl-butyramide

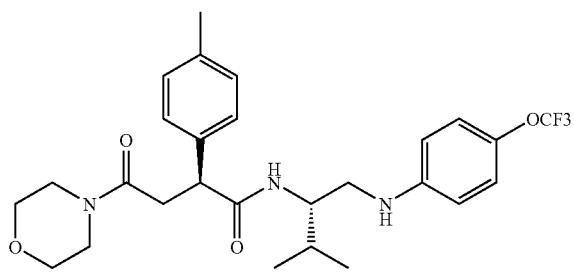

Compound is synthesized in accordance with Example 21. HPLC-MS calcd. for $C_{27}H_{34}F_3N_3O_4$ (M+H$^+$) 522.3, found 522.5.

Example 58

2-(R)-Cyclohexylmethyl-4-(1,1-dioxo-thiomorpholin-4-yl)-N-[1-(S)-methyl-2-(4-trifluoromethoxy-phenylamino)-ethyl]-4-oxo-butyramide

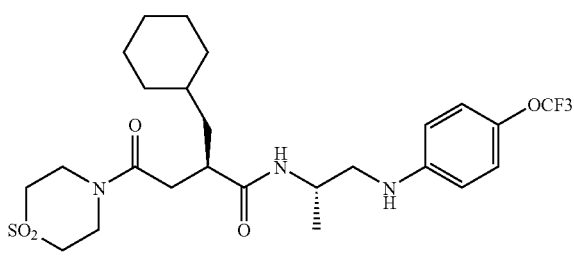

The compound was synthesized in a similar fashion to Example 6. An OXONE oxidation was employed title compound of Example 51 to furnish the sulfone. A procedure was used as described in McCarthy, J. R. et al. *Org. Synth.*, CV9, 446. $^1$H NMR (CD$_3$OD, 400 MHz) δ 0.73-0.79 (m, 2H), 1.00-1.19 (m, 7H), 1.10 (d, J=6.8 Hz), 1.34-1.75 (m, 6H), 2.34-2.37 (m, 1H), 2.64-2.71 (m, 2H), 2.94-3.08 (m, 7H), 3.79-4.01 (m, 5H), 6.53-6.56 (m, 2H), 6.87-6.89 (m, 2H). HPLC-MS calcd. for $C_{25}H_{36}F_3N_3O_5S$ (M+H$^+$) 548.2, found 548.2.

Example 59

2-(R)-(3-Ethyl-3-hydroxy-cyclohexylmethyl)-N-[1-(S)-methyl-2-(4-trifluoromethoxy-phenylamino)-ethyl]-4-morpholin-4-yl-4-oxo-butyramide

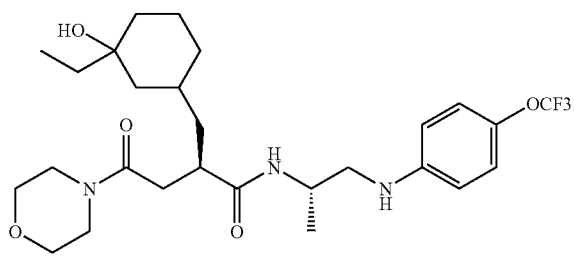

$^1$H NMR (CD$_3$OD, 400 MHz) δ 0.70(t, J=7.6 Hz, 3H), 0.95-1.57 (m, 13H), 1.12 (d, J=6.8 Hz, 3H), 2.30 (dd, J=4.4, 15.6 Hz, 1H), 2.58-2.64 (m, 1H), 2.72 (m, 1H), 3.00 (dd, J=5.2, 12.4 Hz, 1H), 3.07 (dd, J=7.6, 12.4 Hz, 1H), 3.38-3.57 (m, 8H), 4.02-4.04 (m, 1H), 6.58-6.61 (m, 2H), 6.91-6.93 (m, 2H). HPLC-MS calcd. for $C_{27}H_{40}F_3N_3O_5$ (M+H$^+$) 544.3, found 544.2.

Example 60

N-[1-(S)-Methyl-2-(4-trifluoromethoxy-phenylamino)-ethyl]-4-morpholin-4-yl-4-oxo-2-(S)-(4-trifluoromethyl-phenyl)-butyramide

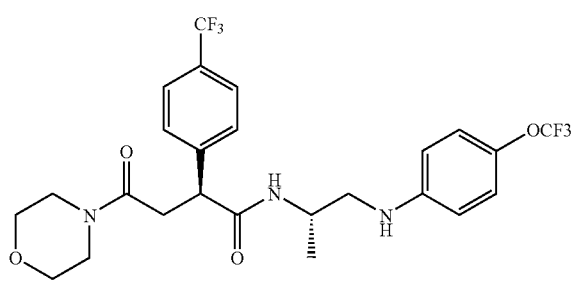

Compound is synthesized in accordance with Example 21. HPLC-MS calcd. for $C_{25}H_{27}F_6N_3O_4$ (M+H$^+$) 548.2, found 548.4.

Example 61

N-[1-(S)-Methyl-2-(4-trifluoromethoxy-phenylamino)-ethyl]-4-morpholin-4-yl-4-oxo-2-(S)-phenyl-butyramide

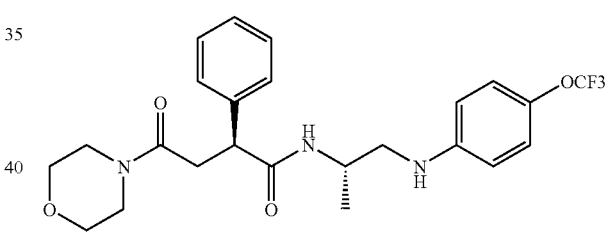

Compound is synthesized in accordance with Example 21. HPLC-MS calcd. for $C_{24}H_{28}F_3N_3O_4$ (M+H$^+$) 480.2, found 480.4.

Example 62

2-(S)-(4-Fluoro-phenyl)-N-[1-(S)-methyl-2-(4-trifluoromethoxy-phenylamino)-ethyl]-4-morpholin-4-yl-4-oxo-butyramide

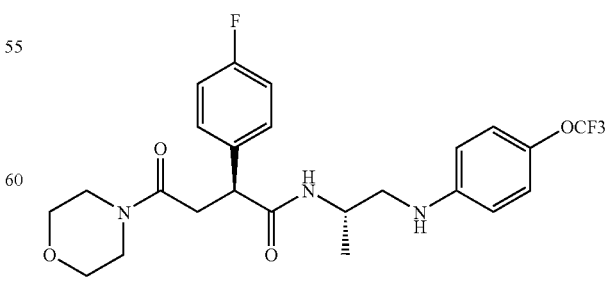

Compound is synthesized in accordance with Example 21. HPLC-MS calcd. for $C_{24}H_{27}F_4N_3O_4$ (M+H$^+$) 498.2, found 498.4.

Example 63

2-(S)-(4-Methoxy-phenyl)-N-[1-(S)-methyl-2-(4-trifluoromethoxy-phenylamino)-ethyl]-4-morpholin-4-yl-4-oxo-butyramide

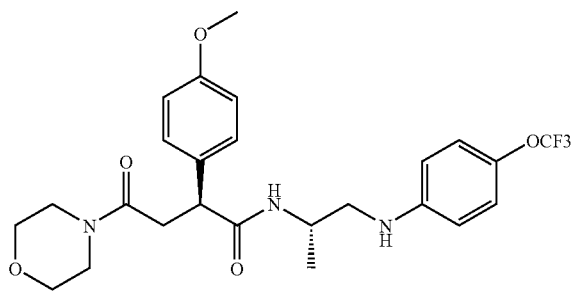

Compound is synthesized in accordance with Example 21. HPLC-MS calcd. for $C_{25}H_{30}F_3N_3O_5$ (M+H$^+$) 510.2, found 510.4.

Example 64

2-(S)-(4-Fluoro-phenyl)-N-{1-(S)-[(6-methoxy-pyridin-3-ylamino)-methyl]-2-methyl-propyl}-4-morpholin-4-yl-4-oxo-butyramide

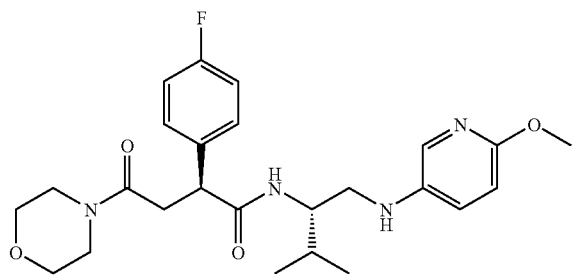

Step A: 2-(S)-(4-Fluoro-phenyl)-4-morpholin-4-yl-4-oxo-butyric acid (2.00 g, 7.11 mmol, 1.0 eq.), 2-(S)-Amino-3-methyl-butan-1-ol (1.59 g, 7.33 mmol, 1.03 eq.) and HATU (2.41 g, 7.33 mmol, 1.03 mmol) were dissolved in CH$_2$Cl$_2$ and stirred at room temperature. Diisopropylethylamine (3.9 mL, 21.98 mmol, 3.1 eq.) was added via syringe and the reaction is monitored by LC/MS. Upon completion, there reaction was evaporated and is diluted with ethyl acetate (100 mL) and extracted with 0.5M HCl (2×30 mL), saturated NaHCO$_3$, and brine. The organic layer is dried over MgSO$_4$, filtered and evaporated. Column chromatography (0-100%) EtOAc in hexane gradient provided 2-(S)-(4-Fluoro-phenyl)-N-(1-(S)-hydroxymethyl-2-methyl-propyl)-4-morpholin-4-yl-4-oxo-butyramide as a clear oil (1.06 g, 2.89 mmol, 41%). HPLC-MS calcd. for $C_{19}H_{27}FN_2O_4$ (M+H$^+$) 367.2, found 367.4; TLC (1:1 hexane/EtOAc) R$_f$=0.15.

Step B: 2-(S)-(4-Fluoro-phenyl)-N-(1-(S)-hydroxymethyl-2-methyl-propyl)-4-morpholin-4-yl-4-oxo-butyramide (2.31 g, 6.30 mmol, 1.0 eq.) was dissolved in CH$_2$Cl$_2$ (32 mL) and stirred at room temperature. Dess-Martin Periodinane (2.67 g, 6.30 mmol, 1.0 eq.) was added in one portion and the reaction is monitored by LC/MS and TLC. Upon completion, the reaction is diluted with EtOAc (200 mL) and extracted with 1M Na$_2$S$_2$O$_3$ (100 mL), NaHCO$_3$ (100 mL) and brine. The organic phase is dried over MgSO$_4$, filtered and evaporated to provide 2-(S)-(4-Fluoro-phenyl)-N-(1-(S)-formyl-2-methyl-propyl)-4-morpholin-4-yl-4-oxo-butyramide (1.41 g, 3.89 mmol, 62%) and used directly in the next step. HPLC-MS calcd. for $C_{19}H_{25}FN_2O_4$ (M+H$^+$) 365.2, found 365.4.

Step C: 2-(S)-(4-Fluoro-phenyl)-N-(1-(S)-formyl-2-methyl-propyl)-4-morpholin-4-yl-4-oxo-butyramide (350 mg, 0.96 mmol, 1.0 eq.) and 5-Amino-2-methoxy-pyridine (240 μL, 1.92 mmol, 2.0 eq.) dissolved in MeOH (2.5 mL) and acetic acid (106 mL, 1.92 mmol, 2.0 eq.) added via syringe at room temperature. Sodium cyanoborohydride (121 mg, 1.92 mmol, 2.0 eq.) added in portion and the reaction monitored the reaction by LC/MS. Upon completion, solvents were evaporated and dissolved in EtOAc (100 mL) washed with brine, dried over MgSO$_4$, filtered and evaporated. Purification by preparative mass-directed HPLC provided the title compound as a white solid after evaporation and lyophilization (2.6 mg, 5.6 □mol, 0.6%). HPLC-MS calcd. for $C_{25}H_{33}FN_4O_4$ (M+H$^+$) 473.3, found 473.5.

Example 65

N-[1-(S)-Methyl-2-(4-trifluoromethoxy-phenylamino)-ethyl]-4-morpholin-4-yl-4-oxo-2-(R)-spiro[2.5]oct-6-ylmethyl-butyramide

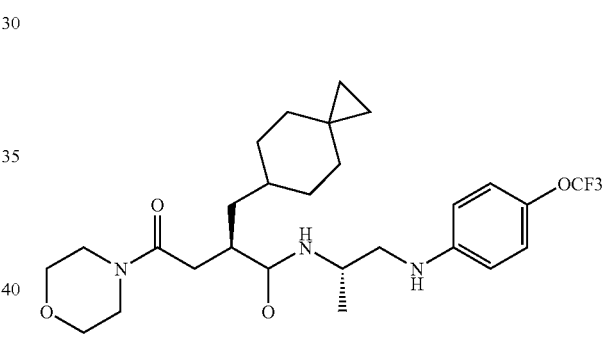

Step A: 4-Methylene-cyclohexanecarboxylic acid ethyl ester (9.0 g, 65.1 mmol, 91%) was synthesized, using a procedure from Della, E. W. et al. *J. Org. Chem.* 1993, 58, 2110, from commercially available 4-oxo-cyclohexanecarboxylic acid ethyl ester and used directly in the next reaction. $^1$H NMR (CHCl$_3$, 400 MHz) δ 1.23-1.27 (m, 3H), 1.55-1.62 (m, 2H), 1.97-2.09 (m, 4H), 2.31-2.46 (m, 3H), 4.09-4.19 (m, 2H), 4.64 (s, 2H).

Step B: The reduction reaction of 4-methylene-cyclohexanecarboxylic acid ethyl ester with LAH is as described in the above reference. The product was purified by distillation to provide (4-methylene-cyclohexyl)-methanol as clear oil (3.67 g, 29.09 mmol, 50% over Step A and B).

Step C: (4-methylene-cyclohexyl)-methanol was cyclopropanated, as described in Boehm, M. F. et al. *J. Med. Chem.* 1995, 38, 3146, to provide Spiro[2.5]oct-6-yl-methanol (340 mg, 2.42 mmol, 75%) as a pale yellow oil. $^1$H NMR (CHCl$_3$, 400 MHz) δ 0.17-0.27 (m, 4H), 0.88-0.91 (m, 2H), 1.09-1.25 (m, 2H), 1.52-1.54 (m, 2H), 1.69-1.75 (m, 3H), 3.49-3.51 (m, 2H).

Step D: Spiro[2.5]oct-6-yl-methanol (2.57 g, 18.3 mmol, 1.0 eq.) was dissolved in CH$_2$Cl$_2$ (30 mL) and placed in a ice-water bath at 0° C. Pyridinium dichromate (PCC) (7.9 g, 36.6 mmol, 2.0 eq.) was added and the reaction warmed to room temperature for 4 hours with stirring. The crude reaction was filtered through a Celite pad and washed with $CH_2Cl_2$ and evaporated. The crude material was dissolved in diethyl ether and filtered through Celite, washing with diethyl ether several times. Evaporated solvent to provide Spiro[2.5] octane-6-carbaldehyde as a brown oil (2.98 g, quantitative) that was used directly. $^1$H NMR ($CHCl_3$, 400 MHz) δ 0.17-0.27 (m, 4H), 0.88-0.91 (m, 2H), 1.09-1.25 (m, 2H), 1.52-1.54 (m, 2H), 1.69-1.75 (m, 3H), 9.44 (d, 1H, J=1.2 Hz).

4-(4-(S)-Benzyl-2-oxo-oxazolidin-3-yl)-4-oxo-3-(R)-spiro[2.5]oct-6-ylmethyl-butyric acid tert-butyl ester was prepared according to the procedures described in Example 26. A modified procedure was used for the t-Butyl ester deprotection from Trzeciak, A. et al. *Synthesis* 1996, 1443. 4-(4-(S)-Benzyl-2-oxo-oxazolidin-3-yl)-4-oxo-3-(R)-spiro [2.5]oct-6-ylmethyl-butyric acid tert-butyl ester (40 mg, 0.09 mmol, 1.0 eq.) was dissolved in dry dioxane (5 mL) under nitrogen followed by addition of $Et_3N$ (200 μL, 1.43 mmol, 16 eq.) and TMS-OTf (200 μL, 1.11 mmol, 12.3 eq.) via syringe. The reaction mixture stirred at room temperature overnight and then heated to 65° C. for 1.5 hours. Upon completion, 2 mL of water was added and volatiles were evaporated. The product was diluted with ethyl ether and extracted with water, and brine. The organic layer was dried over $MgSO_4$, filtered and evaporated to provide 4-(4-(S)-Benzyl-2-oxo-oxazolidin-3-yl)-4-oxo-3-(R)-spiro[2.5]oct-6-ylmethyl-butyric acid (50 mg, quantitative) as white solid and used directly in the next step. HPLC-MS calcd. for $C_{23}H_{29}NO_5$ (M+Na$^+$) 422.2, found 422.1. 4-(4-(S)-Benzyl-2-oxo-oxazolidin-3-yl)-4-oxo-3-(R)-spiro[2.5]oct-6-ylmethyl-butyric acid was converted to the title compound according to the procedures described in example 21.

N-[1-(S)-methyl-2-(4-trifluoromethoxy-phenylamino)-ethyl]-4-morpholin-4-yl-4-oxo-2-(R)-spiro[2,5]oct-6-ylm-ethyl-butyramide: $^1$H NMR ($CD_3OD$, 400 MHz) δ 0.05-0.10 (m, 4H), 0.63-1.63 (m, 10H), 1.05 (d, J=4.0 Hz, 3H), 2.23 (dd, J=4.8, 15.6 Hz, 1H), 2.55 (dd, J=9.6, 15.6 Hz, 1H), 2.65 (m, 1H), 2.92 (dd, J=6.0, 12.8 Hz, 1H), 3.02 (dd, J=7.2, 12.4 Hz, 1H), 3.32-3.51 (m, 8H), 3.92-3.96 (m, 1H), 6.50-6.53 (m, 2H), 6.81-6.85 (m, 2H). HPLC-MS calcd. for $C_{27}H_{38}F_3N_3O_4$ (M+H$^+$) 526.3, found 526.5.

Example 66

N-[2-(5-Fluoro-3,3-dimethyl-2,3-dihydro-indol-1-yl)-1-(S)-methyl-ethyl]-4-morpholin-4-yl-4-oxo-2-(S)-(4-trifluoromethyl-phenyl)-butyramide

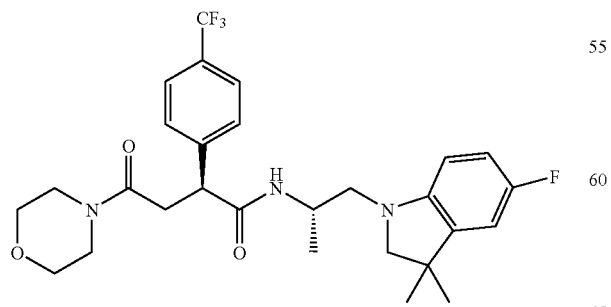

HPLC-MS for $C_{28}H_{33}F_4N_3O_3$ (M+1)=536.4.

Example 67

2-(S)-(4-Fluoro-phenyl)-N-{1-(S)-[(3-methanesulfo-nyl-phenylamino)-methyl]-2-methyl-propyl}-4-mor-pholin-4-yl-4-oxo-butyramide

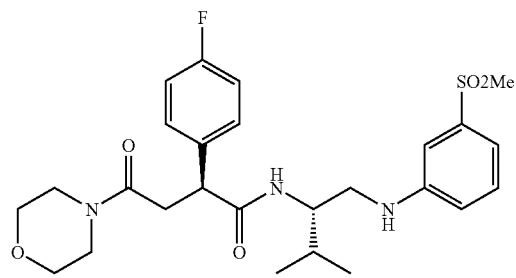

Compound is synthesized in accordance with Example 64. HPLC-MS calcd. for $C_{26}H_{34}FN_3O_5S$ (M+H$^+$) 520.2, found 520.5.

Example 68

N-[1-(S)-(5-Fluoro-3,3-dimethyl-2,3-dihydro-indol-1-ylmethyl)-2-methyl-propyl]-4-morpholin-4-yl-4-oxo-2-(S)-(4-trifluoromethyl-phenyl)-butyramide

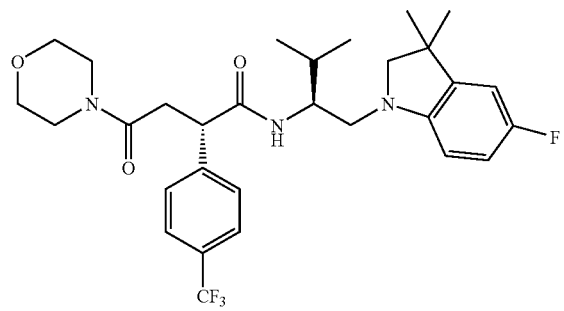

Compound is synthesized in accordance with Example 21. HPLC-MS calcd. for $C_{30}H_{37}F_4N_3O_3$ (M+H$^+$) 564.3, found 564.5.

Example 69

N-[1-(S)-Cyclopropyl-2-(5-fluoro-3,3-dimethyl-2,3-dihydro-indol-1-yl)-ethyl]-4-morpholin-4-yl-4-oxo-2-(S)-(4-trifluoromethyl-phenyl)-butyramide

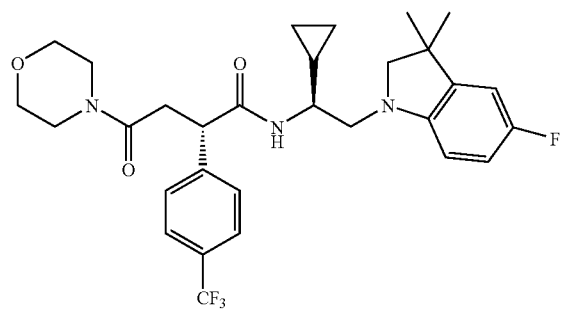

¹H NMR (CD₃OD, 400 MHz) δ 0.32-0.44 (m, 2H), 0.45-0.58 (m, 2H), 0.88 (s, 3H), 0.92-1.01 (m, 1H), 1.07 (s, 3H), 1.17-1.30 (m, 1H), 2.64 (dd, 1H, J=8.7, 17.3), 2.74 (d, 1H, J=8.4), 2.91 (d, 1H, J=8.8), 3.02 (dd, 1H, J=3.8, 13.8), 3.15-3.28 (m, 2H), 3.42-3.68 (m, 10H), 4.11 (dd, 1H, J=4.6, 9.8), 6.27 (dd, 1H, J=4.4, 8.0), 6.56-6.63 (m, 2H), 7.44 (d, 2H, J=8.0), 7.50 (d, 2H, J=8.4); HPLC-MS calcd. for $C_{30}H_{35}F_4N_3O_3$ (M+H⁺) 562.3, found 562.5.

Example 70

N-[1-(S)-Cyclopropyl-2-(4-trifluoromethoxy-phenylamino)-ethyl]-4-morpholin-4-yl-4-oxo-2-(S)-(4-trifluoromethyl-phenyl)-butyramide

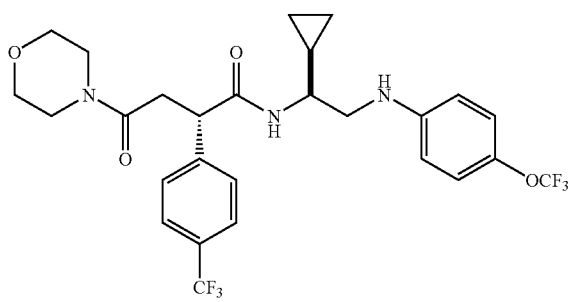

¹H NMR (400 MHz, MeOD) δ 7.43 (d, J=8.5 Hz, 2H), 7.40 (d, J=8.6 Hz, 2H), 6.74-6.79 (m, 2H), 6.30-6.36 (m, 2H), 4.00 (dd, J=10.1, 4.6 Hz, 1H), 3.30-3.57 (m, 8H), 3.17-3.26 (m, 1H), 3.00-3.15 (m, 3H), 2.53 (dd, J=16.2, 4.6 Hz, 1H), 0.80-0.90 (m, 1H), 0.38-0.45 (m, 1H), 0.28-0.36 (m, 1H), 0.13-0.23 (m, 2H); HPLC-MS calcd. for $C_{27}H_{29}F_6N_3O_4$ (M+H⁺) 574.5, found 574.4.

Example 71

2-(R)-(4-methanesulfonyl-phenyl)-N-{2-methyl-1-(S)-[(4-trifluoromethoxy-phenylamino)-methyl]-propyl}-4-morpholin-4-yl-4-oxo-butyramide

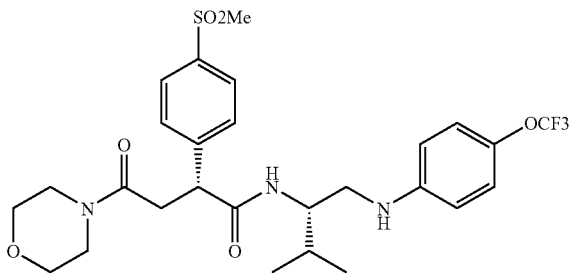

Compound is synthesized in accordance with Example 21 and isolated as a minor diastereomer. HPLC-MS calcd. for $C_{27}H_{34}F_3N_3O_6S$ (M+H⁺) 586.2, found 586.4.

Example 72

(S,S)-Morpholine-4-carboxylic acid {2-cyclohexyl-1-[2-(4-methoxy-phenylamino)-1-methyl-ethylcarbamoyl]-ethyl}-amide

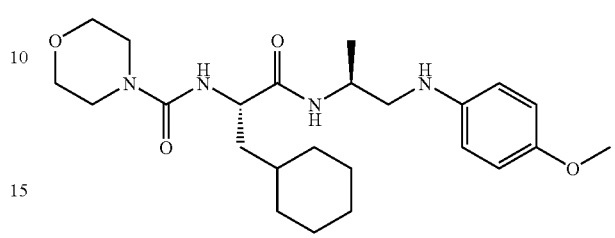

¹H NMR (CD₃OD, 400 MHz) δ 7.02 (d, J=8.6 Hz, 2H), 6.75 (dt, J=9.1, 3.5 Hz, 2H), 4.2 (dd, J=9, 6.8 Hz, 1H), 4.08 (dt, J=13, 6.8 Hz, 1H), 3.6 (m, 4H), 3.36 (m, 4H), 3.15 (m, 2H), 1.68 (m, 5H), 1.49 (m, 2H), 1.18 (d, J=6.8 Hz, 3H), 1.16 (m, 3H), 0.89 (m, 2H). HPLC-MS for $C_{24}H_{38}N_4O_4$ (M+1)=447.3.

Example 73

Morpholine-4-carboxylic acid {2-cyclopentyl-1-(S)-[2-(4-methoxy-phenylamino)-1-(S)-methyl-ethylcarbamoyl]-ethyl}-amide

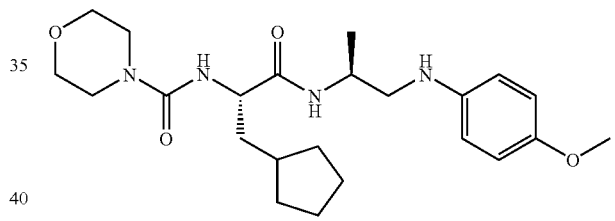

HPLC-MS for $C_{23}H_{36}N_4O_4$ (M+1)=433.3.

Example 74

Morpholine-4-carboxylic acid (2-cyclohexyl-1-(S)-{3-methanesulfonyl-1-(S)-[(4-trifluoromethoxy-phenylamino)-methyl]-propylcarbamoyl}-ethyl)-amide

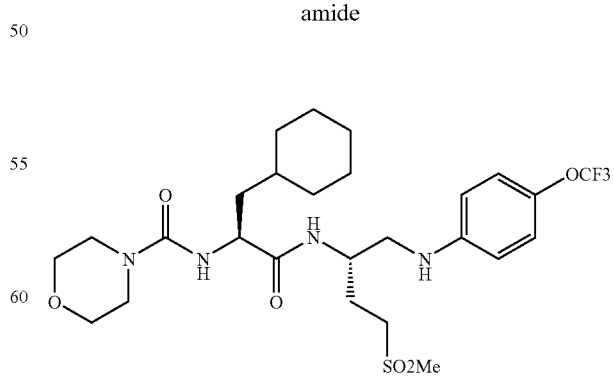

Compound is synthesized in accordance with Example 17. HPLC-MS calcd. for $C_{26}H_{39}F_3N_4O_6S$ (M+H⁺) 593.3, found 593.5.

Example 75

Morpholine-4-carboxylic acid (2-cyclohexyl-1(S)-{1-(S)-[(4-trifluoromethoxy-phenylamino)-methyl]-propylcarbamoyl}-ethyl)-amide

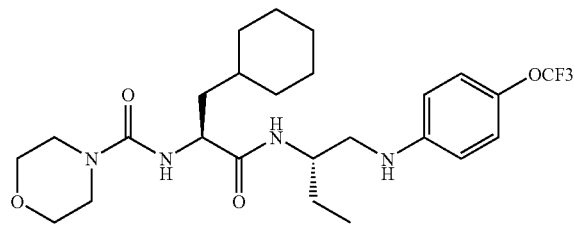

Compound is synthesized in accordance with Example 17. HPLC-MS calcd. for $C_{25}H_{37}F_3N_4O_4$ (M+H$^+$) 515.3, found 515.5.

Example 76

Morpholine-4-carboxylic acid {2-cyclohexyl-1-(S)-[2-methyl-1-(S)-(pyridin-3-ylaminomethyl)-propyl-carbamoyl]-ethyl}-amide

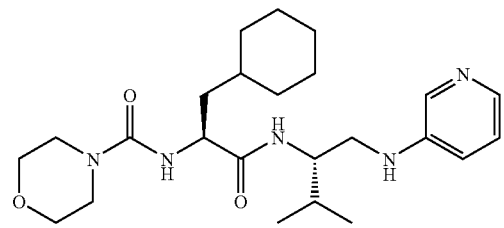

Compound is synthesized in accordance with Example 64. HPLC-MS calcd. for $C_{24}H_{39}N_5O_3$ (M+H$^+$) 446.3, found 446.4.

Example 77

Morpholine-4-carboxylic acid {2-cyclohexyl-1-(S)-[1-(S)-methyl-2-(5-methyl-isoxazol-3-ylamino)-ethylcarbamoyl]-ethyl}-amide $C_{21}H_{35}N_5O_4$; HPLC-MS: 422.5 (M+H$^+$).

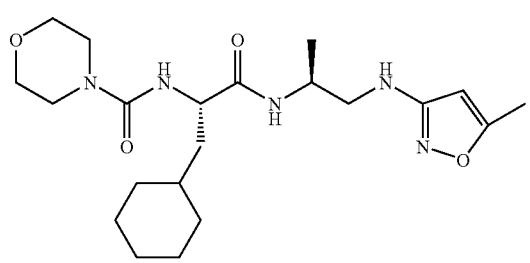

Example 78

Morpholine-4-carboxylic acid {1-(S)-[2-(benzothiazol-2-ylamino)-1-(S)-methyl-ethylcarbamoyl]-2-cyclohexyl-ethyl}-amide $C_{24}H_{35}N_5O_3S$; HPLC-MS: 474.5 (M+H$^+$).

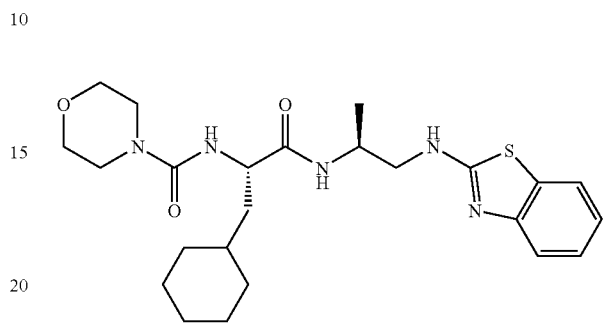

Example 79

Morpholine-4-carboxylic acid {1-(S)-[2-(benzooxazol-2-ylamino)-1-(S)-methyl-ethylcarbamoyl]-2-cyclohexyl-ethyl}-amide $C_{24}H_{35}N_5O_4$; HPLC-MS: 458.5 (M+H$^+$).

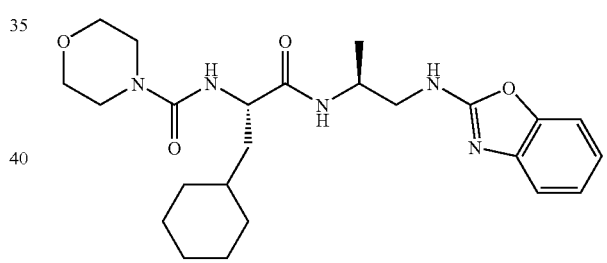

Example 80

(S,S)-Morpholine-4-carboxylic acid {2-cyclohexyl-1-[2-(5-fluoro-3,3-dimethyl-2,3-dihydro-indol-1-yl)-1-methyl-ethylcarbamoyl]-ethyl}-amide

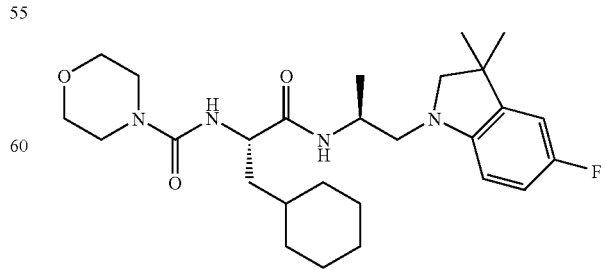

HPLC-MS for $C_{27}H_{41}FN_4O_3$ (M+1)=489.3.

Example 81

Morpholine-4-carboxylic acid {2-cyclohexyl-1-(S)-[1-(S)-cyclopropyl-2-(5-fluoro-3,3-dimethyl-2,3-dihydro-indol-1-yl)-ethylcarbamoyl]-ethyl}-amide

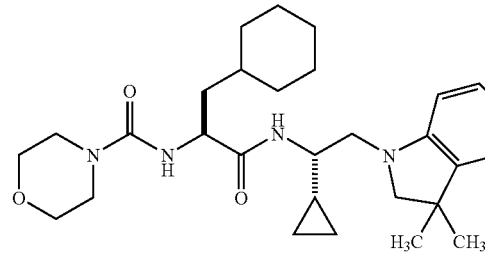

$^1$H NMR (400 MHz, MeOD) δ 7.85 (d, J=8.8 Hz, 1H), 6.70 (m, 2H), 6.44 (m, 1H), 6.26 (d, J=8.0 Hz, 1H), 4.27 (m, 1H), 3.62 (m, 3H), 3.53 (m, 1H), 3.26-3.38 (m, 7H), 3.09 (dd, J=8.4, 3.1 Hz, 1H), 3.04 (d, J=8.4 Hz, 1H), 1.57-1.76 (m, 5H), 1.27 (s, 3H), 1.23 (s, 3H), 1.04-1.50 (m, 6H), 0.96 (m, 1H), 0.76-0.89 (m, 2H), 0.56 (m, 1H), 0.45 (m, 1H), 0.34 (m, 2H); HPLC-MS calcd. for $C_{29}H_{43}FN_4O_3$ (M+H$^+$) 515.7, found 515.5.

Example 82

Morpholine-4-carboxylic acid {2-cyclohexyl-1-(S)-[1-(S)-cyclopropyl-2-(5-fluoro-3,3-spirocyclopropyl-2,3-dihydro-indol-1-yl)-ethylcarbamoyl]-ethyl}-amide

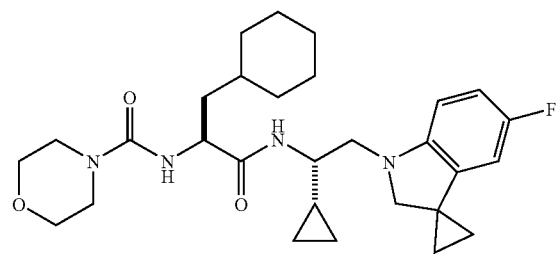

$^1$H NMR (400 MHz, MeOD) δ 7.85 (d, J=8.7 Hz, 1H), 6.65 (ddd, J=9.3, 9.3, 2.6 Hz, 1H), 6.40 (dd, J=8.5, 4.1 Hz, 1H), 6.31 (dd, J=8.5, 2.6 Hz, 1H), 6.23 (d, J=7.9 Hz, 1H), 4.26 (m, 1H), 3.62 (m, 4H), 3.50 (m, 2H), 3.36 (m, 10H), 3.14 (dd, J=13.8, 4.6 Hz, 1H), 1.66 (m, 4H), 1.43 (m, 1H), 1.34 (m, 1H), 1.15 (m, 2H), 0.819-1.08 (m, 6H), 0.56 (m, 1H), 0.46 (m, 1H), 0.34 (m, 2H); HPLC-MS calcd. for $C_{29}H_{42}FN_4O_3$ (M+H$^+$) 513.7, found 513.5.

Example 83

[1-(S)-Methyl-2-(4-trifluoromethoxy-phenylamino)-ethyl]-carbamic acid 1-(S)-cyclohexylmethyl-2-morpholin-4-yl-2-oxo-ethyl ester

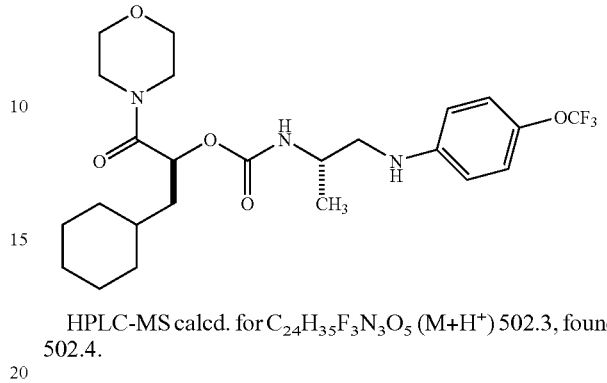

HPLC-MS calcd. for $C_{24}H_{35}F_3N_3O_5$ (M+H$^+$) 502.3, found 502.4.

Example 84

[1-(S)-Methyl-2-(4-trifluoromethoxy-phenylamino)-ethyl]-carbamic acid 3,3-dimethyl-1-(S)-(morpholine-4-carbonyl)-butyl ester

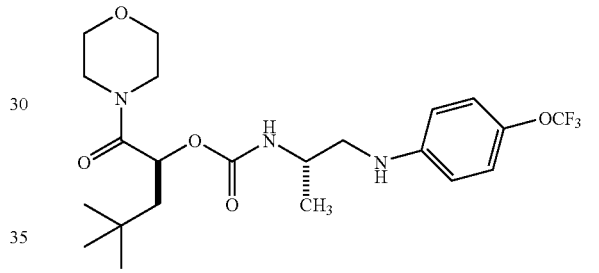

$^1$H NMR (400 MHz, CDCl$_3$) δ 7.00 (d, J=8.6 Hz, 2H), 6.56 (d, J=8.7 Hz, 2H), 5.38 (d, J=9.9 Hz, 1H), 4.04-4.20 (m, 1H), 3.87-3.97 (m, 1H), 3.42-3.80 (m, 8H), 3.10-3.20 (m, 1H), 1.81 (dd, J=15.0, 10.1 Hz, 1H), 1.42-1.50 (m, 1H), 1.24 (d, J=6.7 Hz, 3H), 0.95 (s, 9H); HPLC-MS calcd. for $C_{22}H_{33}F_3N_3O_5$ (M+H$^+$) 476.5, found 476.3.

Example 85

[2-(4-Difluoromethoxy-phenylamino)-1-(S)-methyl-ethyl]-carbamic acid 3,3-dimethyl-1-(S)-(morpholine-4-carbonyl)-butyl ester

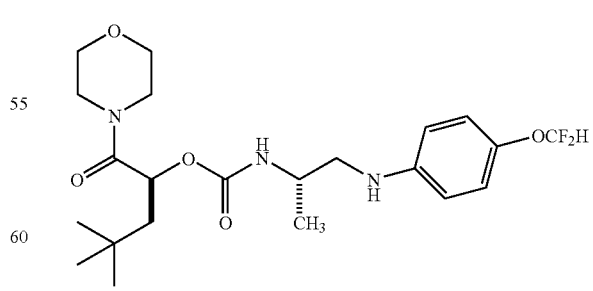

$^1$H NMR (400 MHz, CDCl$_3$) δ 6.92-6.96 (m, 2H), 6.53-6.58 (m, 2H), 6.358 (dd, J=42.6, 42.6 Hz, 1H), 5.35-5.41 (m, 1H), 3.98-4.13 (m, 1H), 3.84-3.98 (m, 1H), 3.40-3.80 (m, 8H), 3.10-3.20 (m, 1H), 1.81 (dd, J=14.9, 10.2 Hz, 1H), 1.42-1.50 (m, 1H), 1.24 (d, J=6.7 Hz, 3H), 0.95 (s, 9H); HPLC-MS calcd. for $C_{22}H_{34}F_2N_3O_5$ (M+H$^+$) 458.5, found 458.3.

Example 86

{2-Methyl-1-(S)-[(4-trifluoromethoxy-phenylamino)-methyl]-propyl}-carbamic acid 1-(S)-cyclohexylmethyl-2-morpholin-4-yl-2-oxo-ethyl ester

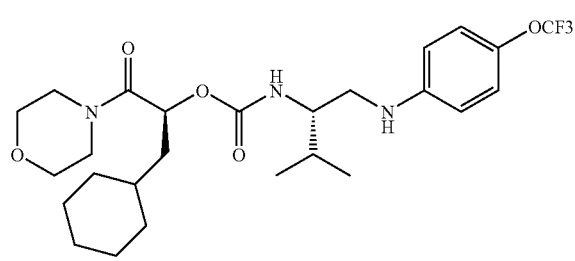

Compound is synthesized as outlined in example 5. HPLC-MS calcd. for $C_{26}H_{38}F_3N_3O_5$ (M+H$^+$) 530.3, found 530.5.

Example 87

{3-Phenyl-1-(S)-[(4-trifluoromethoxy-phenylamino)-methyl]-propyl}-carbamic acid 1-(S)-cyclohexylmethyl-2-morpholin-4-yl-2-oxo-ethyl ester

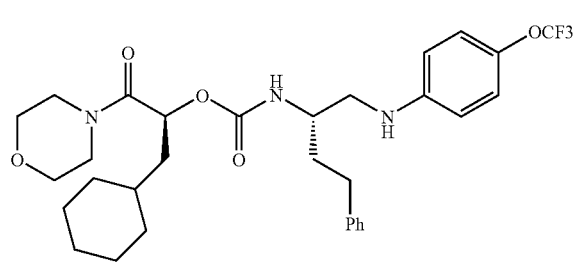

Compound is synthesized as outlined in example 5. HPLC-MS calcd. for $C_{31}H_{40}F_3N_3O_5$ (M+H$^+$) 592.3, found 592.6.

Example 88

{1-(S)-[(4-Trifluoromethoxy-phenylamino)-methyl]-butyl}-carbamic acid 1-(S)-cyclohexylmethyl-2-morpholin-4-yl-2-oxo-ethyl ester

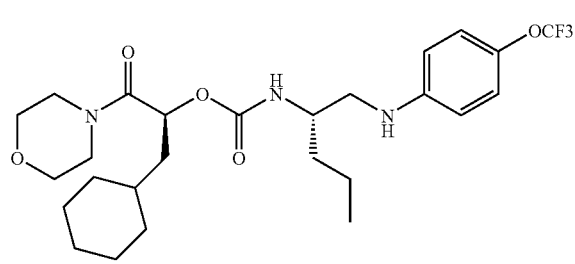

Compound is synthesized as outlined in example 5. HPLC-MS calcd. for $C_{26}H_{38}F_3N_3O_5$ (M+H$^+$) 530.3, found 530.5.

Example 89

[2-(4-Acetylsulfamoyl-phenylamino)-1-(S)-methyl-ethyl]-carbamic acid 1-(S)-cyclohexylmethyl-2-morpholin-4-yl-2-oxo-ethyl ester $C_{25}H_{38}N_4O_7S$; HPLC-MS: 539.5 (M+H$^+$).

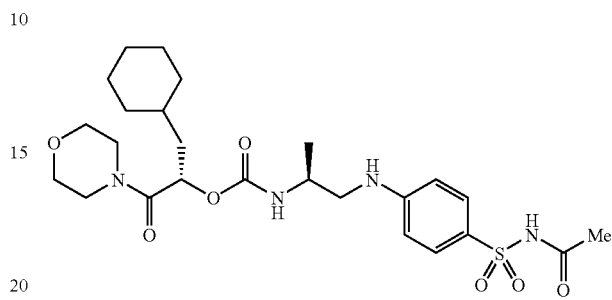

Example 90

[2-(5-Fluoro-2,2-dimethyl-2,3-dihydro-indol-1-yl)-1-(S)-methyl-ethyl]-carbamic acid 1-(S)-cyclohexylmethyl-2-morpholin-4-yl-2-oxo-ethyl ester

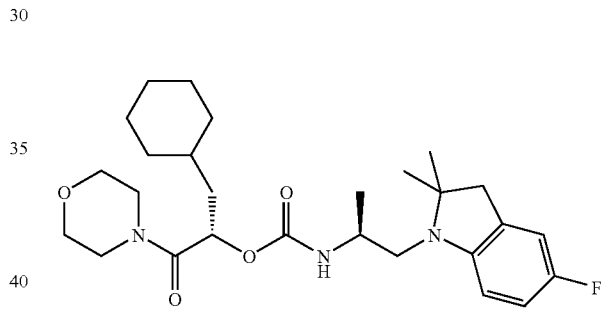

$C_{27}H_{40}FN_3O_4$; HPLC-MS: 490.6 (M+H$^+$).

Example 91

[1-(S)-Methyl-2-(5-methyl-isoxazol-3-ylamino)-ethyl]-carbamic acid 1-(S)-cyclohexylmethyl-2-morpholin-4-yl-2-oxo-ethyl ester

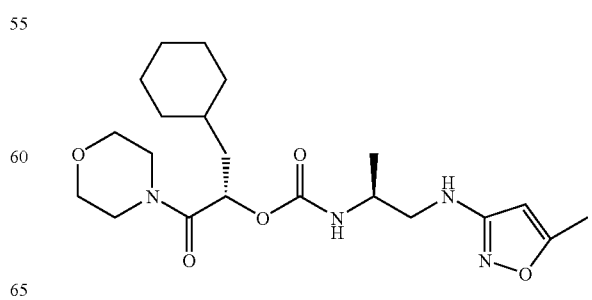

$C_{21}H_{34}N_4O_5$; HPLC-MS: 423.5 (M+H$^+$).

Example 92

(S,S)-[1-(5-Fluoro-3,3-dimethyl-2,3-dihydro-indol-1-yl-methyl)-propyl]-carbamic acid 1-cyclohexylmethyl-2-morpholin-4-yl-2-oxo-ethyl ester

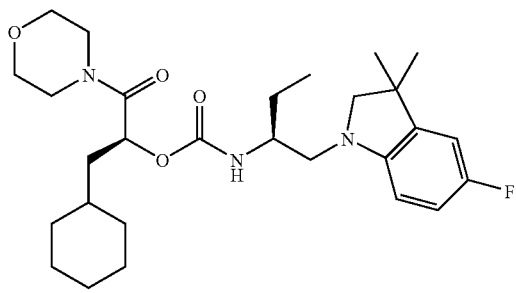

$^1$H NMR (CDCl$_3$, 400 MHz) δ 6.74 (m, 2H), 6.38 (s, 1H), 5.33 (d, J=7.86 Hz, 1H), 4.98 (s, 1H), 3.94 (m, 1H), 3.68 (m, 5H), 3.57 (m, 3H), 3.22 (d, J=8.35 Hz, 1H), 3.22 (d, J=8.35 Hz, 1H), 3.1 (m, 2H), 2.99 (dd, J=13.6, 6.8 Hz, 1H), 1.7 (m, 7H), 1.44 (m, 2H), 1.26 (m, 10H), 1.14 (m, 3H), 0.91 (m, 2H). HPLC-MS for C$_{27}$H$_{41}$FN$_4$O$_3$ (M+1)=504.3. (118636)

Example 93

[2-(5-Fluoro-2,2-dimethyl-2,3-dihydro-indol-1-yl)-1-(S)-methyl-ethyl]-carbamic acid 1-(S)-cyclohexylmethyl-2-(2,6-cis-dimethyl-morpholin-4-yl)-2-oxo-ethyl ester

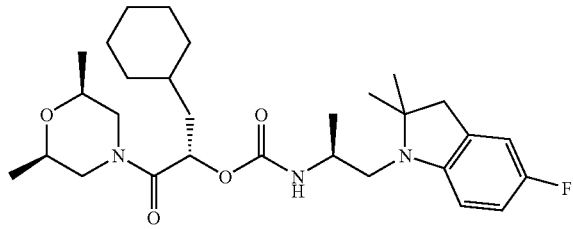

C$_{29}$H$_{44}$FN$_3$O$_4$; HPLC-MS: 518.6 (M+H$^+$); $^1$H-NMR (400 MHz) □ (DMSO-D$_6$) 7.23(m, 1H), 6.79 (m, 1H), 6.68 (m, 1H), 6.35 (m, 1H), 5.19 (m, 1H), 4.11 (m, 1H), 3.66 (m, 2H), 2.79 (m, 1H), 2.62 (m, 4H), 2.19 (m, 1H), 1.70 (m, 1H), 1.53 (m, 4H); 1.24 (m, 3H); 1.02 (m, 18H), 0.88 (m, 2H).

Example 94

(S,S)-[2-(5-Fluoro-2,2-dimethyl-2,3-dihydro-indol-1-yl)-1-methyl-ethyl]-carbamic acid 2-(4-acetyl-piperazin-1-yl)-1-cyclohexylmethyl-2-oxo-ethyl ester

C$_{29}$H$_{43}$FN$_4$O$_4$; HPLC-MS: 531.7 (M+H$^+$).

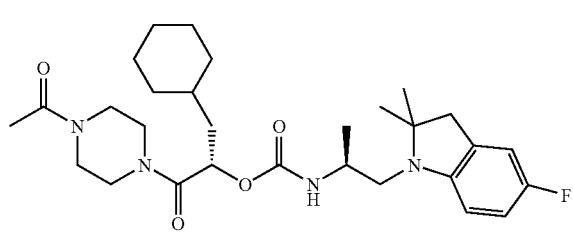

Example 95

[2-(5-Fluoro-2,2-dimethyl-2,3-dihydro-indol-1-yl)-1-(S)-methyl-ethyl]-carbamic acid 1-(S)-cyclohexylmethyl-2-(4-methanesulfonyl-piperazin-1-yl)-2-oxo-ethyl ester

C$_{28}$H$_{43}$FN$_4$O$_5$S; HPLC-MS: 567.6 (M+H$^+$).

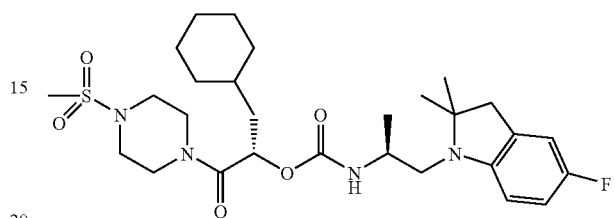

Example 96

[2-(5-Fluoro-2,2-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester

C$_{27}$H$_{40}$FN$_3$O$_3$S; HPLC-MS: 506.5 (M+H$^+$).

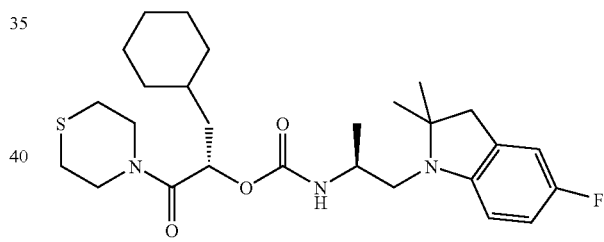

Example 97

[2-(5-Fluoro-3,3-dimethyl-2,3-dihydro-indol-1-yl)-1-(S)-methyl-ethyl]-carbamic acid 1-(S)-cyclohexylmethyl-2-(2,6-cis-dimethyl-morpholin-4-yl)-2-oxo-ethyl ester

C$_{29}$H$_{44}$FN$_3$O$_4$; HPLC-MS: 518.6 (M+H$^+$).

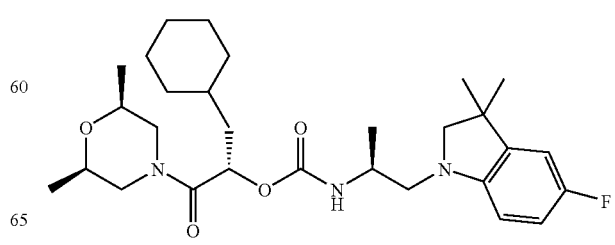

Example 98

[2-(5-Fluoro-3,3-dimethyl-2,3-dihydro-indol-1-yl)-1-(S)-methyl-ethyl]-carbamic acid 2-(4-acetyl-piperazin-1-yl)-1-(S)-cyclohexylmethyl-2-oxo-ethyl ester $C_{29}H_{43}FN_4O_4$; HPLC-MS: 531.7 (M+H$^+$).

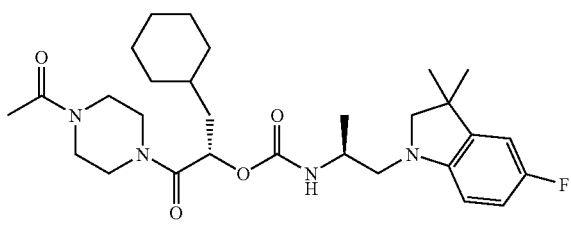

Example 99

[2-(5-Fluoro-3,3-dimethyl-2,3-dihydro-indol-1-yl)-1-(S)-methyl-ethyl]-carbamic acid 1-(S)-cyclohexylmethyl-2-(4-methanesulfonyl-piperazin-1-yl)-2-oxo-ethyl ester $C_{28}H_{43}FN_4O_5S$; HPLC-MS: 567.6 (M+H$^+$).

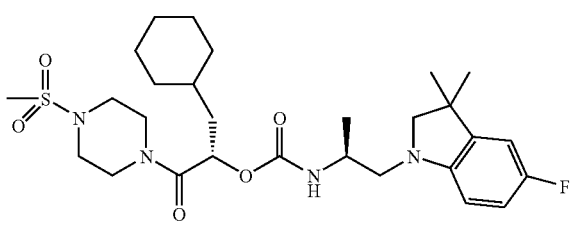

Example 100

[2-(5-Fluoro-3,3-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester $C_{27}H_{40}FN_3O_3S$; HPLC-MS: 506.5 (M+H$^+$).

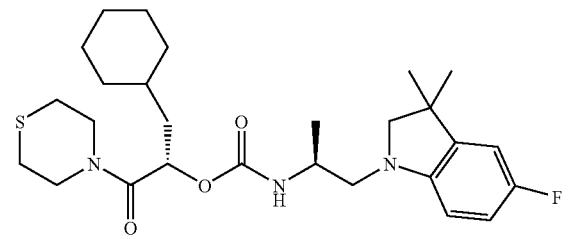

Example 101

[2-(5-Fluoro-3,3-spiro-cylopropyl-2,3-dihydro-indol-1-yl)-1-(S)-methyl-ethyl]-carbamic acid 1-(S)-cyclohexylmethyl-2-morpholin-4-yl-2-oxo-ethyl ester

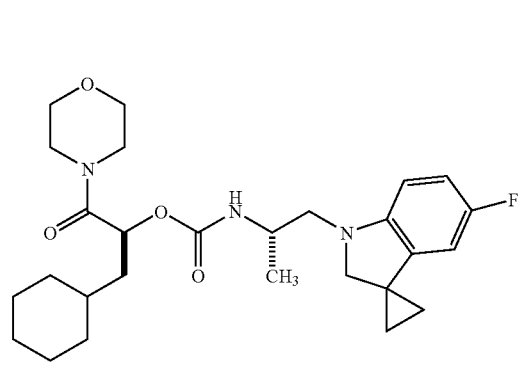

$^1$H NMR (400 MHz, MeOD) δ 6.66 (m, 1H), 6.41 (dd, J=8.5, 4.1 Hz, 1H), 6.32 (dd, J=8.5, 2.5 Hz, 1H), 5.24 (m, 1H), 3.83 (m, 1H), 3.45-3.77 (m, 10H), 3.41 (d, J=8.6 Hz, 1H), 3.15 (dd, J=13.7, 7.0 Hz, 1H), 3.00 (dd, J=13.7, 5.8 Hz, 1H), 1.59-1.81 (m, 6H), 1.37-1.50 (m, 2H), 1.21 (d, J=6.8 Hz, 3H), 1.12-1.26 (m, 3H), 0.95 (m, 6H); HPLC-MS calcd. for $C_{27}H_{39}FN_3O_4$ (M+H$^+$) 488.6, found 488.4.

Example 102

[2-(5-Fluoro-3,3-dimethyl-2,3-dihydro-indol-1-yl)-1-(S)-methyl-ethyl]-carbamic acid 1-(S)-cyclohexylmethyl-2-oxo-2-piperidin-1-yl-ethyl ester $C_{28}H_{42}FN_3O_3$; HPLC-MS: 488.5 (M+H$^+$).

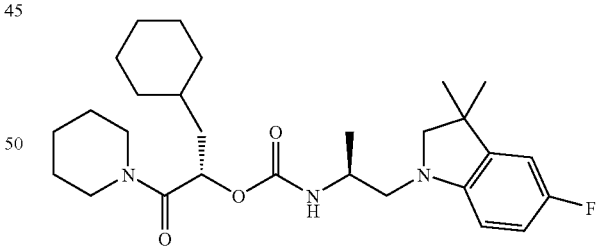

Example 103

[2-(5-Fluoro-3,3-dimethyl-2,3-dihydro-indol-1-yl)-1-(S)-methyl-ethyl]-carbamic acid 1-(S)-cyclohexylmethyl-2-oxo-2-pyrrolidin-1-yl-ethyl ester $C_{27}H_{40}FN_3O_3$; HPLC-MS: 474.5 (M+H$^+$).

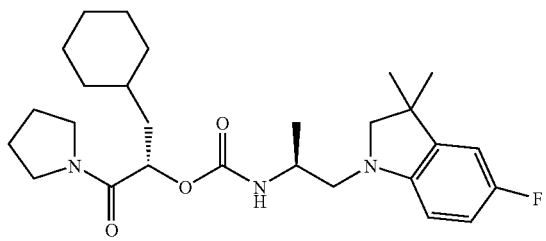

Example 104

[2-(5-Fluoro-3,3-dimethyl-2,3-dihydro-indol-1-yl)-1-(S)-methyl-ethyl]-carbamic acid 2-cyclohexyl-1-(S)-dimethylcarbamoyl-ethyl ester $C_{25}H_{38}FN_3O_3$; HPLC-MS: 448.5 (M+H$^+$).

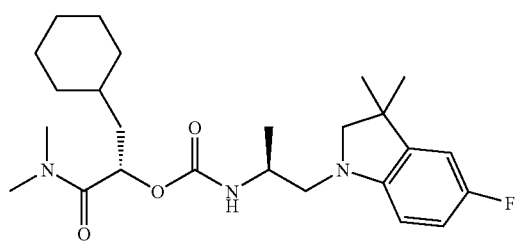

Example 105

[2-(5-Fluoro-3,3-dimethyl-2,3-dihydro-indol-1-yl)-1-(S)-methyl-ethyl]-carbamic acid 1-(S)-cyclohexylmethyl-2-(1,1-dioxo-1λ$^6$-thiomorpholin-4-yl)-2-oxo-ethyl ester $C_{27}H_{40}FN_3O_5S$; HPLC-MS: 538.5 (M+H$^+$).

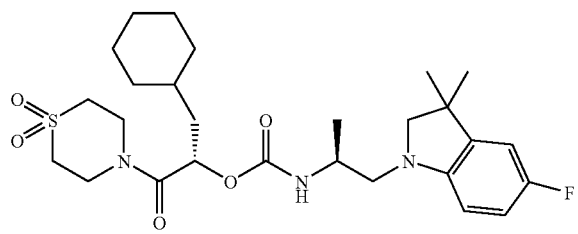

Example 106

[2-(5-Fluoro-3,3-dimethyl-2,3-dihydro-indol-1-yl)-1-(S)-methyl-ethyl]-carbamic acid 2-cyclohexyl-1-(S)-[(2-methoxy-ethyl)-methyl-carbamoyl]-ethyl ester $C_{27}H_{42}FN_3O_4$; HPLC-MS: 491.5 (M+H$^+$).

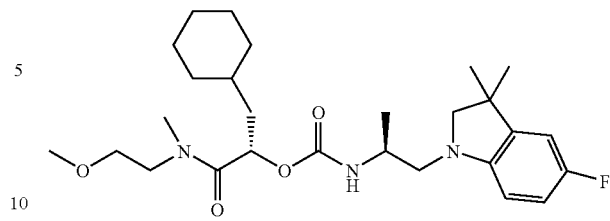

Example 107

[2-(5-Fluoro-3,3-dimethyl-2,3-dihydro-indol-1-yl)-1-(S)-methyl-ethyl]-carbamic acid 2-azetidin-1-yl-1-(S)-cyclohexylmethyl-2-oxo-ethyl ester $C_{26}H_{38}FN_3O_3$; HPLC-MS: 460.5 (M+H$^+$)

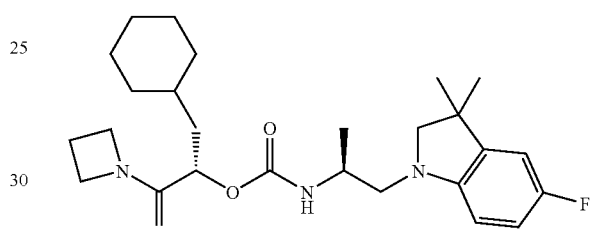

Example 108

[2-(S)-Cyclopropyl-2-(5-fluoro-3,3-dimethyl-2,3-dihydro-indol-1-yl)-ethyl]-carbamic acid 1-(S)-cyclohexylmethyl-2-morpholin-4-yl-2-oxo-ethyl ester

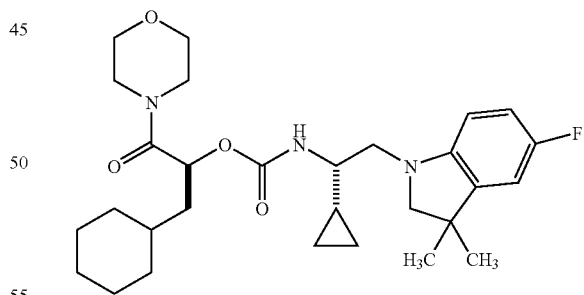

$^1$H NMR (400 MHz, CDCl$_3$) δ 6.67-6.74 (m, 2H), 6.34-6.41 (m, 1H), 5.27-5.33 (m, 1H), 5.03-5.09 (m, 1H), 3.40-3.75 (m, 8H), 3.13-3.26 (m, 4H), 1.55-1.81 (m, 6H), 1.30-1.46 (m, 2H), 1.26 (s, 3H), 1.24 (s, 3H), 1.03-1.25 (m, 3H), 0.78-0.99 (m, 3H), 0.43-0.58 (m, 2H), 0.27-0.41 (m, 2H); HPLC-MS calcd. for $C_{29}H_{43}FN_3O_4$ (M+H$^+$) 516.3, found 516.5.

Example 109

[2-(S)-(5-Fluoro-3,3-dimethyl-2,3-dihydro-indol-1-ylmethyl)-2-methyl-propyl]-carbamic acid 2-morpholin-4-yl-2-oxo-1-(R,S)-phenyl-ethyl ester

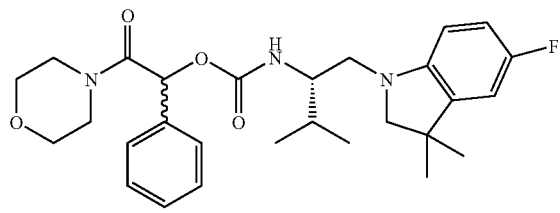

Compound is synthesized as outlined in example 5 using (L)-mandelic acid. The 5 compound is isolated as a mixture of diastereomers. HPLC-MS calcd. for $C_{28}H_{36}FN_3O_4$ (M+H$^+$) 498.3, found 498.3.

Example 110

[2-(S)-(5-Fluoro-3,3-dimethyl-2,3-dihydro-indol-1-ylmethyl)-2-methyl-propyl]-carbamic acid 2-morpholin-4-yl-2-oxo-1-(R)-phenylmethanesulfonylmethyl-ethyl ester onic acid methyl ester 110b (7.41 g, 31.41 mmol, 92%) was isolated as a viscous oil: MS calcd. for $C_{11}H_{14}O_3S$ (M+H$^+$) 227.1, found 227.3.

Step B: This reaction was performed as previously described by Deechongkit, S.; You, S.-L.; Kelly, J. W. *Org. Lett.* 2004, 6, 497, using (R)-3-Benzylsulfanyl-2-hydroxy-propionic acid methyl ester 110b and lithium hydroxide. (R)-3-Benzylsulfanyl-2-hydroxy-propionic acid 110c (3.08 g, 14.51 mmol, 46%) was isolated as a viscous oil: MS calcd. for $C_{10}H_{12}O_3S$ (M+Na$^+$) 235.1, found 235.3.

Step C: This reaction was performed as previously described in example 5, using (R)-3-Benzylsulfanyl-2-hydroxy-propionic acid 110c. (R)-3-Benzylsulfanyl-2-hydroxy-1-morpholin-4-yl-propan-1-one 110d (3.41 g, 11.87 mmol, 67%) was isolated as a viscous oil: MS calcd. for $C_{14}H_{19}NO_3S$ (M+H$^+$) 282.1, found 282.4.

Step D: Oxone (2 KHSO$_5$.KHSO$_4$.K$_2$SO$_4$) (10.55 g, 17.17 mmol, 3.0 eq.) was dissolved in H$_2$O (25 mL, 0.7 M) and added to a MeOH (25 mL, 0.3 M) solution of (R)-3-Benzylsulfanyl-2-hydroxy-1-morpholin-4-yl-propan-1-one 110d (1.61 g, 5.73 mmol, 1.0 eq.) at 0° C. over a 30 minute period. The reaction was monitored to completion by LC/MS. After the reaction was judged to be complete (~12 h), the MeOH was evaporated in vacuo. The resulting solution was diluted with H$_2$O (30 mL) and extracted with CH$_2$Cl$_2$ (3×50 mL). The organic extracts were combined, washed with H$_2$O (75 mL) and saturated NaCl (50 mL). The organic layer was dried over MgSO$_4$ and filtered. The organic solvent was removed in vacuo and provided (R)-2-Hydroxy-1-morpholin-4-yl-3-phenylmethanesulfonyl-propan-1-one 110e as a viscous oil (1.60 g, 5.11 mmol, 89%) which was used directly without further purification: MS calcd. for $C_{14}H_{19}NO_5S$ (M+H$^+$) 314.1, found 314.3.

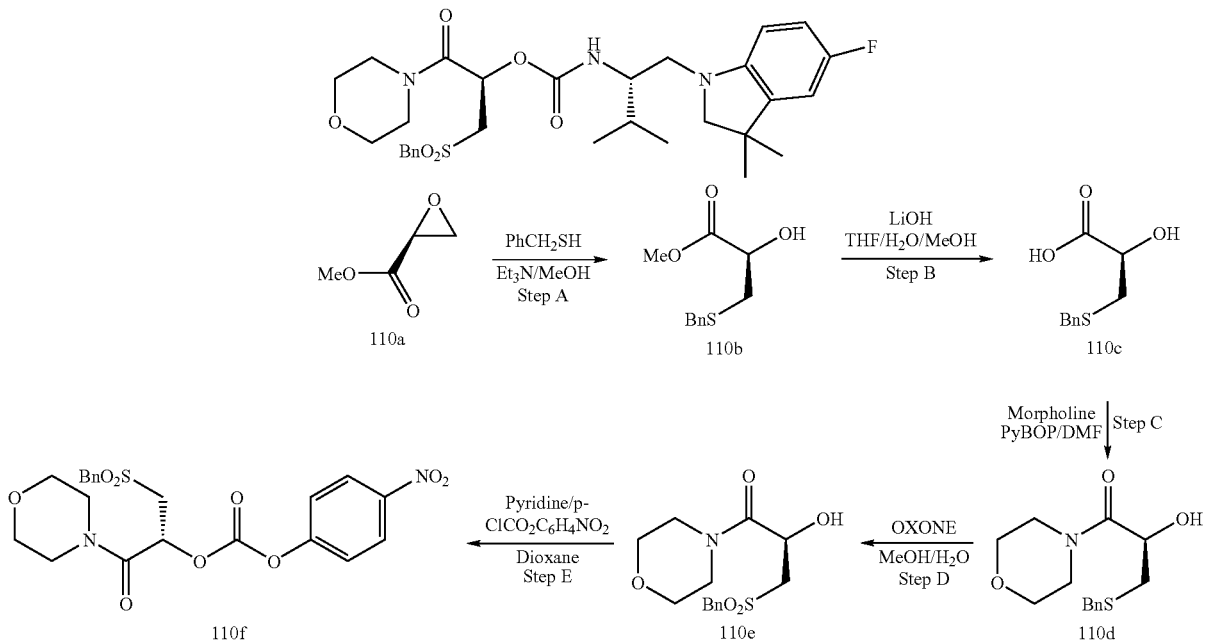

Step A: This reaction was performed as previously described by Deechongkit, S.; You, S.-L.; Kelly, J. W. *Org. Lett.* 2004, 6, 497, using (S)-Methylglycidate 110a and Benzyl 15 mercaptan. (R)-3-Benzylsulfanyl-2-hydroxy-propi- Step E: This reaction was performed as previously described example 5, using (R)-2-Hydroxy-1-morpholin-4-yl-3-phenylmethanesulfonyl-propan-1-one 110e. (R)—Carbonic acid 2-morpholin-4-yl-2-oxo-1-phenylmethanesulfonylmethyl-ethyl ester 4-nitro-phenyl ester 110f (1.98 g, 4.14 mmol, 81%) was isolated as a white solid after column chromotography: MS calcd. for $C_{21}H_{22}N_2O_9S$ (M+H$^+$) 479.1, found 479.3.

From the mixed carbonate, the title compound is prepared according to the procedures described in example 5 and isolated as a white solid: HPLC-MS calcd. for $C_{30}H_{40}FN_3O_6S$ (M+H$^+$) 590.3, found 590.2.

Example 111

[1-(S)-(5-Fluoro-3,3-dimethyl-2,3-dihydro-indol-1-ylmethyl)-2-methyl-propyl]-carbamic acid 1-(S)-cyclohexyl-2-morpholin-4-yl-2-oxo-ethyl ester

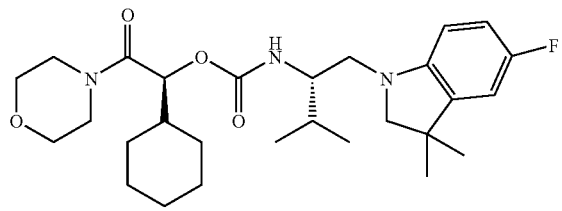

Compound is synthesized as outlined in example 5 using (L)-tetrahydromandelic acid. HPLC-MS calcd. for $C_{28}H_{42}FN_3O_4$ (M+H$^+$) 504.3, found 504.6.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 µl in 384-well microtiter plates. Cathepsin S, at a final concentration of 0.3-3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 µM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 301 in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 µM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 t in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 µM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 µl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 µM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE I

Assay Data for Inhibitors of Cathepsin S

| Example | $K_i$ Cat. S$^a$ | Selectivity for Cat. S over Cat. K$^b$ | Selectivity for Cat. S over Cat. L$^b$ | Selectivity for Cat. S over Cat. B$^b$ |
|---|---|---|---|---|
| 1 | + | − | − | + |
| 2 | +++ | ++ | + | +++ |
| 3 | +++ | ++ | + | ++ |
| 4 | +++ | ++ | + | +++ |
| 5 | + | + | + | + |
| 6 | + | + | + | + |
| 7 | + | + | + | + |
| 8 | +++ | ++ | ++ | +++ |
| 9 | + | + | + | + |
| 10 | +++ | ++ | +++ | +++ |
| 11 | ++ | ++ | ++ | ++ |
| 12 | ++ | + | + | ++ |
| 13 | ++ | ++ | ++ | ++ |
| 14 | +++ | ++ | ++ | +++ |
| 15 | +++ | ++ | ++ | +++ |
| 16 | ++ | + | + | ++ |
| 17 | +++ | ++ | + | ++ |
| 18 | +++ | +++ | ++ | ++ |
| 19 | ++ | ++ | ++ | ++ |
| 20 | +++ | + | + | +++ |
| 21 | +++ | ++ | +++ | +++ |
| 22 | +++ | + | + | +++ |
| 23 | +++ | + | − | ++ |
| 24 | +++ | − | + | +++ |
| 25 | ++ | ++ | ++ | ++ |
| 26 | ++ | − | ++ | ++ |
| 27 | +++ | + | ++ | +++ |
| 28 | +++ | + | + | +++ |
| 29 | +++ | + | + | ++ |
| 30 | +++ | ++ | + | ++ |
| 31 | +++ | + | ++ | +++ |
| 32 | +++ | − | + | +++ |
| 33 | +++ | +++ | + | +++ |
| 34 | +++ | + | + | +++ |
| 35 | +++ | + | ++ | +++ |
| 36 | +++ | ++ | + | +++ |
| 37 | +++ | ++ | + | ++ |
| 38 | +++ | − | − | +++ |
| 39 | +++ | + | ++ | +++ |
| 40 | +++ | + | ++ | +++ |
| 41 | +++ | + | ++ | +++ |
| 42 | +++ | +++ | ++ | +++ |
| 43 | ++ | ++ | ++ | ++ |
| 44 | ++ | + | ++ | ++ |
| 45 | +++ | ++ | ++ | +++ |
| 46 | +++ | +++ | ++ | +++ |
| 47 | ++ | − | + | + |
| 48 | ++ | + | ++ | ++ |
| 49 | + | + | + | + |
| 50 | +++ | ++ | − | +++ |
| 51 | +++ | ++ | + | +++ |
| 52 | ++ | + | ++ | ++ |
| 53 | ++ | ++ | ++ | ++ |
| 54 | +++ | +++ | ++ | +++ |
| 55 | ++ | +++ | ++ | ++ |
| 56 | − | − | − | − |
| 57 | ++ | ++ | ++ | ++ |
| 58 | ++ | ++ | + | ++ |
| 59 | + | + | + | + |
| 60 | + | + | + | + |
| 61 | + | + | + | + |
| 62 | ++ | ++ | ++ | ++ |
| 63 | ++ | ++ | ++ | ++ |
| 64 | ++ | + | + | ++ |
| 65 | ++ | ++ | ++ | ++ |
| 66 | + | − | − | + |
| 67 | + | + | + | + |
| 68 | +++ | ++ | +++ | +++ |
| 69 | ++ | + | ++ | ++ |
| 70 | ++ | ++ | ++ | ++ |
| 71 | + | − | ++ | + |
| 72 | +++ | ++ | + | ++ |
| 73 | +++ | + | + | ++ |
| 74 | +++ | + | − | + |
| 75 | +++ | + | − | + |
| 76 | ++ | + | − | + |
| 77 | ++ | + | + | ++ |
| 78 | + | + | − | + |
| 79 | + | + | − | + |
| 80 | +++ | +++ | + | +++ |
| 81 | +++ | ++ | + | +++ |
| 82 | +++ | ++ | − | ++ |
| 83 | ++ | ++ | ++ | ++ |
| 84 | + | − | + | + |
| 85 | + | − | + | + |
| 86 | +++ | ++ | ++ | +++ |
| 87 | +++ | ++ | ++ | +++ |
| 88 | +++ | + | ++ | +++ |
| 89 | + | + | + | + |
| 90 | ++ | ++ | ++ | ++ |
| 91 | + | + | + | + |
| 92 | +++ | +++ | +++ | +++ |
| 93 | + | + | − | + |
| 94 | + | + | + | + |
| 95 | + | + | + | + |
| 96 | + | + | + | + |
| 97 | + | + | − | + |
| 98 | + | + | + | + |
| 99 | + | + | + | + |
| 100 | + | + | + | + |
| 101 | ++ | ++ | ++ | ++ |
| 102 | +++ | +++ | +++ | +++ |
| 103 | +++ | ++ | +++ | +++ |
| 104 | ++ | ++ | ++ | ++ |
| 105 | ++ | + | + | ++ |
| 106 | ++ | ++ | ++ | ++ |
| 107 | ++ | ++ | ++ | ++ |
| 108 | +++ | +++ | +++ | +++ |
| 109 | + | − | + | + |
| 110 | + | + | + | + |
| 111 | +++ | + | ++ | +++ |

$^a$Cathepsin S inhibition constant for compounds of Formula I: +, <10 μM; ++, <1.0 μM; +++, <0.1 μM.
$^b$Selectivity of compounds of Formula I for cathepsin S over another cathepsin: +, >10; ++, >100; +++, >1000.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A compound having the Formula I:

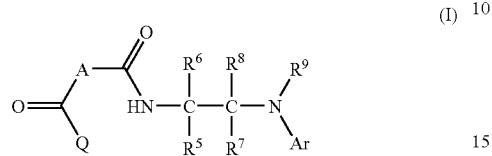

or a pharmaceutically acceptable salt or prodrug thereof, wherein:

Q is a thiomorpholinyl substituted with 0-2 $R^Q$, wherein Q is connected to —C(=O)— via a ring nitrogen atom;

each $R^Q$ is independently a member selected from the group consisting of OH, F, Cl, —S(=O)$_2$CH$_3$—, acetyl, =O, C$_1$-C$_6$ alkyl, C$_1$-C$_6$ alkoxy, CF$_3$, OCF$_3$ and NR$^{10}$R$^{11}$;

A is a member selected from the group consisting of —O—CR$^1$R$^2$—, —NH—CR$^1$R$^2$—, —CR$^3$R$^4$—O—, and —CR$^3$R$^4$—CR$^1$R$^2$—;

each of R$^1$ and R$^3$ is independently a member selected from the group consisting of H, a C$_1$-C$_6$ alkoxy, a C$_1$-C$_6$ alkyl substituted with 0-2 R$^{1a}$, wherein said C$_1$-C$_6$ alkyl may optionally contain a heteroatom selected from the group consisting of —O—, —S—, —S(=O)— and —S(=O)$_2$—; a C$_2$-C$_6$ alkenyl, a C$_3$-C$_6$ alkynyl, a C$_3$-C$_7$ cycloalkyl substituted with 0-2 R$^Q$, and a C$_7$-C$_{11}$ bicycloalkyl substituted with 0-2 R$^Q$; phenyl substituted with 0-3 R$^{13}$, a 5- to 6-membered heteroaryl containing 1 to 4 heteroatoms each independently a member selected from the group consisting of N, O and S, wherein said heteroaryl is substituted with 0-3 R$^{13}$;

each R$^{1a}$ is independently a member selected from the group consisting of a C$_6$-C$_{10}$ aryl substituted with 0-3 R$^{13}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 R$^{13}$, a C$_3$-C$_8$ cycloalkyl substituted with 0-2 R$^Q$, a C$_7$-C$_{11}$ bicycloalkyl substituted with 0-2 R$^Q$, and a C$_1$-C$_3$ perfluoroalkyl;

each of R$^2$ and R$^4$ is independently a member selected from the group consisting of H, F, OH, C$_1$-C$_6$ alkyl and C$_1$-C$_6$ alkoxy;

R$^5$ is a member selected from the group consisting of H, C(=O)OR$^{14}$, C(=O)NR$^{15}$R$^{16}$, phenyl substituted with 0-2 R$^{13}$, and a 5- to 6-membered heteroaryl containing 1 to 4 heteroatoms each independently a member selected from the group consisting of N, O and S, wherein said heteroaryl is substituted with 0-2 R$^{13}$, C$_3$-C$_7$ cycloalkyl, C$_1$-C$_6$ alkyl substituted with 0-2 R$^{21}$, wherein said C$_1$-C$_6$ alkyl may optionally contain a heteroatom selected from the group consisting of —O—, —S—, —S(=O)—, —S(=O)$_2$— and —NR$^{22}$—;

each of R$^6$, R$^7$, R$^8$ and R$^9$ is independently a member selected from the group consisting of H and C$_1$-C$_6$ alkyl;

alternatively, R$^5$ and R$^7$ are taken together to form a C$_5$-C$_7$ cycloalkyl, wherein a methylene of said C$_5$-C$_7$ cycloalkyl may optionally be replaced with a heteroatom selected from the group of —O—, —S—, —S(=O)—, and —S(=O)$_2$—;

each R$^{10}$ is independently a member selected from the group consisting of H, C$_1$-C$_4$ alkyl, (C$_1$-C$_4$ alkyl)-C(=O)— and (C$_1$-C$_4$ alkyl)-S(=O)$_2$—;

each R$^{11}$ is independently a member selected from the group consisting of H and C$_1$-C$_4$ alkyl;

each R$^{12}$ is independently a member selected from the group consisting of H, C$_3$-C$_8$ cycloalkyl, a phenyl substituted with 0-3 R$^{13}$, a 5- to 6-membered heteroaryl containing 1 to 4 heteroatoms each independently a member selected from the group consisting of N, O and S, wherein said 5- to 6-membered heteroaryl is substituted with 0-3 R$^{13}$, and a C$_1$-C$_6$ alkyl substituted with 0-1 R$^{19}$;

each R$^{13}$ is independently a member selected from the group consisting of H, OH, F, Cl, Br, CN, NO$_2$, COOR$^{17}$, C(=O)NR$^{17}$R$^{18}$, S(=O)$_2$NR$^{17}$R$^{18}$, acetyl, —SCH$_3$, —S(=O)CH$_3$, —S(=O)$_2$CH$_3$, —NR$^{10}$R$^{11}$, C$_1$-C$_6$ alkoxy, C$_1$-C$_3$ perfluoroalkyl, C$_1$-C$_3$ perfluoroalkoxy and a C$_1$-C$_6$ alkyl;

each R$^{14}$ is independently a member selected from the group consisting of H, C$_3$-C$_7$ cycloalkyl, C$_1$-C$_4$ alkyl substituted with 0-1 R$^{19}$, and a phenyl substituted with 0-3 R$^{13}$;

each R$^{15}$ is independently a member selected from the group consisting of H, C$_3$-C$_8$ cycloalkyl, a phenyl substituted with 0-3 R$^{13}$, and a C$_1$-C$_6$ alkyl substituted with 0-1 R$^{19}$;

each R$^{16}$ is independently a member selected from the group consisting of H and C$_1$-C$_4$ alkyl;

alternatively, R$^{15}$ and R$^{16}$ on the same N atom are taken together to form a C$_5$-C$_7$ heterocycle containing 1-2 heteroatoms each independently a member selected from the group consisting of N, O and S;

each of R$^{17}$ and R$^{18}$ is independently a member selected from the group consisting of H, C$_1$-C$_4$ alkyl and C$_3$-C$_6$ cycloalkyl;

each R$^{19}$ is independently a member selected from the group consisting of H, C$_3$-C$_7$ cycloalkyl, a phenyl substituted with 0-3 R$^{13}$ and a 5- to 6-membered heteroaryl containing 1 to 4 heteroatoms each independently a member selected from the group consisting of N, O and S, wherein said 5- to 6-membered heteroaryl is substituted with 0-3 R$^{13}$;

Ar is a member selected from the group consisting of phenyl substituted with 0-3 R$^{20}$, and a 5- to 10-membered heteroaryl containing 1 to 4 heteroatoms each independently a member selected from the group consisting of N, O and S; wherein said heteroaryl is substituted with 0-3 R$^{20}$;

each R$^{20}$ is independently a member selected from the group consisting of H, F, Cl, Br, CN, OR$^{12}$, SCH$_3$, S(=O)CH$_3$, S(=O)$_2$CH$_3$, S(=O)$_2$NR$^{17}$R$^{18}$, NR$^{10}$R$^{11}$, acetyl, —S(=O)$_2$NH(C=O)CH$_3$, C(=O)NR$^{17}$R$^{18}$, CO$_2$R$^{17}$, C(=NH)NH$_2$, C$_1$-C$_6$ alkyl, CF$_3$, OCF$_3$ and OCF$_2$H;

alternatively, R$^{20}$ and R$^9$ are taken together to form a 5- to 7-membered heterocyclic ring containing 1-2 heteroatoms each independently a member selected from the group consisting of N, O and S; wherein said 5 to 7 membered heterocyclic ring is ortho-fused to Ar; wherein said 5- to 7-membered heterocyclic ring may be optionally substituted with 0-2 R$^{24}$;

each R$^{21}$ is independently a member selected from the group consisting of H, OH, F, Cl, CN, NO$_2$, C(=O)OR$^{14}$, C(=O)NR$^{15}$R$^{16}$, NR$^{22}$R$^{23}$, C$_1$-C$_3$ perfluoroalkoxy, $C_1$-$C_4$ alkoxy, $C_2$-$C_4$ alkenyl, $C_2$-$C_4$ alkynyl, phenyl substituted with 0-3 $R^{13}$, a 5- to 6-membered heteroaryl containing 1 to 4 heteroatoms each independently a member selected from the group consisting of N, O and S, wherein said heteroaryl is substituted with 0-3 $R^{13}$, $C_3$-$C_8$ heterocycle containing 1 to 2 heteroatoms each independently a member selected from the group consisting of N, O and S, wherein said heterocycle is substituted with 0-2 $R^{13}$ and is saturated or partially unsaturated, and $C_3$-$C_8$ cycloalkyl;

$R^{22}$ is independently a member selected from the group consisting of H, t-butoxycarbonyl, benzyloxycarbonyl, $C_3$-$C_8$ cycloalkyl, ($C_1$-$C_6$ alkyl)-C(=O)—, ($C_1$-$C_6$ alkyl)-S(=O)$_2$—, a $C_1$-$C_6$ alkyl substituted with 0-1 $R^{19}$, a phenyl substituted with 0-3 $R^{13}$ and a 5- to 6-membered heteroaryl containing 1 to 4 heteroatoms each independently a member selected from the group consisting of N, O and S, wherein said 5- to 6-membered heteroaryl is substituted with 0-3 $R^{13}$;

each $R^{23}$ is independently a member selected from the group consisting of H and $C_1$-$C_4$ alkyl;

each $R^{24}$ is independently a member selected from the group consisting of $C_1$-$C_4$ alkyl, F, Cl and $C_1$-$C_4$ alkoxy, $CF_3$ and $OCF_3$;

alternatively, two $R^{24}$ may be combined to form $C_3$-$C_6$ cycloalkyl.

2. The compound of claim 1, wherein said compound has the formula:

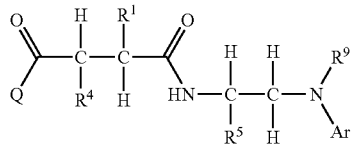

(Ia)

wherein:
$R^1$ is independently a member selected from the group consisting of H, $C_1$-$C_6$ alkyl substituted with 0-1 $R^{1a}$, wherein said $C_1$-$C_6$ alkyl may optionally contain a heteroatom selected from the group consisting of —O—, —S—, and —S(=O)$_2$, a $C_2$-$C_6$ alkenyl, a $C_3$-$C_7$ cycloalkyl substituted with 0-2 $R^Q$, and a $C_7$-$C_{11}$ bicycloalkyl substituted with 0-2 $R^Q$; phenyl substituted with 0-3 $R^{13}$, a 5- to 6-membered heteroaryl containing 1 to 4 heteroatoms each independently a member selected from the group consisting of N, O and S, wherein said heteroaryl is substituted with 0-3 $R^{13}$; and
$R^4$ is a member selected from the group consisting of H, F, OH and $C_1$-$C_6$ alkyl.

3. The compound of claim 1, wherein said compound has the formula:

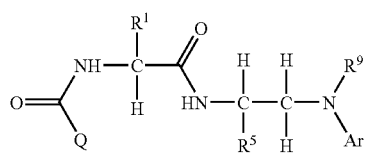

(Ib)

wherein:
$R^1$ is selected from the group consisting of $C_1$-$C_6$ alkyl, $C_1$-$C_4$ alkyl substituted with 1 $R^{1a}$, wherein said $C_1$-$C_4$ alkyl may optionally contain a heteroatom selected from the group consisting of —O—, —S— and —S(=O)$_2$—; and $R^{1a}$ is a member selected from the group consisting of a phenyl substituted with 0-3 $R^{13}$, a $C_3$-$C_7$ cycloalkyl substituted with 0-2 $R^Q$, and a $C_7$-$C_{11}$ bicycloalkyl substituted with 0-2 $R^Q$.

4. The compound of claim 1, wherein said compound has the formula:

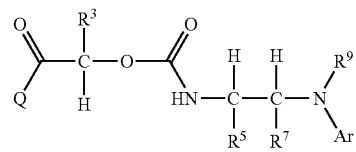

(Ic)

wherein:
$R^3$ is selected from the group consisting of $C_1$-$C_6$ alkyl, $C_1$-$C_4$ alkyl substituted with 1 $R^{1a}$, wherein said $C_1$-$C_4$ alkyl may optionally contain a heteroatom selected from the group consisting of —O—, —S— and —S(=O)$_2$—; a $C_3$-$C_7$ cycloalkyl substituted with 0-2 $R^Q$, and a $C_7$-$C_{11}$ bicycloalkyl substituted with 0-2 $R^Q$; phenyl substituted with 0-3 $R^{13}$; and $R^{1a}$ is a member selected from the group consisting of a phenyl substituted with 0-3 $R^{13}$, a $C_3$-$C_7$ cycloalkyl substituted with 0-2 $R^Q$, and a $C_7$-$C_{11}$ bicycloalkyl substituted with 0-2 $R^Q$.

5. The compound of claim 1, wherein said compound has the formula:

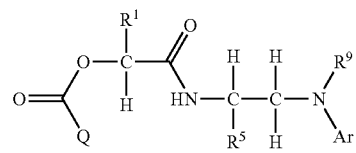

(Id)

wherein:
$R^1$ is selected from the group consisting of $C_1$-$C_6$ alkyl, $C_1$-$C_4$ alkyl substituted with 1 $R^{1a}$, wherein said $C_1$-$C_4$ alkyl may optionally contain a heteroatom selected from the group consisting of —O—, —S—, and —S(=O)$_2$;

$R^{1a}$ is a member selected from the group consisting of a phenyl substituted with 0-3 $R^{13}$, $C_3$-$C_7$ cycloalkyl substituted with 0-2 $R^Q$, and a $C_7$-$C_{11}$ bicycloalkyl substituted with 0-2 $R^Q$;

$R^5$ is a member selected from the group consisting of H, phenyl substituted with 0-2 $R^{13}$, $C_3$-$C_7$ cycloalkyl, $C_1$-$C_6$ alkyl substituted with 0-1 $R^{21}$, wherein said $C_1$-$C_6$ alkyl may optionally contain a heteroatom selected from the group consisting of —O—, —S—, —S(=O)$_2$—;

each $R^{21}$ is independently a member selected from the group consisting of H, OH, F, C(=O)OR$^{14}$, C(=O)NR$^{15}$R$^{16}$, NR$^{22}$R$^{23}$, phenyl substituted with 0-3 $R^{13}$, and $C_3$-$C_7$ cycloalkyl;

Ar is a member selected from the group consisting of phenyl substituted with 0-3 $R^{20}$;

each $R^{20}$ is independently a member selected from the group consisting of H, F, Cl, Br, CN, OR$^{12}$, SCH$_3$, $S(=O)CH_3$, $S(=O)_2CH_3$, $S(=O)_2NR^{17}R^{18}$, $NR^{10}R^{11}$, acetyl, $C(=O)NR^{17}R^{18}$, $CO_2R^{17}$, $C(=NH)NH_2$, $C_1$-$C_6$ alkyl, $CF_3$, $OCF_3$;

alternatively, $R^{20}$ and $R^9$ are taken together to form a 5-membered heterocyclic ring containing 1 nitrogen, wherein said 5-membered heterocyclic ring is ortho-fused to Ar; wherein said 5-membered heterocyclic ring may be optionally substituted with 0-2 $R^{24}$.

6. The compound of claim 1, wherein said compound has the formula:

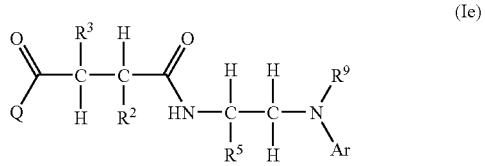

(Ie)

wherein:
$R^2$ is H;
$R^3$ are each independently selected from the group consisting of H, $C_1$-$C_6$ alkyl, $C_1$-$C_4$ alkyl substituted with 1 $R^{1a}$,
$R^{1a}$ is a member selected from the group consisting of a $C_3$-$C_7$ cycloalkyl substituted with 0-2 $R^Q$, and a $C_7$-$C_{11}$ bicycloalkyl substituted with 0-2 $R^Q$;
$R^5$ is a member selected from the group consisting of H, phenyl substituted with 0-2 $R^{13}$, $C_3$-$C_7$ cycloalkyl, $C_1$-$C_6$ alkyl substituted with 0-1 $R^{21}$, wherein said $C_1$-$C_6$ alkyl may optionally contain a heteroatom selected from the group consisting of —O—, —S—, —S(=O)$_2$—;
each $R^{21}$ is independently a member selected from the group consisting of H, OH, $C(=O)OR^{14}$, $C(=O)NR^{15}R^{16}$, $NR^{22}R^{23}$, phenyl substituted with 0-3 $R^{13}$, and $C_3$-$C_8$ cycloalkyl;
Ar is a member selected from the group consisting of phenyl substituted with 0-3 $R^{20}$, each $R^{20}$ is independently a member selected from the group consisting of H, F, Cl, Br, CN, $OR^{12}$, $SCH_3$, $S(=O)CH_3$, $S(=O)_2CH_3$, $S(=O)_2NR^{17}R^{18}$, $NR^{10}R^{11}$, acetyl, —$S(=O)_2NH(C=O)CH_3$, $C(=O)NR^{17}R^{18}$, $CO_2R^{17}$, $C(=NH)NH_2$, $C_1$-$C_6$ alkyl, $CF_3$, $OCF_3$ and $OCF_2H$;
alternatively, $R^{20}$ and $R^9$ are taken together to form a 5-membered heterocyclic ring containing 1 nitrogen; wherein said 5-membered heterocyclic ring is ortho-fused to Ar; wherein said 5-membered heterocyclic ring may be optionally substituted with 0-2 $R^{24}$.

7. The compound of claim 2, wherein:
$R^5$ is a member selected from the group consisting of H, phenyl substituted with 0-2 $R^{13}$, $C_3$-$C_7$ cycloalkyl, $C_1$-$C_6$ alkyl substituted with 0-1 $R^{21}$, wherein said $C_1$-$C_6$ alkyl may optionally contain a heteroatom selected from the group consisting of —O—, —S—, —S(=O)$_2$—; and
each $R^{21}$ is independently a member selected from the group consisting of H, OH, $C(=O)OR^{14}$, $C(=O)NR^{15}R^{16}$, $NR^{22}R^{23}$, phenyl substituted with 0-3 $R^{13}$, and $C_3$-$C_7$ cycloalkyl.

8. The compound of claim 7, wherein:
$R^1$ is a member selected from the group consisting of $C_1$-$C_4$ alkyl substituted with 1 $R^{1a}$, wherein said $C_1$-$C_4$ alkyl may optionally contain a heteroatom selected from the group consisting of —O—, —S—, and —$S(=O)_2$; $C_1$-$C_6$ alkyl, a $C_2$-$C_6$ alkenyl, a $C_3$-$C_7$ cycloalkyl substituted with 0-2 $R^Q$, and a $C_7$-$C_{11}$ bicycloalkyl substituted with 0-2 $R^Q$; phenyl substituted with 0-3 $R^{13}$;

each $R^{1a}$ is independently a member selected from the group consisting of a phenyl substituted with 0-3 $R^{13}$, a $C_3$-$C_8$ cycloalkyl substituted with 0-2 $R^Q$, a $C_7$-$C_{11}$ bicycloalkyl substituted with 0-2 $R^Q$;
$R^4$ is H, F, OH, methyl, ethyl, propyl or butyl; and
Ar is a phenyl substituted with 0-3 $R^{20}$; a 5- to 6-membered heteroaryl containing 1 to 2 heteroatoms each independently a member selected from the group consisting of N, O and S; wherein said heteroaryl is substituted with 0-2 $R^{20}$.

9. The compound of claim 8, wherein
Q is thiomorpholinyl or 1,1-dioxo-1$\lambda^6$-thiomorpholinyl, wherein Q is connected to —C(=O)— via a ring nitrogen atom;
$R^1$ is independently a member selected from the group consisting of cyclohexylmethyl, 4,4-dimethyl-cyclohexylmethyl, spiro[2.5]oct-6-ylmethyl, spiro[3.5]non-7-ylmethyl, cyclohexylethyl, cyclopentylmethyl, cyclopentylethyl, cyclobutylmethyl, cyclobutylethyl, cyclopropylmethyl, cyclopropylethyl, allyl, butenyl, cyclopentyl, cyclohexyl, t-butylmethyl, t-butylethyl, 4-ethyl-4-hydroxyl-cyclohexylmethyl, phenethyl, phenylpropyl, phenyl, 4-fluorophenyl, 4-methylphenyl, 4-trifluoromethylphenyl, 4-chlorophenyl, 4-methoxyphenyl, 4-trifluoromethoxyphenyl and 4-methylsulfonylphenyl;
$R^4$ is H or methyl;
$R^5$ is a member selected from the group consisting of H, methyl, ethyl, propyl, i-propyl, butyl, i-butyl, cyclopropyl, cyclopropylmethyl, methylsulfonylmethyl, methylsulfonylethyl, hydroxylmethyl, hydroxyethyl, phenethyl, benzyl, phenyl and benzyloxymethyl;
Ar is phenyl substituted with 0-3 $R^{20}$, isoxazolyl substituted with 0-2 $R^{20}$, pyridyl substituted with 0-2 $R^{20}$;
each $R^{20}$ is independently a member selected from the group consisting of H, F, Cl, $OCH_3$, $CH_3$, $SCH_3$, $S(=O)_2CH_3$, $S(=O)_2NH_2$, acetyl, $C(=O)NH_2$, $CO_2H$, $OCF_3$ and $OCHF_2$;
alternatively, $R^{20}$ and $R^9$ are taken together to form a 5-membered heterocyclic ring containing 1 nitrogen atom; wherein said 5-membered heterocyclic ring is ortho-fused to Ar; wherein said 5-membered heterocyclic ring may be optionally substituted with 0-2 $R^{24}$;
each $R^{24}$ is independently a member selected from the group consisting of methyl, and F;
alternatively, two $R^{24}$ may be combined to form cyclopropyl and cyclobutyl.

10. The compound of claim 3, wherein
$R^5$ is a member selected from the group consisting of H, phenyl substituted with 0-2 $R^{13}$, $C_3$-$C_7$ cycloalkyl, $C_1$-$C_6$ alkyl substituted with 0-1 $R^{21}$, wherein said $C_1$-$C_6$ alkyl may optionally contain a heteroatom selected from the group consisting of —O—, —S—, —$S(=O)_2$—; and
each $R^{21}$ is independently a member selected from the group consisting of H, OH, $C(=O)OR^{14}$, $C(=O)NR^{15}R^{16}$, $NR^{22}R^{23}$, $C_1$-$C_4$ alkoxy, phenyl substituted with 0-3 $R^{13}$, and $C_3$-$C_8$ cycloalkyl.

11. The compound of claim 10, wherein
Q is thiomorpholinyl or 1,1-dioxo-1$\lambda^6$-thiomorpholinyl, wherein Q is connected to —C(=O)— via a ring nitrogen atom;
$R^1$ is independently a member selected from the group consisting of cyclohexylmethyl, 4,4-dimethyl-cyclohexylmethyl, spiro[2.5]oct-6-ylmethyl, spiro[3.5]non-7-ylmethyl, cyclohexylethyl, cyclopentylmethyl, cyclopentylethyl, cyclobutylmethyl, cyclobutylethyl, cyclopropylmethyl, cyclopropylethyl, t-butylmethyl, t-butylethyl, phenylmethylsulfonylmethyl and benzylsulfanylmethyl;

$R^5$ is a member selected from the group consisting of H, methyl, ethyl, propyl, i-propyl, butyl, i-butyl, cyclopropyl, cyclopropylmethyl, methylsulfonylmethyl, methylsulfonylethyl, hydroxylmethyl, hydroxyethyl, benzyloxymethyl, phenethyl, benzyl and phenyl;

Ar is phenyl substituted with 0-3 $R^{20}$, pyridinyl substituted with 0-2 $R^{20}$, and isoxazolyl substituted with 0-2 $R^{20}$;

each $R^{20}$ is independently a member selected from the group consisting of H, F, Cl, $CH_3$, $OCH_3$, $SCH_3$, $S(=O)_2CH_3$, $S(=O)_2NH_2$, acetyl, $C(=O)NH_2$, $CO_2H$, $OCF_3$ and $OCHF_2$;

alternatively, $R^{20}$ and $R^9$ are taken together to form a 5-membered heterocyclic ring containing 1 nitrogen atom; wherein said 5-membered heterocyclic ring is ortho-fused to Ar; wherein said 5-membered heterocyclic ring may be optionally substituted with 0-2 $R^{24}$;

each $R^{24}$ is independently a member selected from the group consisting of methyl, ethyl and F;

alternatively, two $R^{24}$ may be combined to form cyclopropyl and cyclobutyl.

12. The compound of claim 4, wherein
$R^5$ is a member selected from the group consisting of H, phenyl substituted with 0-2 $R^{13}$, $C_3$-$C_7$ cycloalkyl, $C_1$-$C_6$ alkyl substituted with 0-1 $R^{21}$, wherein said $C_1$-$C_6$ alkyl may optionally contain a heteroatom selected from the group consisting of —O—, —S—, —S(=O)$_2$—;

each $R^{21}$ is independently a member selected from the group consisting of H, OH, $C(=O)OR^{14}$, $C(=O)NR^{15}R^{16}$, $NR^{22}R^{23}$, $C_1$-$C_4$ alkoxy, phenyl substituted with 0-3 $R^{13}$, and $C_3$-$C_8$ cycloalkyl; and $R^7$ is H.

13. The compound of claim 12, wherein
Q is thiomorpholinyl or 1,1-dioxo-1$\lambda^6$-thiomorpholinyl, wherein Q is connected to —C(=O)— via a ring nitrogen atom;

$R^3$ is independently a member selected from the group consisting of cyclohexylmethyl, 4,4-dimethyl-cyclohexylmethyl, spiro[2.5]oct-6-ylmethyl, spiro[3.5]non-7-ylmethyl, cyclohexylethyl, cyclopentylmethyl, cyclopentylethyl, cyclobutylmethyl, cyclobutylethyl, cyclopropylmethyl, cyclopropylethyl, t-butylmethyl, t-butylethyl, phenyl, cyclohexyl, cyclopentyl, 4,4-dimethylcyclohexyl, phenylmethylsulfonylmethyl and benzylsulfanylmethyl;

$R^5$ is a member selected from the group consisting of H, methyl, ethyl, propyl, i-propyl, butyl, i-butyl, cyclopropyl, cyclopropylmethyl, methylsulfonylmethyl, methylsulfonylethyl, hydroxylmethyl, hydroxyethyl, phenethyl, benzyl, phenyl and benzyloxymethyl;

Ar is phenyl substituted with 0-3 $R^{20}$, and isoxazolyl substituted with 0-2 $R^{20}$;

each $R^{20}$ is independently a member selected from the group consisting of H, F, Cl, $OCH_3$, $CH_3$, $SCH_3$, $S(=O)_2CH_3$, $S(=O)_2NH_2$, —$S(=O)_2NH(C=O)CH_3$, acetyl, $C(=O)NH_2$, $CO_2H$, $OCF_3$ and $OCHF_2$;

alternatively, $R^{20}$ and $R^9$ are taken together to form a 5-membered heterocyclic ring containing 1 nitrogen atom; wherein said 5-membered heterocyclic ring is ortho-fused to Ar; wherein said 5-membered heterocyclic ring may be optionally substituted with 0-2 $R^{24}$;

each $R^{24}$ is independently a member selected from the group consisting of methyl, and F;

alternatively, two $R^{24}$ may be combined to form cyclopropyl and cyclobutyl.

14. The compound of claim 1, wherein said compound is selected from the group consisting of:
  2-(R)-Cyclohexylmethyl-N-[1-(S)-methyl-2-(4-trifluoromethoxy-phenylamino)-ethyl]-4-oxo-4-thiomorpholin-4-yl-butyramide;
  2-(R)-Cyclohexylmethyl-4-(1,1-dioxo-thiomorpholin-4-yl)-N-[1-(S)-methyl-2-(4-trifluoromethoxy-phenylamino)-ethyl]-4-oxo-butyramide;
  [2-(5-Fluoro-2,2-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester;
  [2-(5-Fluoro-3,3-dimethyl-2,3-dihydro-indol-1-yl)-1-(S)-methyl-ethyl]-carbamic acid 1-(S)-cyclohexylmethyl-2-oxo-2-thiomorpholin-4-yl-ethyl ester; and
  [2-(5-Fluoro-3,3-dimethyl-2,3-dihydro-indol-1-yl)-1-(S)-methyl-ethyl]-carbamic acid 1-(S)-cyclohexylmethyl-2-(1,1-dioxo-1$\lambda^6$-thiomorpholin-4-yl)-2-oxo-ethyl ester.

15. A pharmaceutical composition, said composition comprising a compound of claim 1 and an excipient.

16. A pharmaceutical composition, said composition comprising a compound of claim 14 and an excipient.

* * * * *